(12) United States Patent
Briggs et al.

(10) Patent No.: US 12,064,544 B2
(45) Date of Patent: Aug. 20, 2024

(54) DEVICES, METHODS, AND SYSTEMS FOR PRIMING, SEPARATING, AND COLLECTING BLOOD COMPONENTS

(71) Applicant: MALLINCKRODT HOSPITAL PRODUCTS IP LIMITED, Dublin (IE)

(72) Inventors: Dennis Briggs, West Chester, PA (US); Simon Do, Pottstown, PA (US); Eric Rabeno, Lincoln University, PA (US); Abdoulaye Sangare, Thorndale, PA (US); Mark Vandlik, West Chester, PA (US); Vicki Fluck, Quakertown, PA (US); Christopher Turek, West Chester, PA (US)

(73) Assignee: Mallinckrodt Pharmaceuticals Ireland Limited, Dublin (IE)

( * ) Notice: Subject to any disclaimer, the term of this patent is extended or adjusted under 35 U.S.C. 154(b) by 1027 days.

(21) Appl. No.: 16/906,976

(22) Filed: Jun. 19, 2020

(65) Prior Publication Data
US 2020/0316285 A1   Oct. 8, 2020

Related U.S. Application Data

(63) Continuation of application No. 15/737,163, filed as application No. PCT/US2016/037868 on Jun. 16, 2016, now Pat. No. 10,828,415.
(Continued)

(51) Int. Cl.
*A61M 1/36* (2006.01)
*A61M 1/02* (2006.01)
*G01M 3/26* (2006.01)

(52) U.S. Cl.
CPC ........ *A61M 1/3696* (2014.02); *A61M 1/0209* (2013.01); *A61M 1/3609* (2014.02);
(Continued)

(58) Field of Classification Search
CPC .............. A61M 1/0209; A61M 1/3609; A61M 1/36222; A61M 1/36225;
(Continued)

(56) References Cited

U.S. PATENT DOCUMENTS 6,725,726 B1   4/2004 Adolfs et al.
2003/0222029 A1   12/2003 Muller
(Continued)

FOREIGN PATENT DOCUMENTS

EP   0242031   10/1987
EP   1674120 B1   6/2006
(Continued)

OTHER PUBLICATIONS

Extended European Search Report. for Application No. 22213505.5, mailed Mar. 2, 2023.
(Continued)

*Primary Examiner* — Benjamin J Klein
(74) *Attorney, Agent, or Firm* — SNELL & WILMER L.L.P.

(57) ABSTRACT

A photopheresis system (200) is disclosed, and that may be configured to execute one or more protocols. These protocols include: 1) protocols (400; 430; 460) for purging air out of a centrifuge bowl (210) used by the photopheresis system (200); 2) protocols (500; 510 550) for assessing the installation/operation of one or more pressure domes (330) used by the photopheresis system (200); and 3) protocols (580; 600; 660; 700; 740) for collecting buffy coat from blood processed by the photopheresis system (200).

23 Claims, 43 Drawing Sheets

Related U.S. Application Data

(60) Provisional application No. 62/288,324, filed on Jan. 28, 2016, provisional application No. 62/182,123, filed on Jun. 19, 2015.

(52) U.S. Cl.
CPC .... *A61M 1/36222* (2022.05); *A61M 1/36225* (2022.05); *A61M 1/362264* (2022.05); *A61M 1/362266* (2022.05); *A61M 1/3643* (2013.01); *A61M 1/3644* (2014.02); *A61M 1/3646* (2014.02); *A61M 1/3652* (2014.02); *A61M 1/3683* (2014.02); *A61M 2202/0439* (2013.01); *A61M 2205/051* (2013.01); *A61M 2205/053* (2013.01); *A61M 2205/3331* (2013.01); *A61M 2205/3334* (2013.01); *A61M 2205/6018* (2013.01); *A61M 2230/207* (2013.01); *G01M 3/26* (2013.01)

(58) Field of Classification Search
CPC ...... A61M 1/362264; A61M 1/362266; A61M 1/3643; A61M 1/3644; A61M 1/3646; A61M 1/3652; A61M 1/3683; A61M 1/3696; A61M 2202/0439; A61M 2205/051; A61M 2205/053; A61M 2205/3331; A61M 2205/3334; A61M 2205/6018; A61M 2230/207
See application file for complete search history.

(56) References Cited

U.S. PATENT DOCUMENTS

| | | | |
|---|---|---|---|
| 2004/0082458 A1 | 4/2004 | Odak et al. | |
| 2004/0127840 A1 | 7/2004 | Gara | |
| 2004/0195190 A1* | 10/2004 | Min | A61M 1/3696 210/85 |
| 2005/0126998 A1 | 6/2005 | Childers | |
| 2006/0155236 A1 | 7/2006 | Gara et al. | |
| 2006/0240964 A1 | 10/2006 | Lolachi et al. | |
| 2009/0211962 A1 | 8/2009 | Min et al. | |
| 2009/0215602 A1 | 8/2009 | Kyungyoon | |
| 2010/0298752 A1 | 11/2010 | Briggs | |
| 2011/0163030 A1 | 7/2011 | Weaver et al. | |
| 2015/0196706 A1* | 7/2015 | Radwanski | A61M 1/3696 422/44 |
| 2015/0367063 A1* | 12/2015 | Kimura | A61M 1/0209 494/10 |

FOREIGN PATENT DOCUMENTS

| | | |
|---|---|---|
| EP | 1749546 A1 | 2/2007 |
| EP | 1674120 B1 | 8/2009 |
| JP | 2021130033 | 9/2021 |
| WO | 0117584 | 3/2001 |
| WO | 0117606 A1 | 3/2001 |
| WO | 2009085350 A1 | 7/2009 |
| WO | 2012009177 | 1/2012 |
| WO | 2014123521 A1 | 8/2014 |

OTHER PUBLICATIONS

International Search Report and Written Opinion of the International Searching Authority (Forms PCT/ISA/220, PCT/ISA/210 and PCT/ISA/237), dated Nov. 16, 2016, for International Application No. PCT/US2016/037868.
USPTO; Notice of Allowance dated Jun. 24, 2020 in U.S. Appl. No. 15/737,163.
JPO; Notice of Reasons for Refusal dated May 2, 2023 in Japanese Application 2022127884.
AUIPO; First Office Action dated Mar. 7, 2023 in Australian Application 2021206852.
CIPO, Canadian Office Action dated Jun. 13, 2023 in Application No. 3,155,961.
EPO; Intent to Grant dated Jun. 3, 2024 in European Application No. 22213505.5.
CIPO; Combined Canadian Office Action and Examination Search Report dated Apr. 15, 2024 in Application No. 3155961.

* cited by examiner

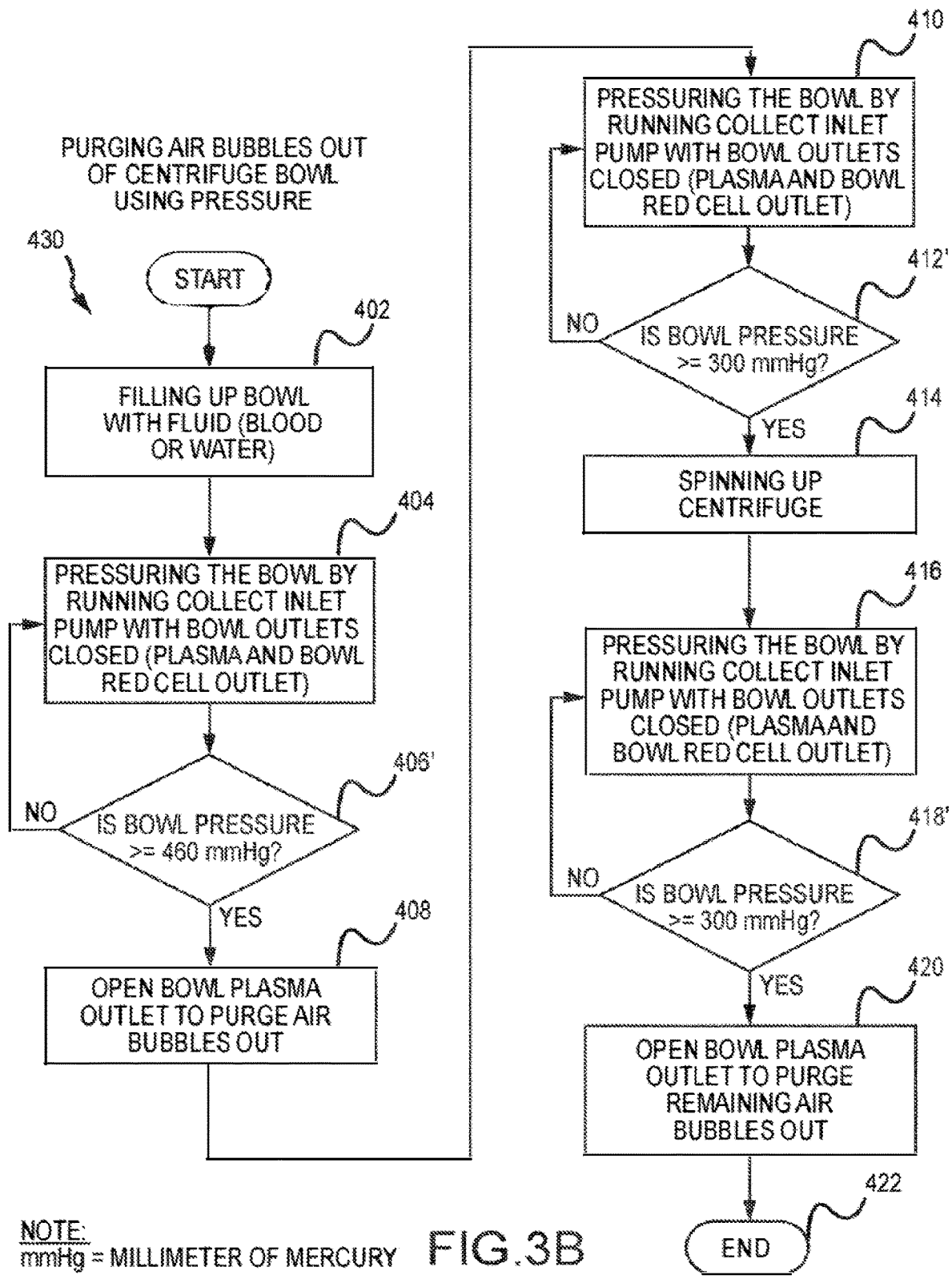

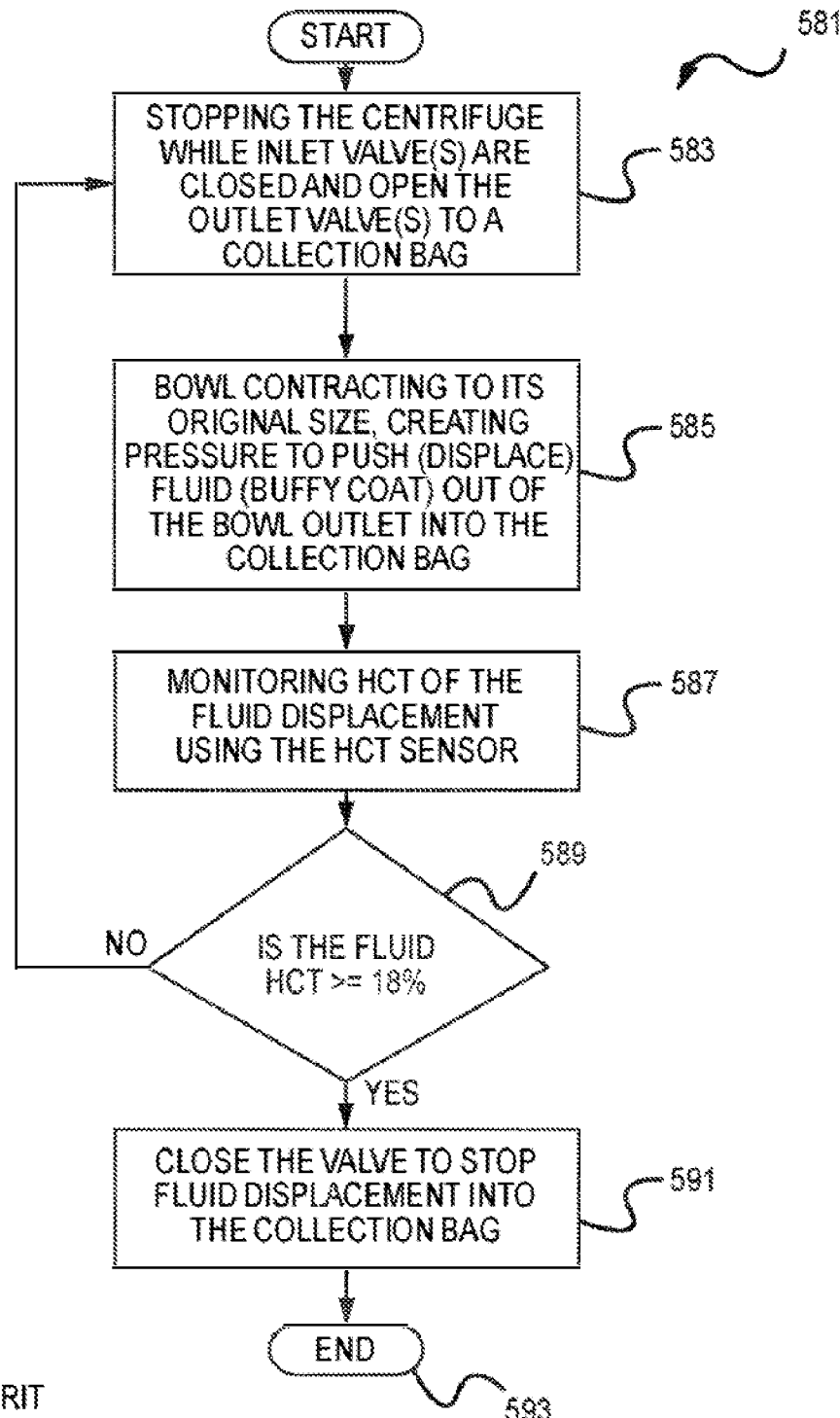

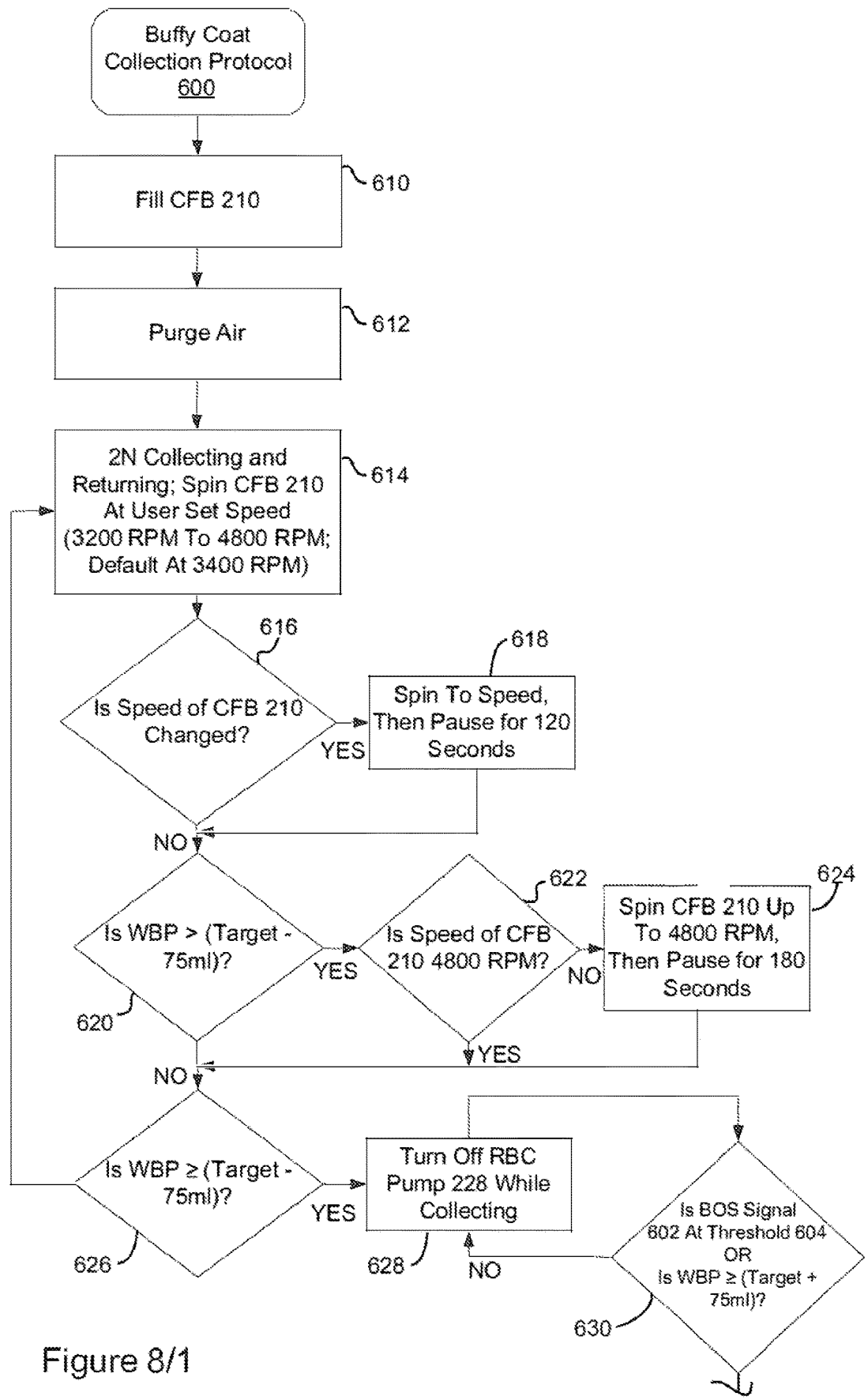
Figure 8/1

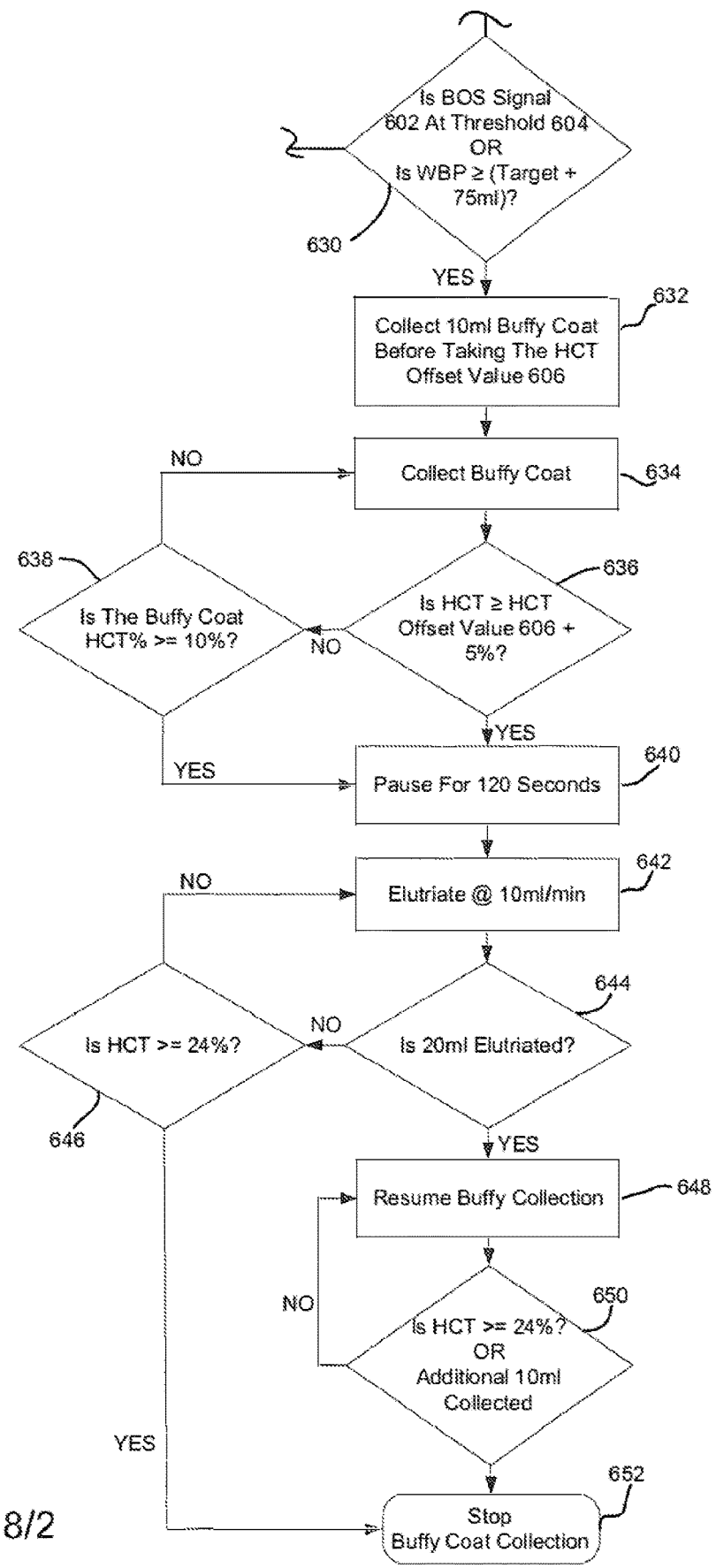
Figure 8/2

Optimizing Treatment Time And Methoxalen Dose Base On Patient White Blood Cell Count Note:
WBC = White Blood Cell Count

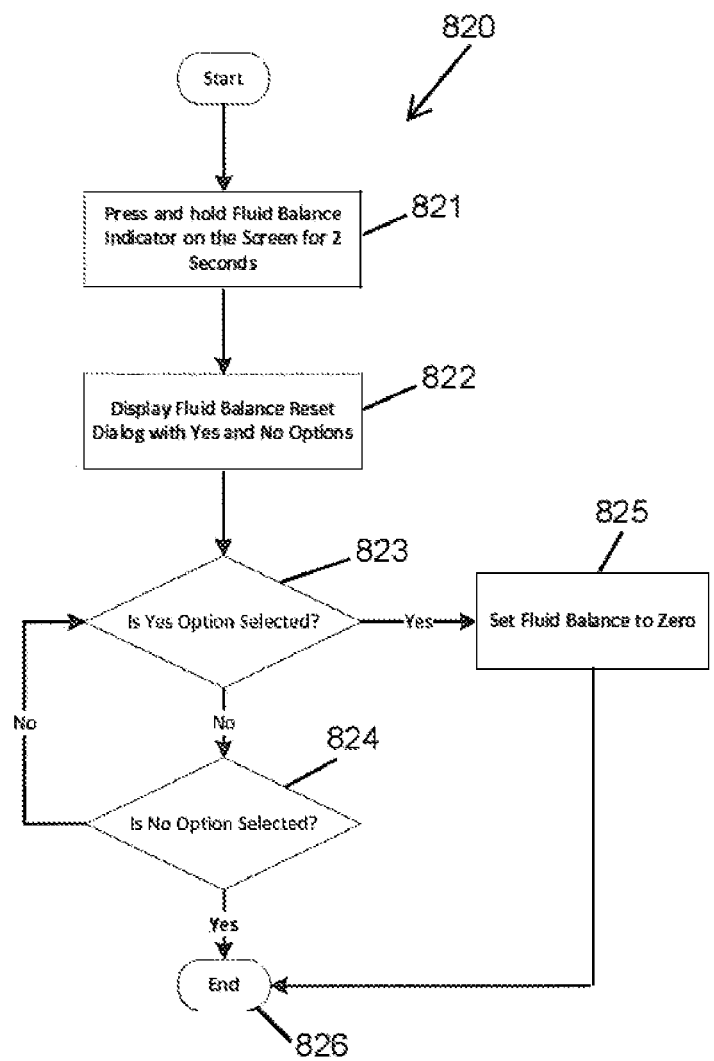

Operator Identification (ID) Capturing

Note:
ID = Identification Number

Concentrating Buffy Coat During Buffy Coat Collection

Note:
HCT = Hematocrit
(Volume percentage of red blood cells in blood)

Reducing Patient Residual Blood Volume In Disposable Kit

Note:
AC = Anticoagulant
ml = Milliliter

How To Detect Anemic Patient And Unintended Recirculation Of Blood

Note:
ml = Milliliter

DEVICES, METHODS, AND SYSTEMS FOR PRIMING, SEPARATING, AND COLLECTING BLOOD COMPONENTS

CROSS-REFERENCE TO RELATED APPLICATIONS

This patent application is continuation of co-pending U.S. patent application Ser. No. 15/737,163, having a filing/§ 371(c) date of Dec. 15, 2017, which is a U.S. National Stage of PCT/US2016/037868, filed Jun. 16, 2016, which is a non-provisional patent application of and claims priority to each of the following applications: 1) U.S. Provisional Patent Application No. 62/182,123, filed on Jun. 19, 2015; and 2) U.S. Provisional Patent Application Ser. No. 62/288,324, filed on Jan. 28, 2016. The entire disclosure of each patent application that is set forth in this Cross-Reference to Related Applications section is hereby incorporated by reference.

FIELD

Embodiments of the present disclosure relate to priming, separating, and collecting blood components.

SUMMARY

Embodiments of this disclosure present systems, methods and devices which prime, separate, collect, and treat blood components. Some embodiments of this disclosure comprise a combination of one or more features, modules, and/or functionality disclosed herein with one or more methods, systems, and/or devices presented in previous disclosures, for example, U.S. Pat. Nos. 6,219,584 and 7,479,123 and US Publication No. 2010/0298752, all of which are herein incorporated by reference in their entireties.

This disclosure addresses a photopheresis system where whole blood can be directed into a centrifuge or centrifuge bowl at the same time that certain components of the whole blood (e.g., plasma and/or red blood cells) are withdrawn from the centrifuge bowl (and are either then returned to the patient or are directed into a patient or collection bag for subsequent reinfusion to the patient), all while the photopheresis system is fluidly connected with the patient. Certain blood components (e.g., buffy coat) may be allowed to accumulate in the centrifuge bowl as whole blood continues to be directed into the photopheresis system (and where other blood components may be removed from the centrifuge bowl, as noted). In any case, the buffy coat is ultimately removed from the centrifuge bowl and is directed into a treatment bag (e.g., after processing a certain volume of whole blood), where thereafter the buffy coat is subjected to phototherapy (e.g., photoactivation), for instance where the contents of the treatment bag are recirculated through a photoactivation module. After phototherapy the contents of the treatment bag are reinfused to the patient. Other blood components may also be reinfused to the patient, for instance prior to disconnecting the patient from the photopheresis system.

A number of different claim sets are set forth below. Each claim set may be used in combination with one or more of the other claim sets. A photopheresis system of the above-noted type may incorporate the features from these claims and in any appropriate combination.

It should be appreciated that although this disclosure addresses what is commonly referred to as a "dual needle configuration" (where blood is withdrawn from a patient at one location (e.g., one arm) and using an appropriate patient access, and returned to the patent at another location (e.g., the other arm) and using an appropriate patient access), the various features addressed herein are equally applicable to what is commonly referred to as a "single needle configuration" (where blood is withdrawn from a patient, and then returned to the patient, using a single patient access).

A first aspect of the present invention is embodied by a method of operating a blood processing system (e.g., a photopheresis system that includes a photo-activation module that utilizes at least one light source; the blood processing system may be configured to execute the first aspect), where this blood processing system includes a deck and a disposable kit, where the deck includes a pressure transducer, where at least part of the kit is installed on the deck, where at least part of the kit includes a pressure dome that is positioned on a corresponding pressure transducer, and where the pressure dome includes a flow chamber, a first flow port for this flow chamber, and a second flow port for this flow chamber.

In the case of the first aspect, a first negative pressure test, a first positive pressure test, and a second negative pressure test are each conducted by the blood processing system in relation to the pressure dome, where the first positive pressure test is executed after the first negative pressure test, and where the second negative pressure test is also executed after the first negative pressure test. The first negative pressure test is directed to attempting to generate a first vacuum within the flow chamber by withdrawing fluid out of the flow chamber through either the first flow port or the second flow port. The first positive pressure test is directed to attempting to generate a first positive pressure within the flow chamber by directing fluid into the flow chamber through either the first flow port or the second flow port. The second negative pressure test is directed to attempting to generate a second vacuum within the flow chamber by withdrawing fluid out of the flow chamber through either the first flow port or the second flow port (e.g., the second vacuum (second negative pressure test) may be larger than the first vacuum (first negative pressure test)).

A number of feature refinements and additional features are applicable to the first aspect of the present invention. These feature refinements and additional features may be used individually or in any combination. The following discussion is applicable to at least the first aspect.

An installation of the pressure dome on a corresponding pressure transducer may be assessed by the blood processing system through execution of the first negative pressure test. In the event that the pressure dome does not pass the first negative pressure test, the pressure dome may be reinstalled on the pressure transducer, and the first negative pressure test may be repeated. The blood processing system may be configured such that the first positive pressure test and the second negative pressure test are executed by the blood processing only if the blood processing system determines that the pressure dome passed the first negative pressure test.

The blood processing system may include a display, and the blood processing system may then provide an indication on this display if the installation assessment of the pressure dome determines that the pressure dome failed to pass the first negative pressure test. The noted installation assessment by the blood processing system may include determining if a pressure within the flow chamber satisfies a first negative pressure threshold (e.g., in response to execution of the first negative pressure test). This may entail using an output of the pressure transducer during execution of the first negative pressure test. Satisfaction of the first negative pressure threshold may be characterized as: 1) the pressure within the flow chamber being between a first negative pressure and a second negative pressure (e.g., within a range of about −20 mmHG to about −40 mmHG); and/or 2) the pressure within the flow chamber being of at least a first predetermined amount of vacuum.

An operational range of the pressure transducer may be assessed using each of the first positive pressure test and the second negative pressure test (and which may be executed in any order relative to one another). The blood processing system may provide an indication on a display if the noted operational range assessment determines that the pressure dome failed to pass at least one of the first positive pressure test and the second negative pressure test. This operational range assessment by the blood processing system may include determining if a pressure within the flow chamber satisfies a first positive pressure threshold for the first positive pressure test. This may entail using an output of the pressure transducer during execution of the first positive pressure test. Satisfaction of the first positive pressure threshold may be characterized as: 1) the pressure within the flow chamber being between a first positive pressure and a second positive pressure; and/or 2) the pressure within the flow chamber being of at least a first predetermined amount (e.g., at least about 330 mmHG).

The noted operational range assessment may include determining if a pressure within the flow chamber satisfies a second negative pressure threshold (e.g., in response to execution of the second negative pressure test). This may entail using an output of the pressure transducer during execution of the second negative pressure test. Satisfaction of the second negative pressure threshold may be characterized as: 1) the pressure within the flow chamber being between a third negative pressure and a fourth negative pressure; and/or 2) the pressure within the flow chamber being of at least a second predetermined amount of vacuum (e.g., at a minimum vacuum level of −300 mmHG).

A second aspect of the present invention is embodied by a method of operating a blood processing system (e.g., a photopheresis system that includes a photo-activation module that utilizes at least one light source; the blood processing system may be configured to execute the second aspect), where this blood processing system includes a centrifuge or centrifuge bowl, and where this centrifuge includes first, second, and third ports. A first fluid is loaded into the centrifuge through the first port. A first purging operation is executed and entails pressurizing the centrifuge to a first pressure threshold (a first pressurization; e.g., at least 460 mmHG), rotating the centrifuge (e.g., at 400 RPM), and directing air out of the centrifuge through the third port after completion of the first pressurization (e.g., air may be directed out of the centrifuge through the third port for the first purging operation after rotation of the centrifuge has been terminated). A second purging operation is executed after completion of the first purging operation, with the centrifuge being stationary, and entails pressurizing the centrifuge to a second pressure threshold (a second pressurization; e.g., at least 460 mmHG) and directing air out of the centrifuge through the second port after completion of this second pressurization. A third purging operation is executed after completion of the second purging operation, and entails pressurizing the centrifuge to a third pressure threshold (a third pressurization; e.g., at least 300 mmHG), rotating the centrifuge (e.g., after the third pressurization has been completed), and directing air out of the centrifuge through the second port after the third pressurization.

A number of feature refinements and additional features are applicable to the second aspect of the present invention. These feature refinements and additional features may be used individually or in any combination. The following discussion is applicable to at least the second aspect.

The first pressure threshold for the first purging operation may be the same as the second pressure threshold for the second purging operation. The third pressure threshold for the third purging operation may be less than the first pressure threshold for the first purging operation, and also may be less than the second pressure threshold for the second purging operation. One embodiment has the centrifuge being rotated at a larger or faster rotational speed for the third purging operation compared to the first purging operation (e.g., the rotational speed of the centrifuge for the third purging operation may be at least eight times greater than the rotational speed of the centrifuge for the first purging operation).

The blood processing system may include a first container that is fluidly connectable with the centrifuge. Air directed out of the centrifuge by each of the first purging operation, the second purging operation, and the third purging operation may be transferred to this first container. One embodiment has this first container being in the form of a return bag. This return bag may be incorporated by a disposable kit that is used by the blood processing system.

The second port of the centrifuge and the third port of the centrifuge may be vertically spaced from/relative to one another. An entrance to the third port in relation to fluid exiting the centrifuge through the third port may be at a bottom portion of a fluid containing volume of the centrifuge. An entrance to the second port in relation to fluid exiting the centrifuge through the second port may be at a top portion of this same fluid-containing volume of the centrifuge.

The centrifuge may rotate about a rotational axis for purposes of each of the first purging operation and the third purging operation. One embodiment has the second port and the third port of the centrifuge being spaced from one another in a dimension that corresponds with this rotational axis for the centrifuge. A length dimension of a fluid-containing volume of the centrifuge may be measured along the rotational axis of the centrifuge. An entrance to the third port (in relation to fluid exiting the centrifuge through the third port) and an entrance to the second port (in relation to fluid exiting the centrifuge through the second port) may be spaced from one another along an axis that is parallel to the rotational axis, and where the third port and second sport are separated by a distance along this axis that is at least about 90% of a length of the fluid-containing volume of the centrifuge.

A third aspect of the present invention is embodied by a method of operating a blood processing system (e.g., a photopheresis system that includes a photo-activation module that utilizes at least one light source; the blood processing system may be configured to execute the second aspect), where this blood processing system includes a centrifuge or centrifuge bowl, and where this centrifuge includes first and second ports. Blood is introduced into the centrifuge through the first port and is separated into a plasma layer, a buffy coat layer, and a red blood cell layer within the centrifuge and in response to/based upon rotation of the centrifuge. A location of an interface between the buffy coat layer and the red blood cell layer (within the centrifuge) is monitored.

The blood processing system monitors for the existence of a first condition and a second condition in the case of the third aspect. The first condition exists when: 1) the amount of blood that has been introduced into the centrifuge is both less than a target processed blood volume and within a first predetermined amount of this target processed blood volume (e.g., 75 ml; the first predetermined amount may be a fixed amount that is independent of a magnitude of the target processed blood volume); and 2) the blood processing system determines that the interface between the buffy coat layer and the red blood cell layer is in a first position. The second condition exists when the amount of blood that has been introduced into the centrifuge is larger than the target processed blood volume by at least a second predetermined amount (e.g., 75 ml). A fluid flow is directed out of the second port of the centrifuge and into a first container, where this fluid flow includes buffy coat from the buffy coat layer. This "buffy coat collection" is initiated in response to the blood processing system having identified the existence of at least one of the first condition and the second condition.

A number of feature refinements and additional features are applicable to the third aspect of the present invention. These feature refinements and additional features may be used individually or in any combination. The following discussion is applicable to at least the third aspect. Initially, a fourth aspect of the invention that is addressed in more detail below may be used in combination with this third aspect.

A fourth aspect of the present invention is embodied by a method of operating a blood processing system that includes a centrifuge having first and second ports (e.g., a photopheresis system that includes a photo-activation module that utilizes at least one light source; the blood processing system may be configured to execute the fourth aspect). Blood is introduced into the centrifuge through the first port and is separated into a plasma layer, a buffy coat layer, and a red blood cell layer within the centrifuge and in response to/based upon rotation of the centrifuge. A fluid flow is directed out of the second port of the centrifuge and into a first container, and where this fluid flow includes buffy coat from the buffy coat layer. A hematocrit of an initial portion of this fluid flow out of the centrifuge through the second port is monitored, and a hematocrit offset value is determined therefrom. The fluid flow out of the second port of the centrifuge and into the first container is thereafter assessed using this hematocrit offset value.

A number of feature refinements and additional features are applicable to the fourth aspect of the present invention. These feature refinements and additional features may be used individually or in any combination. The following discussion is applicable to at least the fourth aspect.

The hematocrit offset value may be determined using an output of a hematocrit sensor that is associated with a fluid line, where this fluid line extends between the centrifuge (second port) and the first container. The initial portion of the fluid flow out of the centrifuge, which again is used to determine the hematocrit offset value, is the first fluid that is directed out of the centrifuge through the second port and into the first container (no other fluid is directed out of the centrifuge and into the first container prior to this initial portion). This initial portion of the fluid flow may include introducing a predetermined fluid amount into the first container (e.g., 10 ml).

The assessment of the fluid flow being directed into the first container may include comparing a current hematocrit value of the fluid flow to a hematocrit threshold, where this hematocrit threshold is an amount that corresponds to the sum of the hematocrit offset value and a predetermined percentage (e.g. 5%). The fluid flow into the first container may be suspended or terminated when the current hematocrit value of the fluid flow satisfies the hematocrit threshold. "Satisfaction" of the hematocrit threshold may be equated with a condition where the current hematocrit value is equal to or greater than the hematocrit threshold. After the fluid flow into the first container has been terminated, the contents of the first container may be subjected to phototherapy.

The fourth aspect may be used in conjunction with a blood prime operation where donor blood is introduced into the centrifuge, followed by introducing patient blood into the centrifuge (where the blood prime operation utilizes the donor blood). This may be done by a user providing user input to the blood processing system (e.g., for activation of a blood prime function of the blood processing system). In any case, the blood processing system may include a return bag. The blood processing system may be configured to preclude transferring contents of the return bag back to the patient when the blood prime function has been activated. The contents of the first container may be photo-activated, and the blood processing system may be configured to preclude transferring contents of the return bag back to a patient at any time during this photo-activation, and when the blood prime function has been activated.

The blood processing system may receive user input regarding a desired rinseback volume (e.g., the user may input the desired rinseback volume to the blood processing system). In this case, the rinseback volume from the first container may be reinfused back to the patient, but only after termination of the above-noted photoactivation (and when the blood prime function has been activated).

A fifth aspect of the present invention is embodied by a method of operating a blood processing system that includes a centrifuge (e.g., a photopheresis system that includes a photo-activation module that utilizes at least one light source; the blood processing system may be configured to execute the fifth aspect). Blood (e.g., whole blood) is directed or introduced into the centrifuge and is separated into a plurality of blood components (e.g. plasma, buffy coat, red blood cells) within the centrifuge and in response to/based upon rotation of the centrifuge. All flows out of and into the centrifuge are terminated, and the rotational velocity of the centrifuge is reduced or terminated. Thereafter, a flow path out of the centrifuge is opened (e.g., corresponding with the desired blood component). Contraction of the centrifuge (in response to terminating the rotation of the centrifuge) is used to displace the desired blood component out of the centrifuge.

A sixth aspect of the present invention is embodied by a method of operating a blood processing system that includes a centrifuge (e.g., a photopheresis system that includes a photo-activation module that utilizes at least one light source; the blood processing system may be configured to execute the sixth aspect). A number of inputs are provided to the blood processing system, including a white blood cell target count and a white blood cell percentage in a patient's blood that is to be processed. The blood processing system calculates an amount of whole blood from this patient that will need to be processed in order to collect an amount of white blood cells that should correspond with the white blood cell target count. In this regard, blood (e.g., whole blood) from the noted patient is directed or introduced into the centrifuge and is separated into a plurality of blood components (e.g. plasma, buffy coat, red blood cells) within the centrifuge and in response to/based upon rotation of the centrifuge. White blood cells are collected (e.g., via buffy coat collection), namely removed from the centrifuge (e.g., and directed into a collection bag), for instance after the calculated amount of whole blood has been processed by the blood processing system.

A seventh aspect of the present invention is embodied by a method of operating a blood processing system that includes a centrifuge (e.g., a photopheresis system that includes a photo-activation module that utilizes at least one light source; the blood processing system may be configured to execute the seventh aspect). A patient is fluidly connected with the blood processing system by an access line (e.g., to withdraw blood from the patient; to return blood/blood components to the patient). A pressure in the access line is monitored by the blood processing system. In the event that the blood processing system determines that a pressure in the access line is within a predetermined amount of a corresponding pressure or alarm limit, the flowrate associated with this access line is reduced (e.g., by reducing the operational speed of a corresponding pump). If this in turn reduces the pressure within the access line by at least a certain amount, the flowrate associated with the access line is thereafter increased (e.g., by increasing the operational speed of the corresponding pump). In one embodiment, the flowrate in the access line may be repeatedly reduced by the same increment (e.g., 2 ml/minute) until the desired pressure reduction is achieved.

An eighth aspect of the present invention is embodied by a method of operating a blood processing system that includes a centrifuge (e.g., a photopheresis system that includes a photo-activation module that utilizes at least one light source; the blood processing system may be configured to execute the eighth aspect). Blood (e.g., whole blood) from a patient is directed or introduced into the centrifuge and is separated into a plurality of blood components (e.g. plasma, buffy coat, red blood cells) within the centrifuge and in response to/based upon rotation of the centrifuge. A location of an interface between a buffy coat layer and a red blood cell layer (within the centrifuge) is monitored by the blood processing system. After a predetermined amount of blood has been processed (e.g., at least 450 ml), the current location of the interface between the buffy coat layer and the red blood cell layer within the centrifuge is compared with an interface threshold (e.g., stored by the blood processing system). If the current location of the interface between the buffy coat layer and the red blood cell layer within the centrifuge does not satisfy the interface threshold (e.g., if the current location is not within a predetermined range), an alarm of any appropriate type may be activated (e.g., to indicate the existence of an anemic patient).

A ninth aspect of the present invention is embodied by a method of operating a blood processing system that includes a centrifuge (e.g., a photopheresis system that includes a photo-activation module that utilizes at least one light source; the blood processing system may be configured to execute the ninth aspect). Blood (e.g., whole blood) from a patient is directed or introduced into the centrifuge and is separated into a plurality of blood components (e.g. plasma, buffy coat, red blood cells) within the centrifuge and in response to/based upon rotation of the centrifuge. One or more blood components are directed out of the centrifuge and into a return bag. The flow of blood from the patient to the centrifuge is suspended, and contents of the return bag are directed back into the centrifuge. Thereafter, the flow of blood from the patient to the centrifuge may be re-initiated. Once a targeted amount of blood has been processed, a blood component (e.g., buffy coat) may be directed out of the centrifuge and into a collection bag or the like.

BRIEF DESCRIPTION OF THE FIGURES

FIG. 3B is another embodiment of a protocol for purging air bubbles out of a centrifuge bowl of a photopheresis kit of the type shown in FIGS. 1A and 2C.

FIG. 7 is an embodiment of a protocol that uses elasticity and centrifugal force to displace fluid (e.g., buffy coat) from a centrifuge bowl of a photopheresis kit that is at least generally of the type shown in FIGS. 1A and 2C.

FIG. 8 (sheets 8/1 and 8/2) is an embodiment of a buffy coat collection protocol for a photopheresis system.

FIG. 10 is an embodiment of a protocol that may be used by a photopheresis system for resetting fluid balance in the case of a blood prime.

DETAILED DESCRIPTION

Photopheresis or extracorporeal photopheresis (ECP) is a photoimmune therapy where white blood cells are separated from whole blood via apheresis, combined with a photoactive drug (such as 8-methoxypsoralen), and exposed to Ultraviolet A (UVA) light. All blood components, including the treated white blood cells, are returned to the patient.

A photopheresis system, such as the CellEx® Photopheresis System, may be an integrated system that comprises the CellEx® Photopheresis instrument, the CellEx® Procedural Kit, and the CellEx® Light Assembly. The photopheresis system may collect white blood cells from a continuous flow, which is in contrast to discontinuous batching processes that require separation of small portions of whole blood and storing white blood cells while the next batch is separated. In the continuous process, whole blood, such as blood taken directly from a patient, may be separated in a centrifuge bowl, and red blood cells and plasma are pumped out of the bowl and returned to the patient.

Meanwhile, the buffy coat (leukocyte-enriched blood) is collected from the continuous flow and passed through a photoactivation module, where a drug is activated with a precise amount of UVA light. The amount of UVA light used may be determined by the characteristics of the individual patient's buffy coat. The photoactivation module may also expose the buffy coat to UVADEX Sterile Solution (8 MOP), which, when combined with the UVA light, may result in apoptosis of the white blood cells. Once the photoactivation is complete, the buffy coat may be returned promptly to the patient's bloodstream. Reinfusing the photoactivated white blood cells into a patient may stimulate the patient's immune system to fight cutaneous T-cell lymphoma (CTCL), graft versus host disease (GVHD), Rheumatoid Arthritis, Progressive Systematic Sclerosis, Juvenile Onset Diabetes, Inflammatory Bowel Disease and other immune-oncologic, transplant immunologic, and inflammatory, other immunologic diseases thought to be T-cell or White Blood Cell Mediated including cancer.

In some embodiments, red blood cells and plasma may be returned to the patient simultaneously with the whole blood being drawn from the patient. This may be achieved by using a double needle mode, where one needle is used for collection of whole blood and the other needle is used to return the cells to the patient. In other embodiments, a single needle mode may be used, wherein blood is drawn and the cells and plasma are returned intermittently. Either way, the continuous process, including cell separation and photoactivation, occurs within a single, closed, sterile circuit and reduces the extracorporeal volume deficit. This may result in a reduced potential for infection and ensures that a patient's autologous cells are returned to them.

Figure 1A:
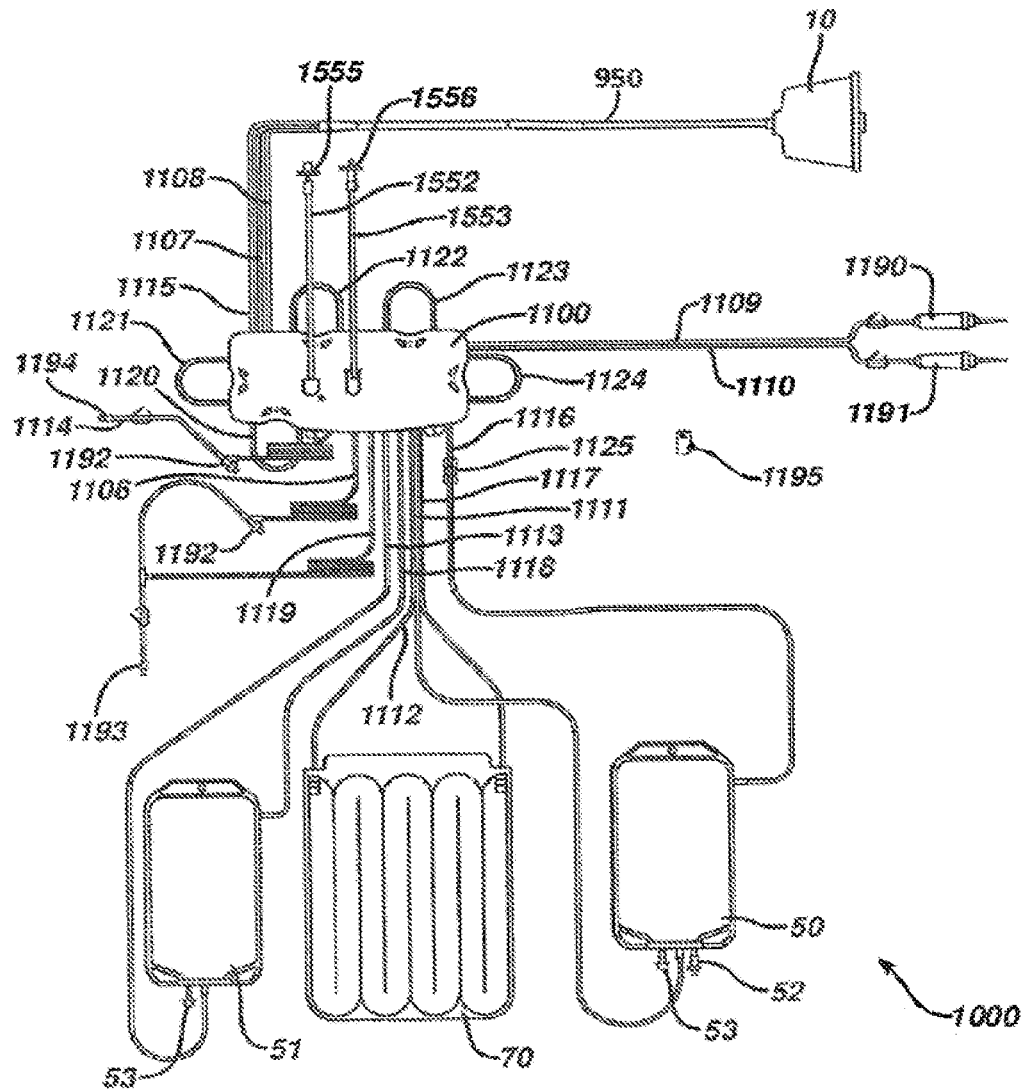
FIG. 1A is a schematic representation of an embodiment of a disposable kit used for photopheresis therapy.
Figure 1B:
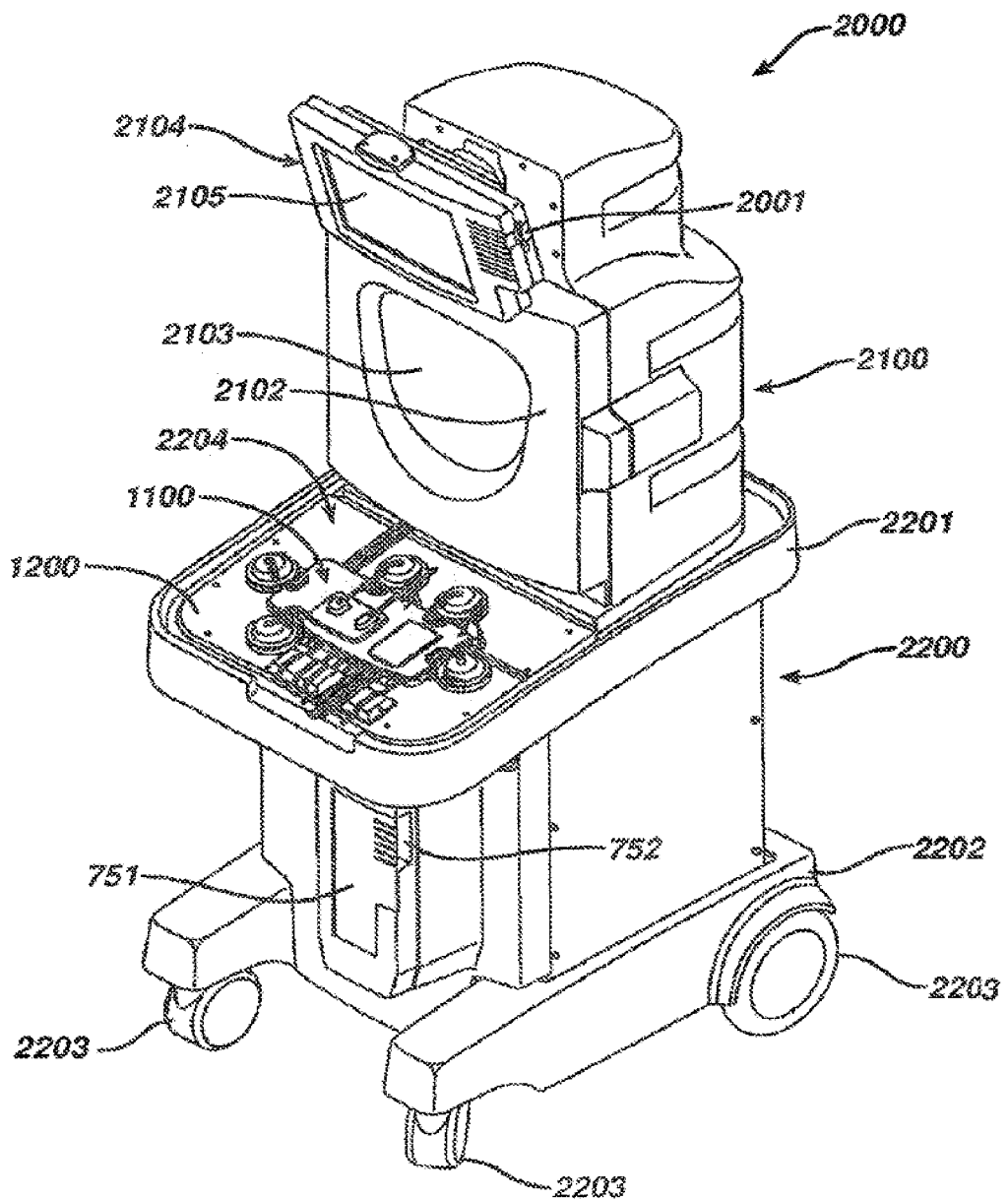
FIG. 1B is an elevated perspective view of an embodiment of a permanent tower system or photopheresis cabinet for use in conjunction with a disposable kit for facilitating a photopheresis therapy session.

In some embodiments, a disposable photopheresis kit (e.g., as described in US Patent Publication No. 2010/0298752) may be used. FIG. 1A illustrates a disposable photopheresis kit 1000. It is necessary that a new disposable, sterile photopheresis kit be used for each therapy session. In order to facilitate the circulation of fluids through photopheresis kit 1000, and to treat blood fluids circulating therethrough, photopheresis kit 1000 is installed on a permanent tower system 2000 (FIG. 1B). The installation of photopheresis kit 1000 onto tower system 2000 is described in more detail below, as well as in US Patent Publication No. 2010/0298752 (the entire disclosure of which is being incorporated by reference).

Photopheresis kit 1000 includes cassette 1100, centrifuge bowl 10, irradiation chamber 70, hematocrit sensor 1125, removable data card 1195, treatment bag 50, and plasma collection or return bag 51. Photopheresis kit 1000 further includes saline connector spike 1190 and anticoagulant connector spike 1191 for respectively connecting saline and anticoagulant fluid bags (not shown). Photopheresis kit 1000 has all the necessary tubing and connectors to fluidly connect all devices and to route the circulation of fluids during a photopheresis treatment session. All tubing is sterile medical grade flexible tubing. Triport connectors 1192 are provided at various positions for the introduction of fluids into the tubing if necessary.

Needle adapters 1193 and 1194 are provided for respectively connecting photopheresis kit 1000 to needles for drawing whole blood from a patient and returning blood fluids to the patient. Alternatively, photopheresis kit 1000 can be adapted to use a single needle to both draw whole blood from the patient and return blood fluids to the patient. In some embodiments, a two needle kit may be used because it allows whole blood to be drawn and blood fluids to be returned to the patient simultaneously. When a patient is hooked up to photopheresis kit 1000, a closed loop system is formed.

Cassette 1100 acts both as a tube organizer and a fluid flow router. Irradiation chamber 70 is used to expose blood fluids to UV light. Centrifuge bowl 10 separates whole blood into its different components according to density. Treatment bag 50 is a 1000 mL three port bag. Straight bond port 52 is used to inject a photoactivatable or photosensitive compound into treatment bag 50. Plasma collection bag 51 is a 1000 mL two port bag. Both treatment bag 50 and plasma collection bag 51 have a hinged cap spike tube 53 which can be used for drainage if necessary. Photopheresis kit 1000 further includes hydrophobic filters 1555 and 1556 which are adapted to connect to pressure transducers 1550 and 1551 to filter 1500 via vent tubes 1552 and 1553 for monitoring and controlling the pressures within tubes connecting the patient (as described in FIG. 10 of US Patent Publication No. 2010/0298752). Monitoring the pressure helps ensure that photopheresis kit 1000 is operating within safe pressure limits. The individual devices of photopheresis kit 1000, and their functioning, are discussed in more detail in US Patent Publication No. 2010/0298752.

Photopheresis kit 1000 may be installed in permanent tower system or photopheresis cabinet 2000, as shown in FIG. 1B. Tower system 2000 is the permanent (i.e., non-disposable) piece of hardware that receives the various devices of photopheresis kit 1000, such as, cassette 1100, irradiation chamber 70, and centrifuge bowl 10 (FIG. 1A). Tower system 2000 performs the valving, pumping, and overall control and drive of fluid flow through disposable photopheresis kit 1000. Tower system 2000 performs all of the necessary control function automatically through the use of a properly programmed controller, for example a processor or IC circuit, coupled to all of the necessary components. While a new disposable kit 1000 must be discarded after each photopheresis therapy session, tower system 2000 is used over and over again. Tower system 2000 can be modified to perform a number of extracorporeal blood circuit treatments, for example apheresis, by properly programming the controller or by changing some of its components.

Tower system 2000 has a housing having an upper portion 2100 and a base portion 2200. Base portion 2200 has a top 2201 and a bottom 2202. Wheels 2203 are provided at or near the bottom 2202 of base portion 2200 so that tower system 2000 is mobile and can easily be moved from room to room in a hospital setting. Preferably, the front wheels 2203 are pivotable about a vertical axis to allow ease in steering and maneuvering tower system 2000. Top 2201 of base portion 2200 has a top surface 2204 having control deck 1200 built therein (see FIG. 22 of US Patent Publication No. 2010/0298752). In FIG. 2, cassette 1100 is loaded onto control deck 1200. Base portion 2200 also has hooks (not illustrated), or other connectors, to hang plasma collection bag 51 and treatment bag 50 therefrom. Such hooks can be located anywhere on tower system 2000 so long as their positioning does not interfere with the functioning of the system during therapy. Base portion 2200 has photoactivation chamber 750 (see FIG. 18 of US Patent Publication No. 2010/0298752) located behind door 751. Additional hooks (not illustrated) are provided on tower system 2000 for hanging saline and anticoagulant bags. Preferably, these hooks are located on upper portion 2100.

Photoactivation chamber 750 (see FIG. 18 of US Patent Publication No. 2010/0298752) is provided in base portion 2200 of tower system 2000 between top 2201 and bottom 2202 behind door 751. Door 751 is hingedly connected to base portion 2200 and is provided for access to photoactivation chamber 750 and to allow the operator to close photoactivation chamber 750 so the UV light does not escape into the surrounding during treatment. Recess 752 is provided to allow tubes 1112, 1117 (see FIG. 1) to pass into photoactivation chamber 750 when irradiation chamber 70 is loaded and when door 751 is closed. The photoactivation chamber is discussed in detail with respect to FIGS. 16 and 18 of US Patent Publication No. 2010/0298752.

Upper portion 2100 is located atop base portion 2200. Centrifuge chamber 2101 (see FIG. 19 of US Patent Publication No. 2010/0298752) is located in upper portion 2100 behind centrifuge chamber door 2102. Centrifuge chamber door 2102 has a window 2103 so an operator can see in centrifuge chamber 2101 and monitor for any problems. Window 2103 is constructed with glass thick enough to withstand any forces that may be exerted on it from an accident during centrifugation which can rotate the centrifuge bowl at speeds greater than 4800 RPMs. Preferably, window 2103 is constructed of shatter-proof glass. Door 2102 is hingedly connected to upper portion 2100 and has an automatic locking mechanism that is activated by the system controller during system operation. Centrifuge chamber 2101 is discussed in more detail with respect to FIG. 19 of US Patent Publication No. 2010/0298752.

Preferably, deck 1200 is located on top surface 2204 of base portion 2200 at or near the front of system tower 2000 while upper portion 2100 is extending upward from base portion 2200 near the rear of tower system 2000. This allows the operator easy access to control deck 1200 while simultaneously affording the operator access to centrifuge chamber 2101. By designing tower system 2000 to have the centrifuge chamber 2101 in the upper portion 2100 and having the photoactivation chamber 750 and deck 1200 in base portion 2200, an upright configuration is achieved. As such, system tower 2000 has a reduced footprint size and takes up a reduced amount of valuable hospital floor space. The height of system tower 2000 remains below sixty inches so that one view is not obstructed when transporting the machine around the hospital from the rear. Additionally, having deck 1200 in a fairly horizontal position will provide the operator with a place to set devices of photopheresis kit 1000 during the loading of other devices, facilitating easy loading. Tower system 2000 is robust enough to withstand forces and vibrations brought on by the centrifugation process.

A monitor 2104 is provided on centrifuge chamber door 2102 above window 2103. Monitor 2104 has a display area 2105 for visually displaying data to an operator, such as, for example, user interfaces for data entry, loading instructions, graphics, warnings, alerts, therapy data, or therapy progress. Monitor 2104 is coupled to and controlled by the system controller. A data card receiving port 2001 is provided on a side of monitor 2104. Data card receiving port 2001 is provided to slidably receive data card 1195 which is supplied with each disposable photopheresis kit 1000 (FIG. 1A). As mentioned above, data card 1195 can be pre-programmed to store a variety of data to supply to the system controller of tower system 2000. For example, data card 1195 can be programmed to relay information so that the system controller can ensure: (1) that the disposable photopheresis kit is compatible with the blood drive equipment into which it is being loaded; (2) that the photopheresis kit is capable of running the desired treatment process; (3) that the disposable photopheresis kit is of a certain brand name or make. Data card receiving port 2001 has the necessary hardware and circuitry to both read data from, and write data to, data card 1195. Preferably, data card receiving port 2201 will record treatment therapy data to data card 1195. Such information can include for example, collection times, collection volumes, treatment times, volumetric flow rates, any alarms, malfunctions, disturbances in the process, or any other desired data. While data card receiving port 2001 is provided on monitor 2104, it can be located anywhere on tower system 2000 so long as it is coupled to the system controller or other appropriate control means.

Figure 1C:
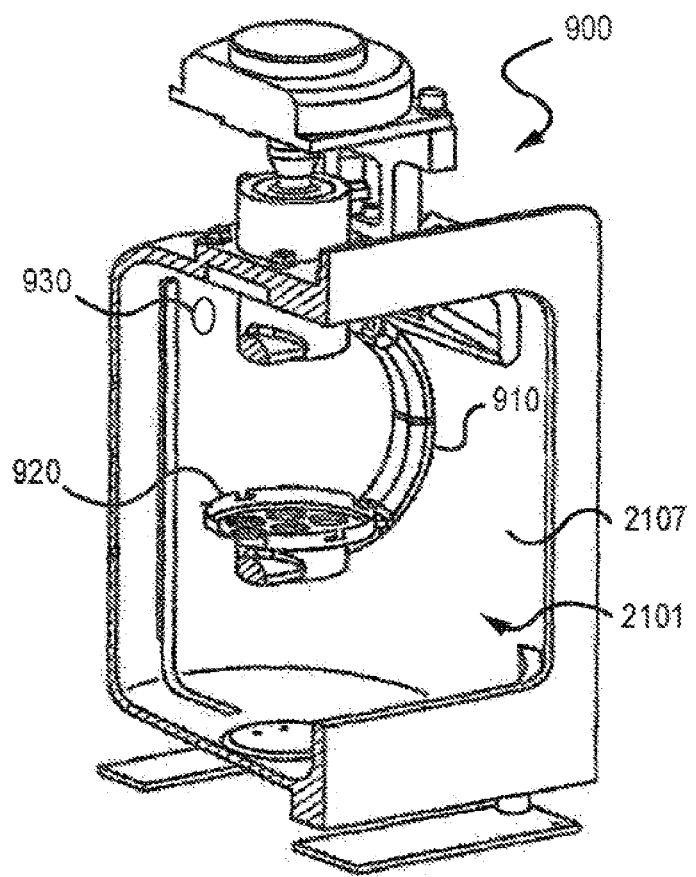
FIG. 1C is a cross-sectional view of a centrifuge chamber used by the photopheresis cabinet shown in FIG. 1B.
Figure 1D:
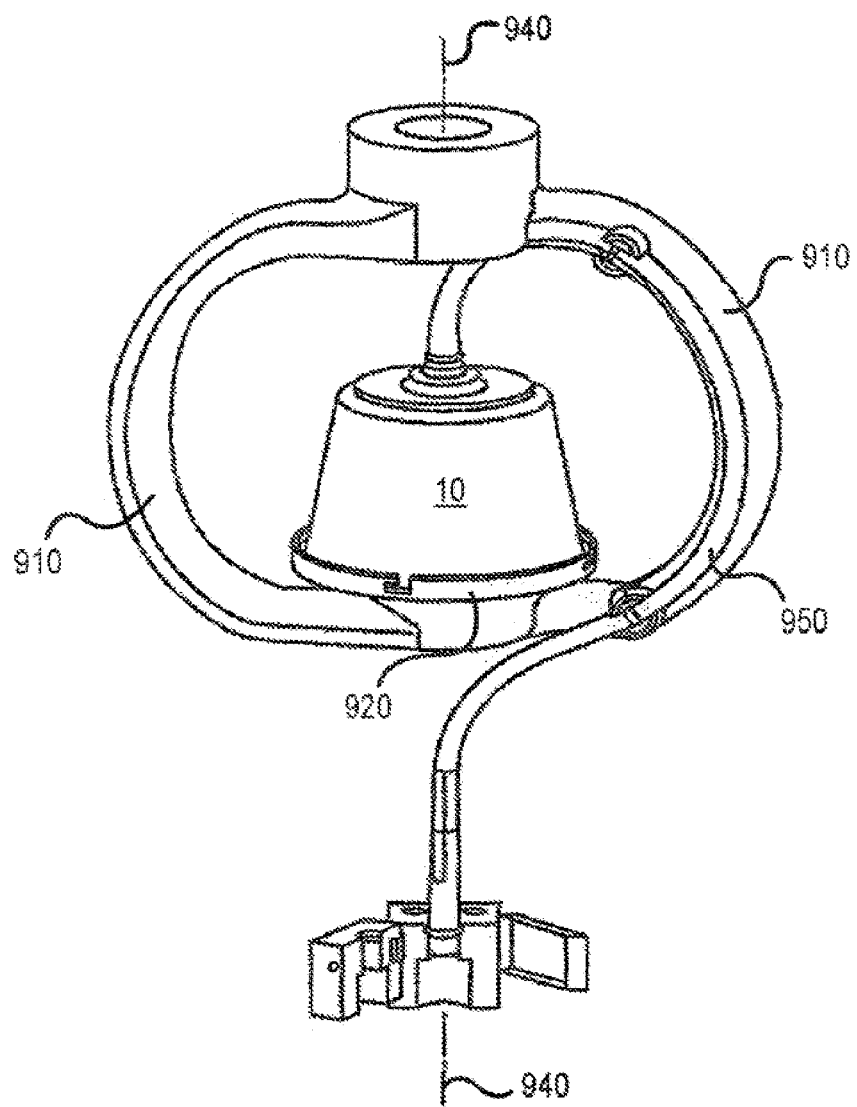
FIG. 1D is a perspective view of a centrifuge bowl and rotating frame used by the photopheresis cabinet of FIG. 1B.

Certain details regarding the incorporation of the centrifuge bowl 10 (FIG. 1A) with the tower system 2000 (FIG. 1B) are illustrated in FIGS. 1C and 1D. FIG. 1C illustrates the centrifuge chamber 2101 of the tower system 2000 in cross section and with the lower housing of tower system 2000 having been removed. The centrifuge chamber 2101 is located within a casting or outer housing 2107. A rotational drive 900 (also shown in cross section) is used by the tower system 2000 to rotate the centrifuge bowl 10 (FIGS. 1A and 1D) about an axis 940 and when appropriately positioned in the centrifuge chamber 2101. The rotational drive 900 may be of any appropriate type/configuration, for instance one capable of utilizing 1-omega 2-omega spin technology, or such as described in U.S. Pat. No. 3,986,442 (the entire disclosure of which is incorporated by reference herein).

A bracket or frame 910 and a bowl holding plate 920 are both disposed within the centrifuge chamber 2101 and are rotated by the rotational drive 900. The lower portion of the centrifuge bowl 10 is disposed within and is detachably secured to the bowl holding plate 920. A conduit 950 extends out of the upper portion of the centrifuge bowl 10, is secured to and rotates with the frame 910, and extends through the lower portion of the housing 2107 and then out of the centrifuge chamber 2101. Certain lines or tubes of the disposable photopheresis kit 1000 are disposed within this conduit 950 (the above-noted tube 1115 (for directing whole blood into the centrifuge bowl 10); the above-noted tube 1107 (for directing a lower density blood component, such as plasma and buffy coat, out of the centrifuge bowl 10); and the above-noted tube 1108 (for directing a higher density blood component, such as red blood cells, out of the centrifuge bowl 10)). The rotational drive 900 rotates the frame 910 and the bowl holding plate 920, which in turn rotates the centrifuge bowl 10 relative to the housing 2107 for the centrifuge chamber 2101. Rotation of the centrifuge bowl 10 separates whole blood (within the centrifuge bowl 10) into a plurality of blood components within the centrifuge bowl 10, for instance plasma, buffy coat, and red blood cells.

A bowl optic sensor 930 (BOS 930) is disposed within the centrifuge chamber 2101 (e.g., mounted to the housing 2107 for the centrifuge chamber 2101) to monitor the interface between the buffy coat and the red blood cells within the centrifuge bowl 10 as will be discussed in more detail below. Generally, the BOS 930 transmits an optical signal to a certain location of the centrifuge bowl 10 which should typically coincide with the interface between the buffy coat and the red blood cells after a certain volume of whole blood has been processed in the centrifuge bowl 10. When the interface between the buffy coat and the red blood cells is at this location, the signal that is output by the BOS 930 should be of a certain value (or within a range of values)—a BOS threshold. When the interface between the buffy coat and the red blood cells is located radially outward from the desired location within the centrifuge bowl 10 (i.e., the interface is spaced further from the rotational axis 940), the output signal from the BOS 930 may be larger than the BOS threshold. When the interface between the buffy coat and the red blood cells is located radially inward from the desired location within the centrifuge bowl 10 (i.e., the interface is spaced closer to the rotational axis 940), the output signal from the BOS 930 may be smaller than the BOS threshold.

Figure 2A:
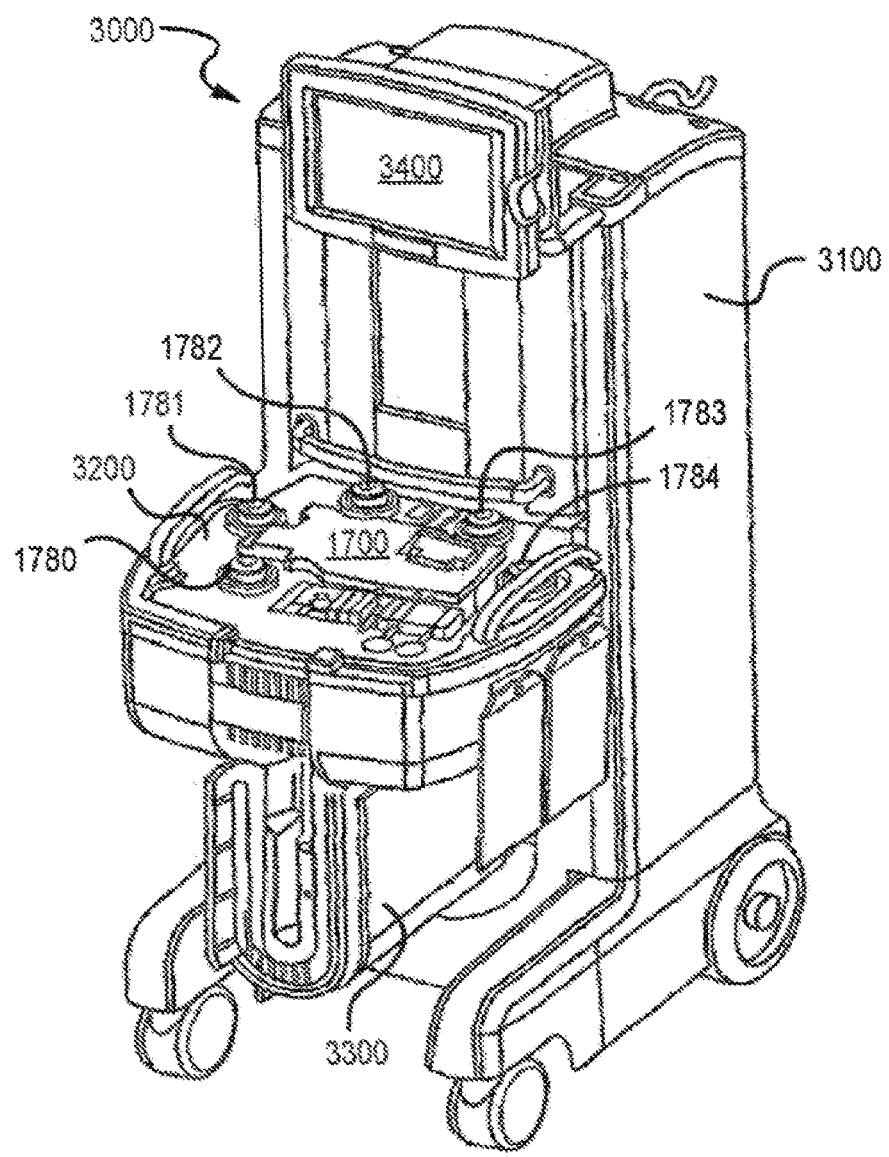
FIG. 2A is a perspective view of another embodiment of a tower system or photopheresis cabinet for use in conjunction with a disposable kit for conducting a photopheresis therapy session.

FIG. 2A illustrates another embodiment of a photopheresis system 3000. Primary components of the photopheresis system 3000 include a photopheresis tower or cabinet 3100 and a disposable kit 1900 (FIG. 2C), each of which are described in more detail in U.S. Pat. No. 7,476,209 (the entire disclosure of which is incorporated by reference). The photopheresis cabinet 3100 includes a deck 3200 to which a portion of the disposable kit 1900 (FIG. 2C) is secured, and that also incorporates the following pumps (e.g., peristaltic): recirculation pump 1780; anticoagulant pump 1781; whole blood or collect pump 1782; red blood cell or RBC pump 1783; and return pump 1784. Also positioned on the deck 3200 are pressure transducers 1754, 1755, and 1756 (FIG. 2B) and that will be discussed in more detail below. The photopheresis cabinet 3100 also includes a photo-activation module 3300 and a monitor or display 3400.

Figure 2B:
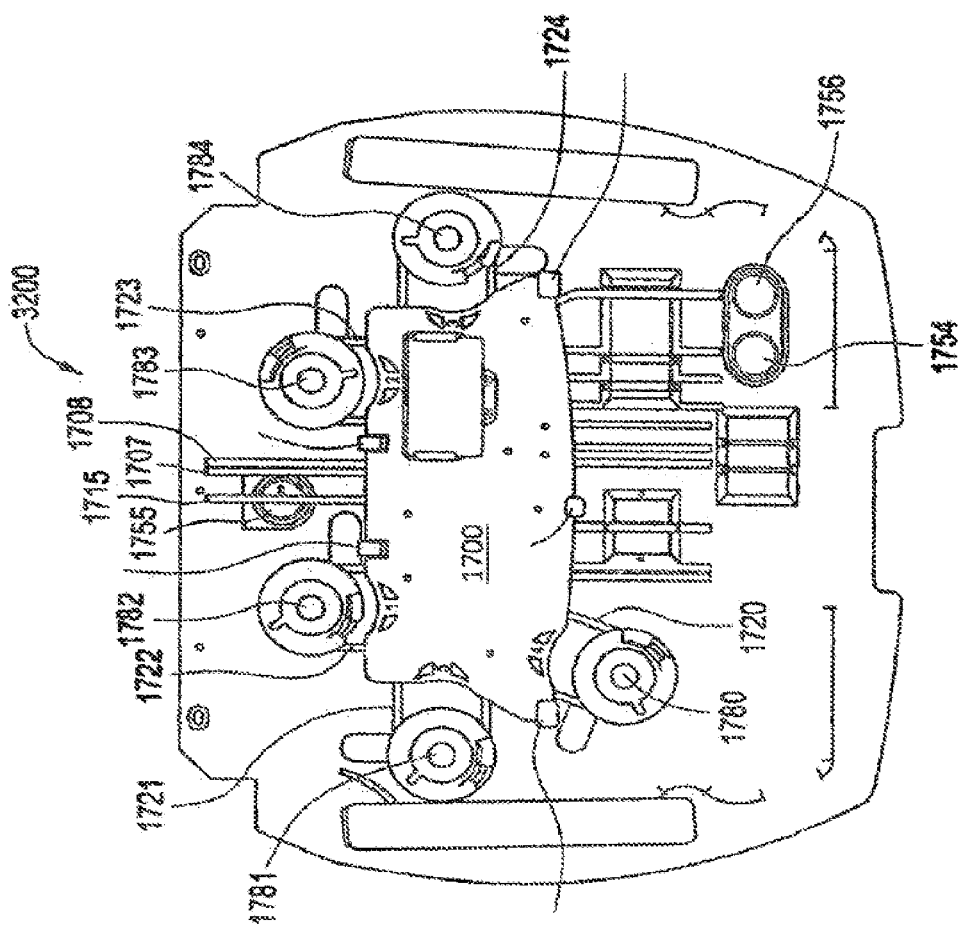
FIG. 2B is an enlarged view of a deck used by the photopheresis cabinet of FIG. 2A.
Figure 2C:
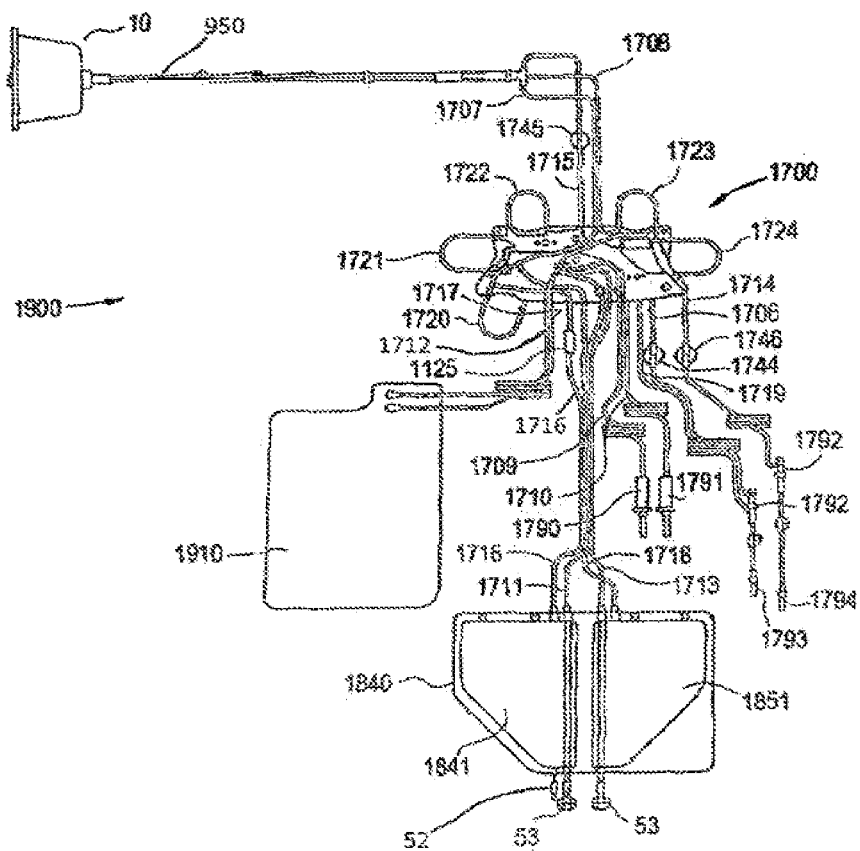
FIG. 2C is a schematic of another embodiment of a disposable photopheresis kit that may be used by the photopheresis cabinet of FIG. 2A.
Figure 2D:
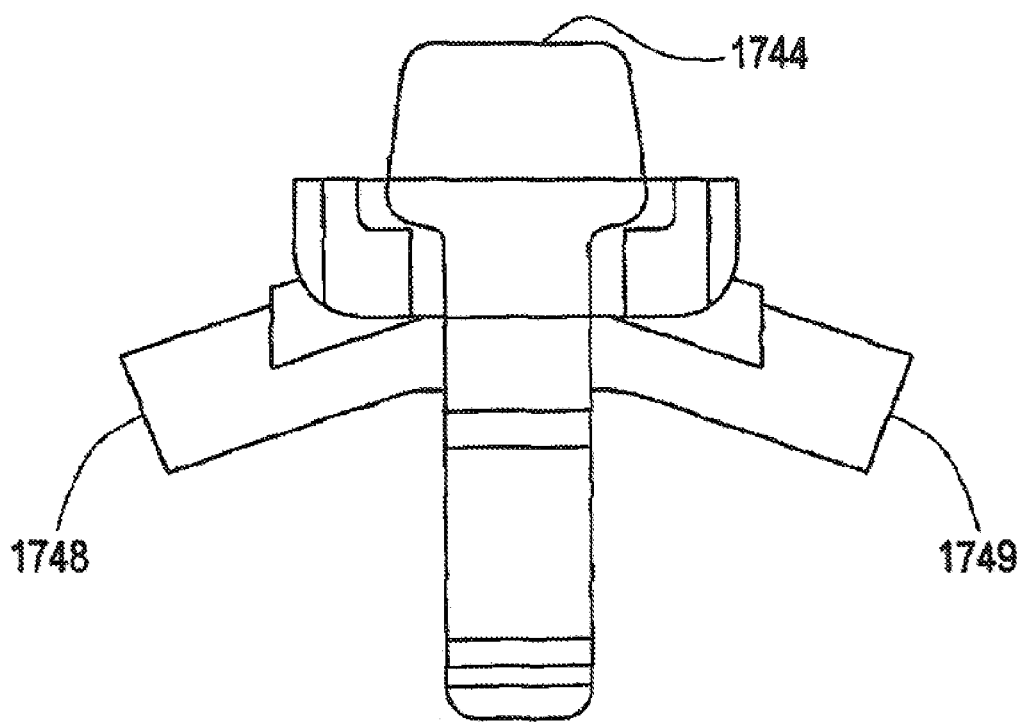
FIG. 2D is a side view of an embodiment of a pressure dome that may be used by the photopheresis kit of FIG. 2C.

Details regarding the above-noted disposable photopheresis kit 1900 are illustrated in FIG. 2C. A new (e.g., sterile) disposable photopheresis kit 1900 may be installed on the photopheresis cabinet 3100 (FIG. 2A) for the extracorporeal photopheresis treatment of blood fluids, preferably the buffy coat component of blood. The photopheresis kit 1900 includes a cassette 1700, centrifuge bowl 10, irradiation chamber 1910, hematocrit sensor 1125, pressure domes 1744, 1745, and 1746, and a dual chamber bag 1840 having a treatment chamber 1841, and plasma collection or return chamber 1851. A separate treatment bag 1841 and a separate plasma or return bag 1851 could be utilized as well (e.g., where the bags 1841 and 1851 could be disposed in spaced relation to one another). The cassette 1700 may be secured to the deck 3200 of the photopheresis cabinet 3100 by a snap-fit or snap-lock connection (or by other methods known in the art). The cassette 1700 may have a unique identifier that can function similar to the data card 1195 of the cassette 1100 discussed above.

The photopheresis kit 1900 further includes a saline connector spike 1790 and anticoagulant connector spike 1791 for respectively connecting saline and anticoagulant fluid bags (not shown). Needle adapters 1793 and 1794 are preferably provided for respectively connecting the photopheresis kit 1900 to needles for drawing whole blood from a patient and returning blood fluids to the patient. Alternatively, the photopheresis kit 1900 can be adapted to use a single needle to both draw whole blood from the patient and return blood fluids to the patient. In any case and when a patient is hooked up to the photopheresis kit 1900, a closed loop system is formed. That is, the photopheresis kit 1900 has all the necessary tubing and connectors to fluidly connect all devices and to route the circulation of fluids during a photopheresis treatment session. All tubing is preferably sterile medical grade flexible tubing. One or more multiport connectors 1792 may also be provided at various positions for the introduction of fluids into the tubing, as desired/necessary.

The photopheresis kit 1900 incorporates three pressure domes 1744, 1745, and 1746 for measurement of fluid pressures in selecting tubes/tubing sections/flow lines. Each pressure dome may be made of a biocompatible material (e.g., a polycarbonate plastic), and may include a housing produced by a one-piece plastic injection molding. A representative pressure dome is pressure dome 1744, that transmits a pressure signal via a flexible diaphragm or membrane (not shown) that is in fluid communication with the fluid inside tubing via an inlet port 1748 and an outlet port 1749 (FIG. 2D) to a corresponding pressure sensor (e.g., pressure transducer 1754 shown in FIG. 2B). The flexible diaphragm is preferably made of a silicone material or some other suitable biocompatible material. The flexible silicone dome diaphragm applies a pressure to a corresponding pressure sensor (e.g., piezoresistive transducer, 1754, 1755, and 1756) located on the deck 3200 of the photopheresis cabinet 3100 (FIG. 2A). Examples of a pressure dome and a pressure transducer are the SP844 Physiological Pressure Transducer and the Domes manufactured by MEMSCAP. Other configurations of pressure domes and/or pressure transducers may be utilized.

Figure 2E:
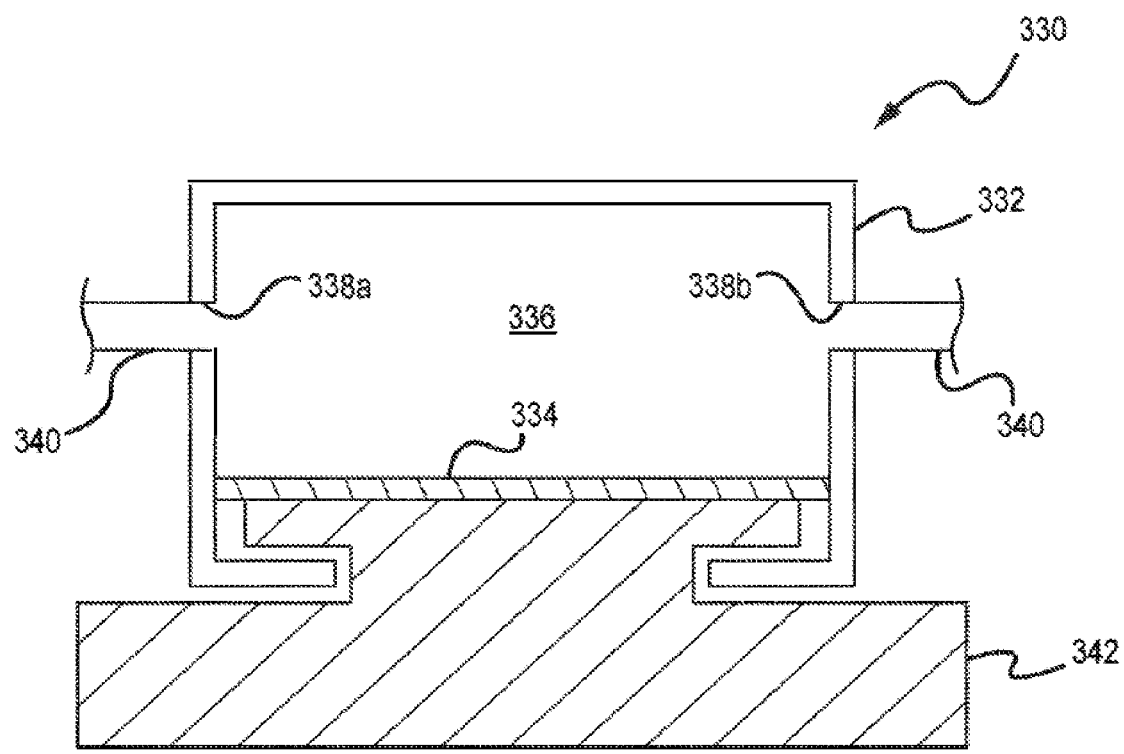
FIG. 2E is a cross-sectional schematic view of a pressure dome that may be used by the photopheresis kit of FIG. 2C.

A schematic that represents the principles of the above-noted pressure domes for the photopheresis kit 1900 is presented in FIG. 2E. The pressure dome 330 includes a housing 332 that defines an internal flow chamber 336. A flow line or tubing 340 accesses this flow chamber 336 by an inlet port 338*a* and an outlet port 338*b*. A flexible diaphragm 334 is exposed to the fluid pressure within the flow chamber 336, and furthermore is seated on a pressure transducer 342. An increase in the fluid pressure within the flow chamber 336 will result in the diaphragm 334 exerting a corresponding increased pressure on the pressure transducer 342. Similarly, a decrease in the fluid pressure within the flow chamber 336 will result in the diaphragm 334 exerting a corresponding reduced pressure on the pressure transducer 342.

Referring back to FIG. 2C, the dual chamber bag 1840 of the photopheresis kit 1900 may include a 1900 mL four-port treatment chamber 1841 and a 1900 mL three-port plasma collection or return chamber 1851. Any appropriate volumes may be utilized for these chambers/bags. A straight bond port 52 may be used to inject a photoactivatable or photosensitive compound into treatment chamber 1841. Both the treatment chamber 1841 and plasma collection chamber 1851 may incorporate a hinged cap spike tube 53, and which can be used for drainage if desired or necessary.

The cassette 1700 has fluid inlet tubes 1706, 1707, 1708, 1709, 1710, 1711, and 1712 for receiving fluids into the cassette 1700, fluid outlet tubes 1714, 1715, 1716, 1717, 1718, and 1719 for expelling fluids from the cassette 1700, and fluid inlet/outlet tube 1713 that can be used for both introducing and expelling fluids into and out of the cassette 1700. These fluid input and output tubes fluidly couple the cassette 1700 to a patient being treated, as well as the various devices of the photopheresis kit 1900, such as the centrifuge bowl 10, irradiation chamber 1910, dual chamber bag 1725 and bags containing saline, anticoagulation fluid to form a closed-loop extracorporeal fluid circuit. Pump tube loops 1720, 1721, 1722, 1723, and 1724, protrude from a side wall of the cassette 1700, and are provided for facilitating the circulation of fluids throughout the photopheresis kit 1900 during therapy. This side wall has openings for tube loops extending inside the cassette 1700, as well as openings for tube loops extending onto a bottom surface of a base of the cassette 1700. As such, when the cassette 1700 is secured to the deck 3200 of the photopheresis cabinet 3100 for a photopheresis procedure, each one of the pump tube loops 1720, 1721, 1722, 1723, and 1724 will be loaded into a corresponding peristaltic pump 1780, 1781, 1782, 1783, and 1784 (FIGS. 2A and 2B). The peristaltic pumps 1780, 1781, 1782, 1783, and 1784 drive fluid through the respective pump tube loops 1720, 1721, 1722, 1723, and 1724 in a predetermined direction, and thereby drive fluid through the photopheresis kit 1900 in a desired manner. More specifically: the pump tube loop 1722 loads into whole blood pump or collection 1782 and respectively drives whole blood in and out of the cassette 1700 via the inlet tube 1706 and outlet tube 1715; the pump loop tube 1724 loads into the return pump 1784 and drives blood fluids through a filter (incorporated by the cassette 1700—not shown, but similar to that described above) and back to the patient via the outlet tube 1714; the pump loop tube 1723 loads into the red blood cell pump 1783 and draws red blood cells from the centrifuge bowl 10 and drives them into the cassette 1700 via the inlet line 1708; the pump loop tube 1721 loads into the anticoagulant pump 1781 and drives an anticoagulant fluid into the cassette 1700 via the inlet tube 1710 and out of the cassette 1700 via outlet tube 1719, which connects with inlet tube 1706 through a multiport connector (not shown); and the pump loop tube 1720 loads into recirculation pump 1780 and drives blood fluids, such as plasma, through the treatment chamber 1841 of the dual chamber bag 1840 and the irradiation chamber 1910 from the cassette 1700.

Each of the peristaltic pumps 1780-1784 is activated when necessary to perform the photopheresis treatment therapy. The peristaltic pumps 1780-1784 can be operated one at a time or in any combination, and the pumps 1780-1784 may work in conjunction with compression actuators (not shown) to direct fluids through any desired pathways or combination thereof of photopheresis kit 1900. As noted and in one embodiment, the whole blood pump is 1782, the anticoagulant pump is 1781, the red blood cell pump is 1783, the recirculation pump is 1780, the return pump is 1784, the plasma chamber of dual chamber bag is 1851, the treatment chamber of dual chamber bag (TX) is 1841, and the irradiation chamber or plate is 1910.

In one embodiment, the circuitry of fluid inlet/outlet tubes, and pump tube loops in relation to the cassette 1700 may be in accordance with the following description. Anticoagulant inlet tube 1710 has fluid communication with anticoagulant outlet tube 1719 through pump tube loop 1721. Blood from a donor or patient comes through inlet tube 1706 that has fluid communication with outlet tube 1715 to the centrifuge bowl 10 through pump tube loop 1722. Outlet tube 1714 returns blood components back to a patient or donor. Saline inlet tube 1709 has fluid communication with plasma inlet tube 1713, treatment chamber inlet tube 1711, a T-connector (not shown), and irradiation chamber outlet tube 1717 by a five-way tube connector (not shown). The five-way tube connector is in fluid communication with the noted three way or T-connector, which in turn is in fluid communication with red blood cell pump tube loop 1723 and return pump tube loop 1724. Return pump tube loop 1724 for returning blood or blood components to a patient or donor carries the blood to a filter before the fluid exits the cassette 1700 via outlet tube 1714. The red blood cell pump tube loop 1723 has fluid communication with inlet tube 1708 from centrifuge bowl 10. Plasma and/or buffy coat entering cassette 1700 via inlet tube 1707 from centrifuge bowl 10 has fluid communication with plasma outlet tube 1718 through a T-connector (not shown). Pump tube loop 1720 for circulation of blood from the treatment chamber of the dual chamber bag to the irradiation chamber has fluid communication with inlet tube 1712 from the irradiation chamber 1841 and outlet tube 1716 to treatment chamber bag 1910 and inlet line 1707 from centrifuge bowl 10.

Figure 2F:
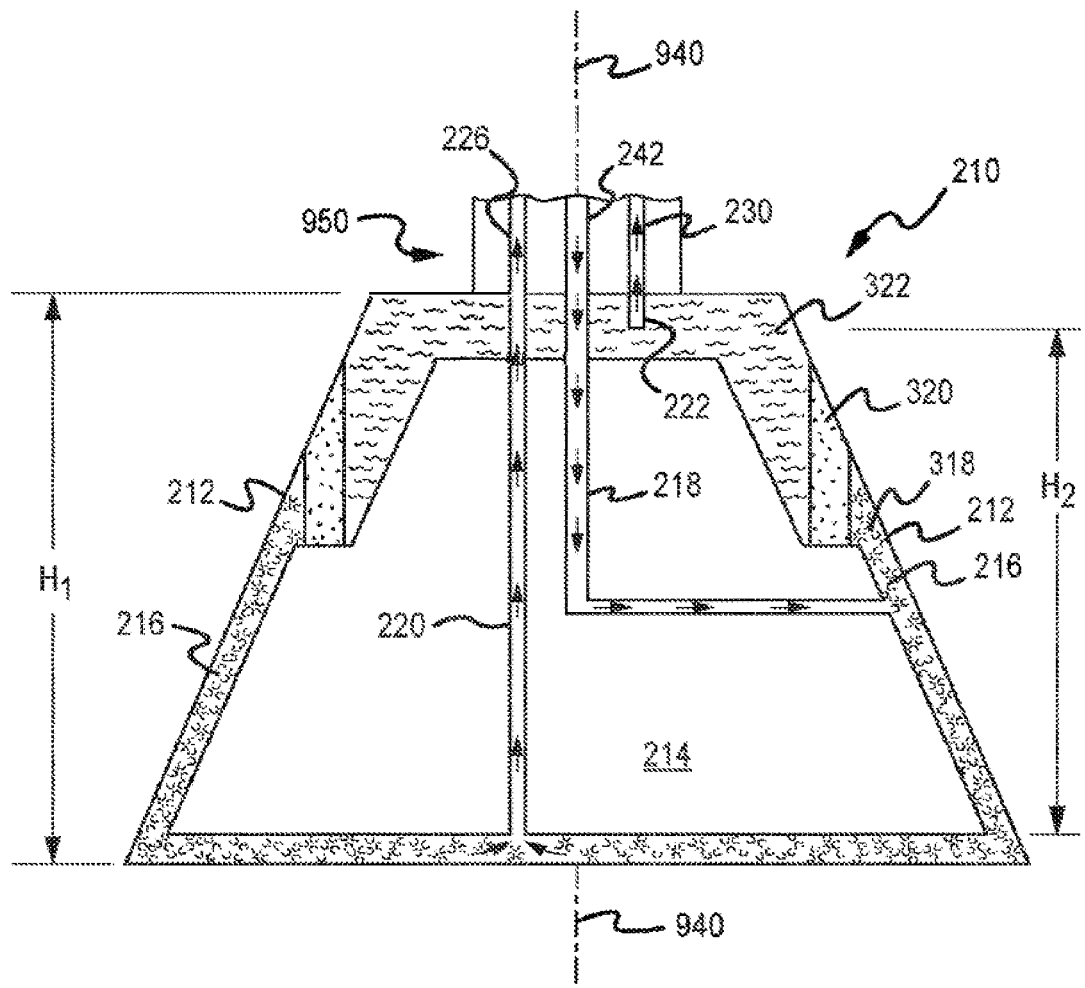
FIG. 2F is a cross-sectional schematic of a centrifuge bowl that may be used by the photopheresis kit of FIGS. 1A and 2C.

Each of the above-discussed disposable photopheresis kits 1000 (FIG. 1A), 1900 (FIG. 2C) incorporate a centrifuge bowl 10. A schematic that illustrates the basic principles of the centrifuge bowl 10 is presented in FIG. 2F. The centrifuge bowl 210 of FIG. 2F includes an outer housing 212 and an inner core 214 that are separated from one another by a space 216. The inner core 214 and the outer housing 212 collectively rotate about the rotational axis 940 as whole blood is being processed to separate into a plurality of blood components based upon density. The inner core 214 includes a whole blood or WB inlet passage 218, a red blood cell or RBC passage 220, and a plasma/buffy coat or P/BC outlet passage 222. The whole blood inlet passage 218, the red blood cell passage 220, and the plasma/buffy coat outlet passage 222 may be symmetrically disposed about the rotational axis 940 in a top view of the centrifuge (the "top" being the upper portion of the bowl 210 as shown in FIG. 2F).

A conduit 950 in accordance with the foregoing extends away from the upper portion of the centrifuge bowl 210 in the manner discussed above with regard to the conduit 950 and the centrifuge bowl 10 for the photopheresis kit 1000 (FIG. 1A) and the photopheresis kit 1900 (FIG. 2C). This conduit 950 includes a red blood cell or RBC line or tube 226, a whole blood inlet line or tube 211 (that fluidly connects with the patient collect line 242, and with the collect pump 248 being a boundary between the centrifuge inlet line 211 and the patient collect line 242), and a plasma/buffy coat outlet line or tube 230, each of which will be discussed in more detail below in relation to the fluid/flow diagram presented in FIG. 2G. The RBC line 226 fluidly connects with the RBC passage 220 through the inner core 214 of the centrifuge bowl 210. The centrifuge inlet line 211 fluidly connects with the whole blood inlet passage 218 through the inner core 214 of the centrifuge bowl 210. The plasma/buffy coat outlet line 230 fluidly connects with the plasma/buffy coat outlet passage 222 at the upper portion of the centrifuge bowl 210.

Whole blood is introduced into the space 216 between the outer housing 212 and the inner core 214 at an intermediate location between the top portion and bottom portion of the centrifuge bowl 210 in the view presented in FIG. 2F, and again through the whole blood inlet passage 218. FIG. 2F illustrates three separated blood components within the space 216 between the outer housing 212 and the inner court 214. These blood components include plasma (within a plasma layer or band 322), buffy coat (within a buffy coat layer or band 320), and red blood cells (within an RBC layer or band 318). The plasma has the lowest comparative density, so the plasma band 322 is positioned closest to the rotational axis 940 of the centrifuge bowl 210. The red blood cells have the highest comparative density, so the RBC band 318 is positioned furthest from the rotational axis 940. The buffy coat is of an intermediate comparative density, so the buffy coat band 320 is located between the plasma band 322 and the RBC band 318 in relation to the positioning from the rotational axis 940.

Each of the plasma layer 322 and the buffy coat layer 320 are removed from the centrifuge bowl 210 via the plasma/buffy coat outlet passage 222 and the plasma/buffy coat outlet line 230. In contrast, the red blood cell layer 318 is removed from the centrifuge bowl 210 through the red blood cell passage 220 and the red blood cell line 226. Generally, the entrance to the plasma/buffy coat outlet passage 220 is toward the upper portion of the centrifuge bowl 210, while the entrance to the red blood cell passage 220 is toward the lower or bottom portion of the centrifuge bowl 210. The height of the fluid-containing volume of the centrifuge bowl 210 is designated as $H_1$ in FIG. 2F (measured parallel to the rotational axis 940). The spacing between the entrance to the red blood cell passage 220 and the entrance to the plasma/buffy coat outlet passage 222 is designated as $H_2$ in FIG. 2F (measured parallel to the rotational axis 940). One embodiment has $H_2$ being at least about 80% of $H_1$. Another embodiment has $H_2$ being at least about 90% of $H_1$.

Figure 2G:
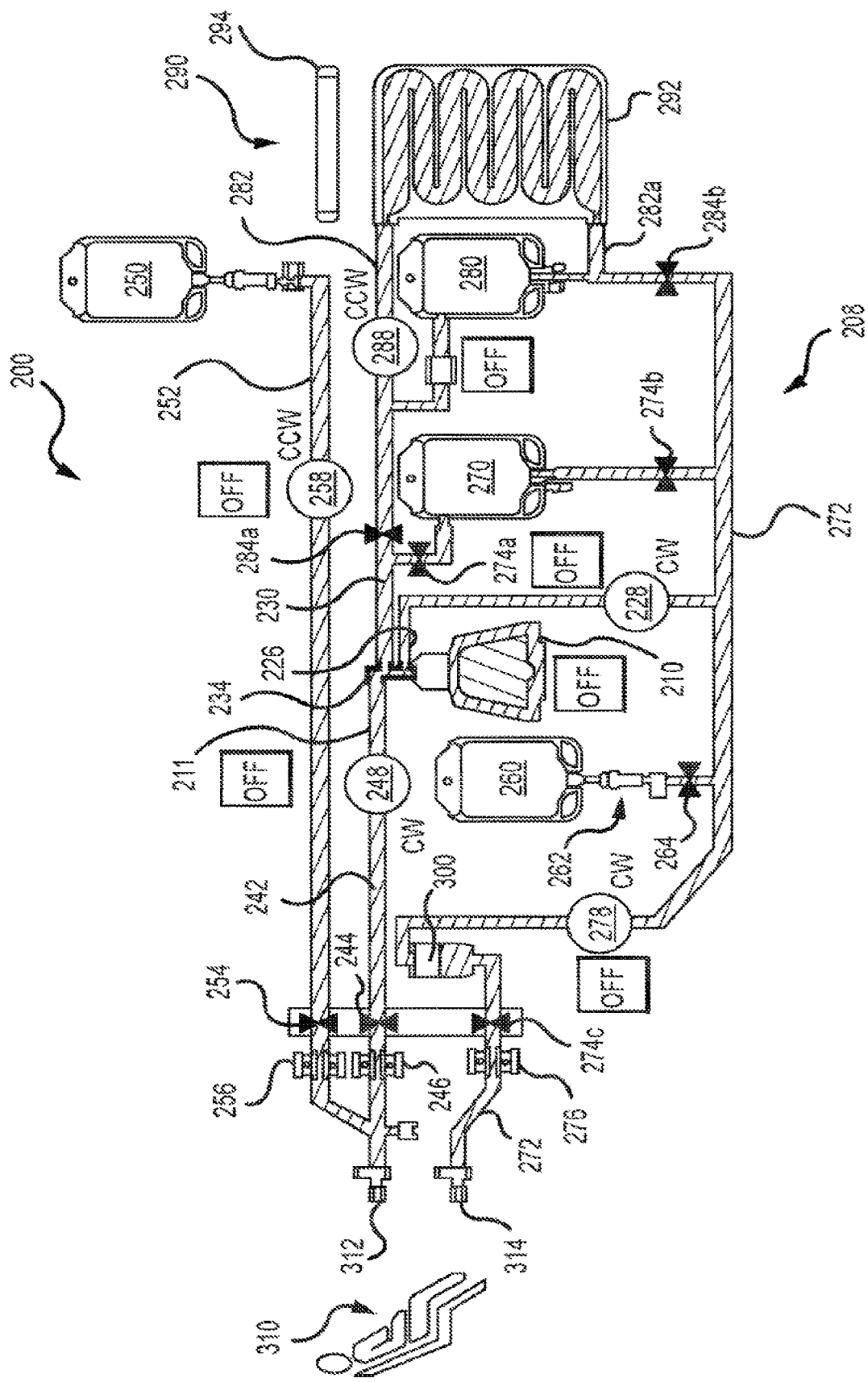
FIG. 2G is a fluid schematic of a photopheresis system that utilizes a disposable kit at least generally in accordance with FIG. 2C.

A schematic of a fluid or flow diagram for a photopheresis system is illustrated in FIG. 2G, is identified by reference numeral 200, and is at least generally in accordance with using the tower system 2000 (FIG. 2A) and the disposable photopheresis kit 1900 (FIG. 2C). FIG. 2G may be characterized as a graphical output that may be presented on a display or screen of the photopheresis system 200 (e.g., display 206d-FIG. 2H). FIG. 2G may also be characterized as illustrating a disposable photopheresis kit 208 for the photopheresis system 200 (along with other components of the photopheresis system 200, such as various pumps). In any case, what is presented in FIG. 2G is commonly referred to as being of a dual needle configuration—where blood is withdrawn from a patient 310 at one location (via a collect access 312, for instance on one arm) and is returned to the patient 310 at a different location (via a return access 314, for instance on the other arm).

The photopheresis system 200 utilizes a number of fluid sources for conducting a photopheresis procedure, including an anticoagulant container or bag 250 and a saline container or bag 260. Fluids also directed into and/or out of a centrifuge bowl 210, a return bag 270, and a treatment bag 280 of the photopheresis system 200 while conducting a photopheresis procedure.

Fluid flow throughout the photopheresis kit 208 may be generated by five different pumps of the photopheresis system 200 to transfer fluid between various locations, and each may be of any appropriate type (e.g., peristaltic): collect pump 248; anticoagulant pump 258; recirculation pump 288; red blood cell pump 228; and return pump 278. The collect pump 248 withdraws whole blood from the patient 310, and directs this whole blood through a collect line 242, through a centrifuge inlet line 211, through a multi-port/multiple flowpath coupling 234, and then into the centrifuge bowl 210 (via whole blood inlet passage 218). The patient collect line 242 may be defined as that portion of the flowpath extending from the patient 310 to the collect pump 248, while the centrifuge inlet line 210 may be defined as that portion of the flowpath that extends from the collect pump 248 to the centrifuge bowl 210. The patient collect line 242 and the centrifuge inlet line 210 may then just be different portions of a common tube.

An air detector 246 and a collect valve 244 are associated with the noted patient collect line 242 (i.e. located between the collect pump 248 and the patient 310). The collect valve 244 may be disposed in both an open position (to allow flow) and a closed position (to terminate flow). The photopheresis system 200 utilizes two other air detectors 256 and 276 (discussed below). When air is detected by any of the detectors 246, 256, or 276, the photopheresis system 200 is configured to: 1) terminate operation of all pumps 248, 258, 288, 228, and 278; and 2) to activate one or more alarms. After activation of any such alarm, the photopheresis system 200 may be configured so as to operate the collection pump 248 to withdraw a predetermined amount of fluid (e.g., 1-2 mL) from the patient 310 before the resetting the alarm (i.e., the air detector 246 will not reactivate an alarm(s) until after the collection pump 248 has directed the above-noted predetermined volume of whole blood past the air detector 246.

Anticoagulant is disposed in the anticoagulant bag 250 and is fluidly connectable with the patient collect line 242. An anticoagulant line 252 extends from the anticoagulant bag 250 to the patient collect line 242, preferably in proximity to the patient collect access 312. The anticoagulant pump 258 may be operated to transfer anticoagulant from the anticoagulant bag 250 to the patient collect line 242 (via the anticoagulant line 252). An air detector 256 and an anticoagulant valve 254 are associated with the anticoagulant line 252. The anticoagulant valve 254 may be disposed in both an open position (to allow flow) and a closed position (to terminate flow).

Saline is disposed in the saline bag 260 and is fluidly connectable with a patient return line 272 (which in turn is associated with the patient return access 314). A saline line 262 extends from the saline bag 260 to the patient return line 272. A saline valve 264 is disposed in the saline line 262. The saline valve 264 may be disposed in both an open position (to allow flow) and a closed position (to terminate flow).

All flow back to the patient 310 through the patient return line 272 is directed into a filter 300. A patient return valve 274c and a patient return air detector 276 are disposed between the filter 300 and the patient return access 314. The patient return valve 274c may be disposed in both an open position (to allow flow) and a closed position (to terminate flow). When each of the saline valve 264 and the patient return valve 274 are in an open position, the return pump 278 may be operated to withdraw saline from the saline bag 260, to direct this saline through the saline line 262 and the return line 272, through the filter 300, and then back into the patient 310 via the patient return access 314.

The centrifuge bowl 210 includes three different fluid accesses—a single fluid inlet (centrifuge inlet line 211, which again merges into the patient collect line 242) and two fluid outlets (a plasma/Buffy coat outlet line 230 and a red blood cell line 226). Each of the centrifuge inlet line 211, the plasma/buffy coat outlet line 230, and the red blood cell line 226 fluidly connect with the centrifuge bowl 210 by the above-noted coupling 234. Whole blood may be directed into the centrifuge bowl 210 (through the centrifuge inlet line 211), while at the same time one or more of red blood cells are being withdrawn from the centrifuge bowl 210 (through the red blood cell line 226) and plasma and/or buffy coat are being withdrawn from the centrifuge bowl 210 (through the plasma/buffy coat outlet line 230).

A flow of plasma and/or buffy coat out of the centrifuge bowl 210 through the plasma/buffy coat outlet line 230 may be directed to either the return bag 270 or to the treatment bag 280. There is a return bag top valve 274a to control the flow from the plasma/buffy coat collect line 230 to the return bag 270. The return bag top valve 274a may be disposed in both an open position (to allow flow) and a closed position (to terminate flow). There is a treatment bag inlet valve 284a to control the flow from the plasma/buffy coat collect line 230 to the treatment bag 280. The treatment bag inlet valve 284a may be disposed in both an open position (to allow flow) and a closed position (to terminate flow).

Flow from each of the return bag 270 and the treatment bag 280 may be directed into the patient return line 272. There is a return bag bottom valve 274b to control the flow from the return bag 270 to the patient collect line 272. The return bag bottom valve 274b may be disposed in both an open position (to allow flow) and a closed position (to terminate flow). There is a treatment bag outlet valve 284a to control the flow from the treatment bag 280 to the patient collect line 272. The treatment bag outlet valve 284b may be disposed in both an open position (to allow flow) and a closed position (to terminate flow).

A flow out of the centrifuge bowl 210 may be directed into the return bag 270, or may be directed into the treatment bag 280. Control of the flow out of the centrifuge bowl 210 to the desired destination is facilitated by appropriately configuring the various valves of the photopheresis kit 208. A flow of red blood cells out of the centrifuge bowl 210 (through the red blood cell line 226) and into the return bag 270 may be realized by having: the red blood cell pump 228 in an "on" state; the return bag bottom valve 274b in an open position; the return bag top valve 274a and the treatment bag inlet valve 284a each being in a closed position. A flow of plasma out of the centrifuge bowl 210 (through the plasma/buffy coat outlet line 230) and into the return bag 270 may be realized by having: the return bag top valve 274a in an open position; and the treatment bag inlet valve 284a in a closed position. A flow of plasma and/or buffy coat out of the centrifuge bowl 210 (through the plasma/buffy coat outlet line 230) and into the treatment bag 270 may be realized by having: the return bag top valve 274a in a closed position; and the treatment bag inlet valve 284a in an open position.

The contents of the treatment bag 280 may be subjected to photo-therapy. The photopheresis system 200 thereby includes a photo-activation module 290 having at least one light source 294 (e.g., one or more UVA light sources; an array of UVA light sources). An irradiation bag, container, or chamber 292 of the photopheresis kit 208 is appropriately positioned relative to light source 294. A treatment line 282 may be characterized as extending from the plasma/buffy coat outlet line 230 to an inlet of a radiation bag, container, or chamber 292 of a photo-activation module 290, while a recirculation line 282a extends from an outlet of the irradiation bag 292 back to the treatment bag 280. The contents of the treatment bag 280 may be recirculated through the irradiation bag 292 by operation of the recirculation pump 288, and each of the treatment bag inlet valve 284a and the treatment bag outlet valve 284a being in a closed position.

Figure 2H:
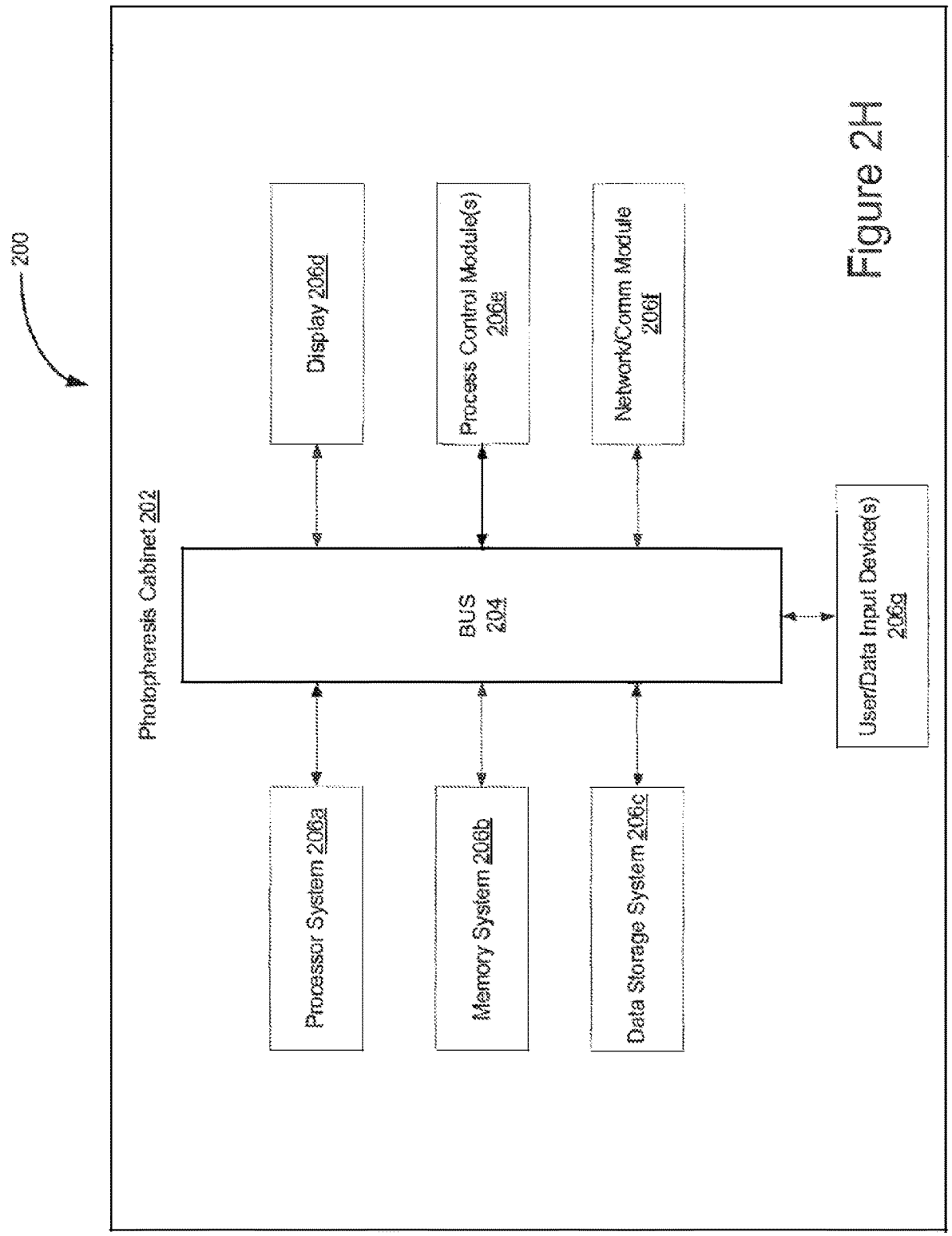
FIG. 2H is a schematic of a control architecture that may be used by a photopheresis system.

FIG. 2H is a further schematic representation of the above-discussed photopheresis system 200, namely schematically illustrating a photopheresis tower, cabinet, or base unit 202 that may utilize the above-discussed disposable kit 208 to conduct a photopheresis procedure. The photopheresis cabinet 202 may include a processor system 206a (e.g., one or more processors that utilize any appropriate processing architecture), a memory system 206b, a data storage system 206c (a computer-readable storage medium of any appropriate type or types and in a non-transitory form (e.g., a non-transitory computer-readable storage medium), including without limitation by using one or more data storage devices of any appropriate type and utilizing any appropriate data storage architecture), a monitor or display 206d, at least one process control module 206e, a network/communication module 206f, and at least one user/data input device 206e (e.g., a keyboard, mouse, incorporating touch screen functionality on the display 206d).

A number of protocols for controlling one or more aspects of a photopheresis procedure will now be addressed. At least some of these protocols will be addressed in relation to the photopheresis system 200 of FIG. 2G (and the various other figures that pertain to this particular photopheresis system 200), although it should be appreciated that each of these protocols may be utilized by any appropriate photopheresis system. Each of the following protocols may be incorporated/embodied by a non-transitory computer-readable storage medium (e.g., each such protocol may be of a non-transitory form). In the case of the photopheresis system 200, each such protocol could be in the form of a separate process control module 206e, although a given process control module 206e of the photopheresis system 200 could incorporate two or more of these protocols.

Purging Air Bubbles Out of Centrifuge Bowl Using Pressure

In some embodiments, air bubbles may be purged from the centrifuge bowl via pressure, which may be used to swell the bowl so as to "burp" air and microbubbles therefrom, and/or from an umbilicus thereof (of the photopheresis system). Such a configuration and/or procedure may be used to improve the priming of a rigid centrifuge bowl used in an apheresis/photopheresis procedure. For example and as shown in the flow chart of FIG. 3A (which may be characterized as an air purge protocol 400 for a photopheresis system), the centrifuge bowl may be filled with a fluid, such as blood or water (402). The centrifuge bowl may be pressurized (404), which may be achieved by continuing to collect fluid from an inlet pump while bowl outlets, including outlets for plasma and red blood cells, are closed. Bowl pressure may be measured, and if the pressure within the bowl is below a first threshold (406), the inlet may remain open (while the outlets remain closed) until the pressure reaches the first threshold. The pressure within the bowl may be measured constantly until the pressure reaches the first threshold, or pressure measurements may be taken at intervals determined by factors such as time and/or measured volume input. In some embodiments, the first threshold may be about 9 PSI.

Upon reaching the first threshold, the bowl may be opened (e.g., the plasma outlet may be opened) to purge the air and/or microbubbles (408). In some embodiments, the inlet may remain open during the purge, but the inlet may be closed while the outlet is opened to purge the air bubbles.

After the purge, the open outlet is closed and the inlet is open, such that the fluid enters the bowl, but the outlets are closed (410). The bowl pressure may be measured (constantly or at intervals, as described above), and the inlet pump may continue running (410) until the pressure reaches a second threshold (412). In some embodiments, the second threshold may be less than the first threshold. For example, the second threshold pressure may be about 6 PSI.

In some embodiments, the inlet may remain open and the outlets may remain closed until pressure reaches the second threshold, at which time, the centrifuge can be spun up (414). This is so when the centrifuge spins up, the pressure inside the bowl remains positive such that no further air should get drawn in through an outlet (e.g., the plasma outlet). In some embodiments, the inlet and outlets may be closed when the centrifuge spins. The bowl may be further pressurized by running the inlet pump while outlets are closed (416). The bowl pressure may be measured (as described above) until the pressure reaches a third threshold (418). The third threshold may be the same as the second threshold. Once the pressure reaches the third threshold, the plasma outlet may be opened to purge the remaining air and/or micro bubbles (420), and the protocol 400 may be terminated (422).

Figure 3A:
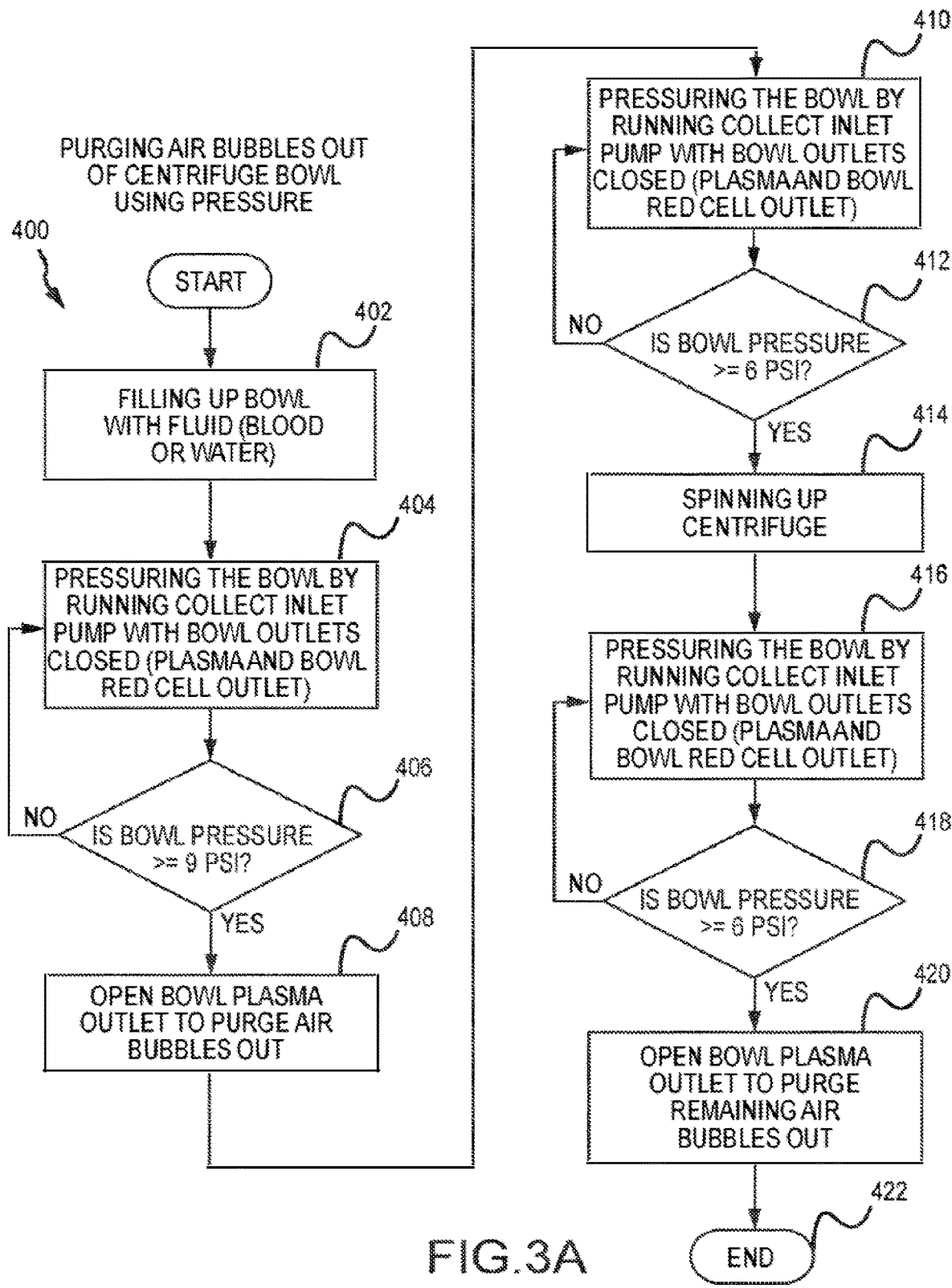
FIG. 3A is an embodiment of a protocol for purging air bubbles out of a centrifuge bowl of a photopheresis kit of the type shown in FIGS. 1A and 2C.

FIG. 3B shows a flow chart similar to FIG. 3A (and which may also be characterized as an air purge protocol 430 for a photopheresis system), wherein the first threshold pressure is about 460 mmHg (406'), the second threshold pressure is about 300 mmHg (412'), and the third threshold is about 300 mmHg (418').

Figure 4:
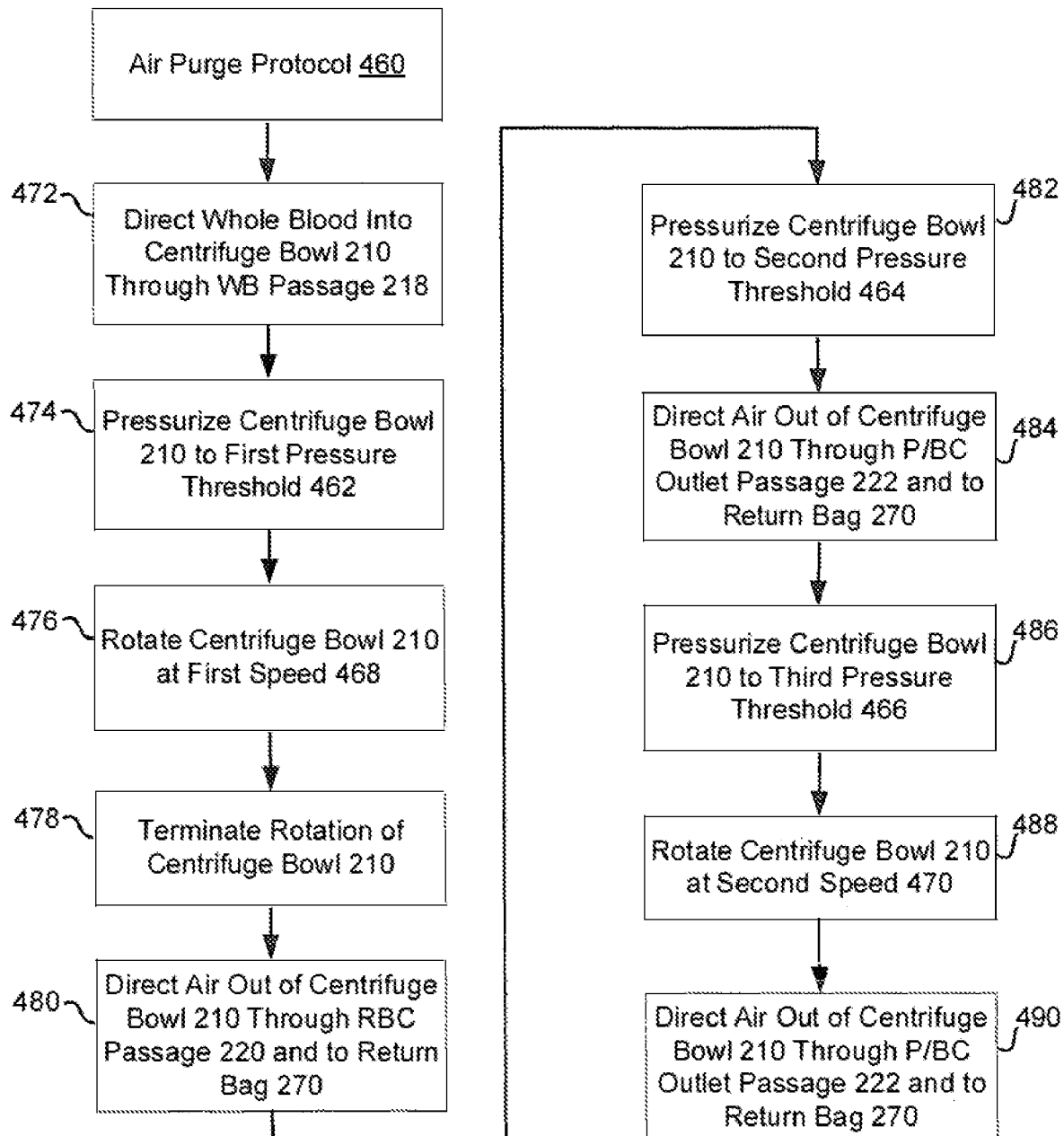
FIG. 4 is another embodiment of a protocol for purging air out of a centrifuge bowl of a photopheresis kit of the type shown in FIGS. 1A and 2C.
Figure 4A:
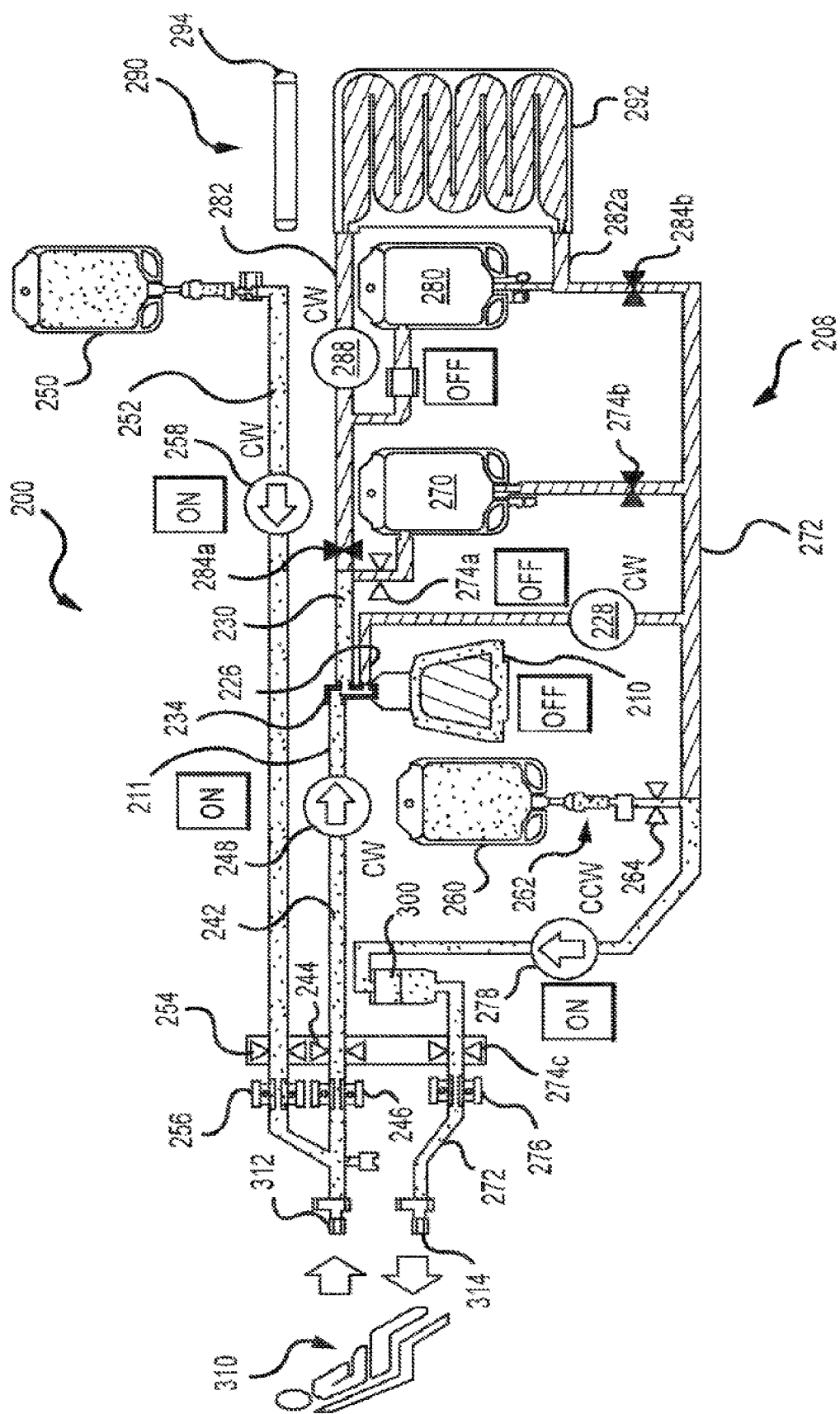
FIGS. 4A-4H are each a fluid schematic of the photopheresis system shown in FIG. 2C, but in various different configurations or states during execution of the air purge protocol of FIG. 4.

Another embodiment of an air purge protocol for a photopheresis system is illustrated in FIG. 4 and is identified by reference numeral 460. Whole blood is directed into the centrifuge bowl 210, and will proceed through the whole blood inlet passage 218 to the space 216 between the outer housing 212 and inner core 214 (step 472). This is depicted in the fluid/flow diagram of FIG. 4A, where: 1) the patient collect valve 244 is open; 2) the collect pump 248 is operated to direct flow in the direction indicated by the corresponding pump arrow and into the centrifuge bowl 210 through the whole blood inlet passage 218; 3) the treatment bag inlet valve 284a is closed; 4) the return bag bottom valve 274b is closed; 5) the red blood cell pump 228 is off (which thereby blocks flow from the red blood cell outlet line 226 into the patient return line 272); and 6) the centrifuge bowl 210 is off (i.e., is not rotating).

Figure 4B:
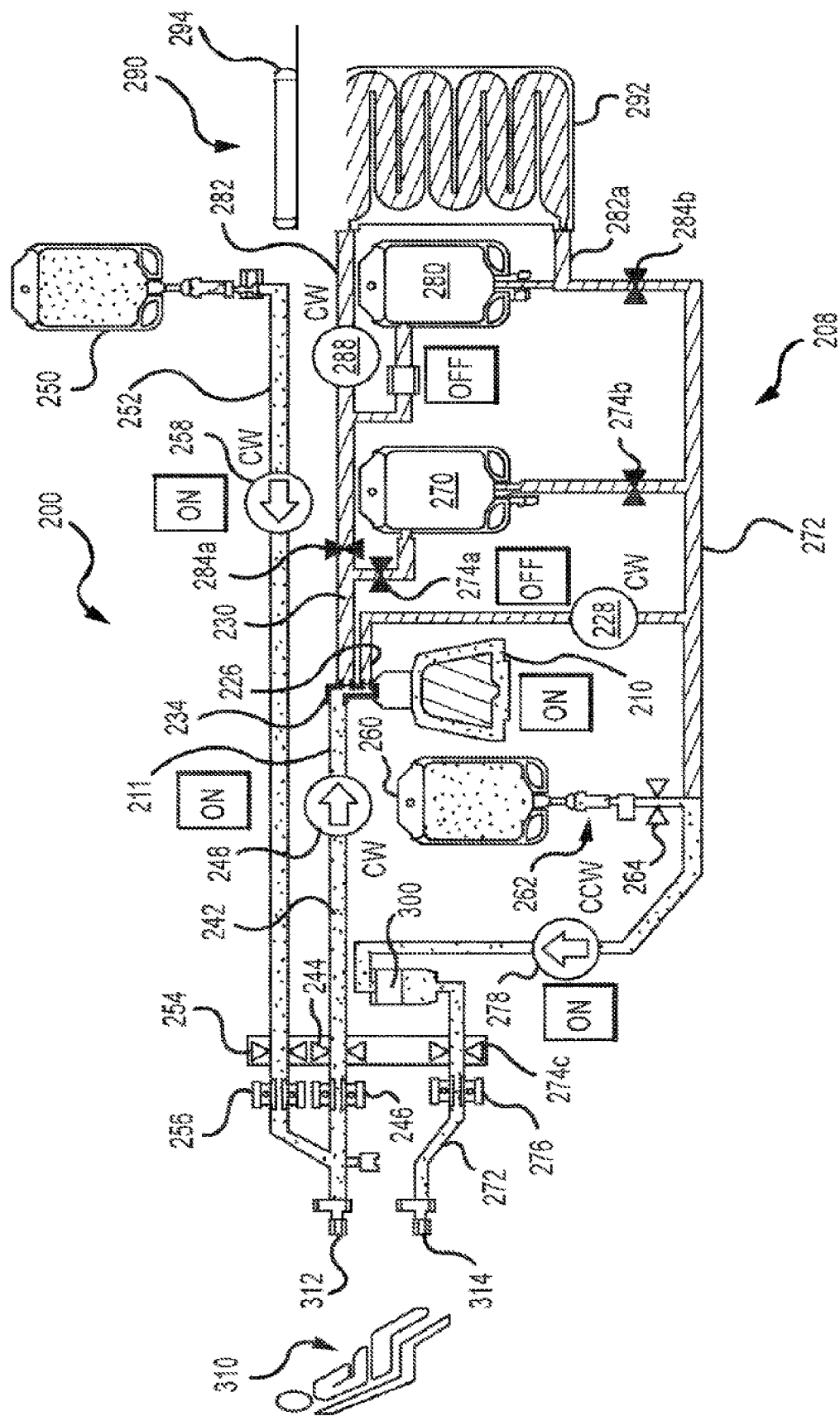

The centrifuge bowl 210 is pressurized to a first pressure threshold 462 pursuant to step 474 of the air purge protocol 460. The pressure of the centrifuge bowl 210 may be monitored via a pressure sensor associated with the centrifuge inlet line 211 (e.g., pressure dome 1745 (FIG. 2C) and pressure transducer 1775 (FIG. 2B) of the photopheresis system 3000). Whole blood continues to be directed into the centrifuge bowl 210, and will proceed through the whole blood inlet passage 218 to the space 216 between the outer housing 212 and inner core 214. This is depicted in the fluid/flow diagram of FIG. 4B, where: 1) the patient collect valve 244 remains open; 2) the collect pump 248 continues to be operated to direct flow in the direction indicated by the corresponding pump arrow; 3) each of the return bag top valve 274a, the treatment bag inlet valve 284a, and the return bag bottom valve 274b are closed; and 4) the red blood cell pump 228 is off (which thereby blocks flow from the red blood cell outlet line 226 into the patient return line 272). In one embodiment, the first pressure threshold 462 is about 460 mmHg.

The centrifuge bowl 210 is rotated at a first speed 468 pursuant to step 476 of the air purge protocol 460. Steps 474 and 476 may be simultaneously executed or at least may be executed so as to overlap to at least some degree. As such, the fluid/flow diagram of FIG. 4B also embodies step 476. Note that the centrifuge bowl 210 is identified as being rotated in FIG. 4B for purposes of step 476. One embodiment has the first speed 468 being about 400 RPM.

Figure 4C:
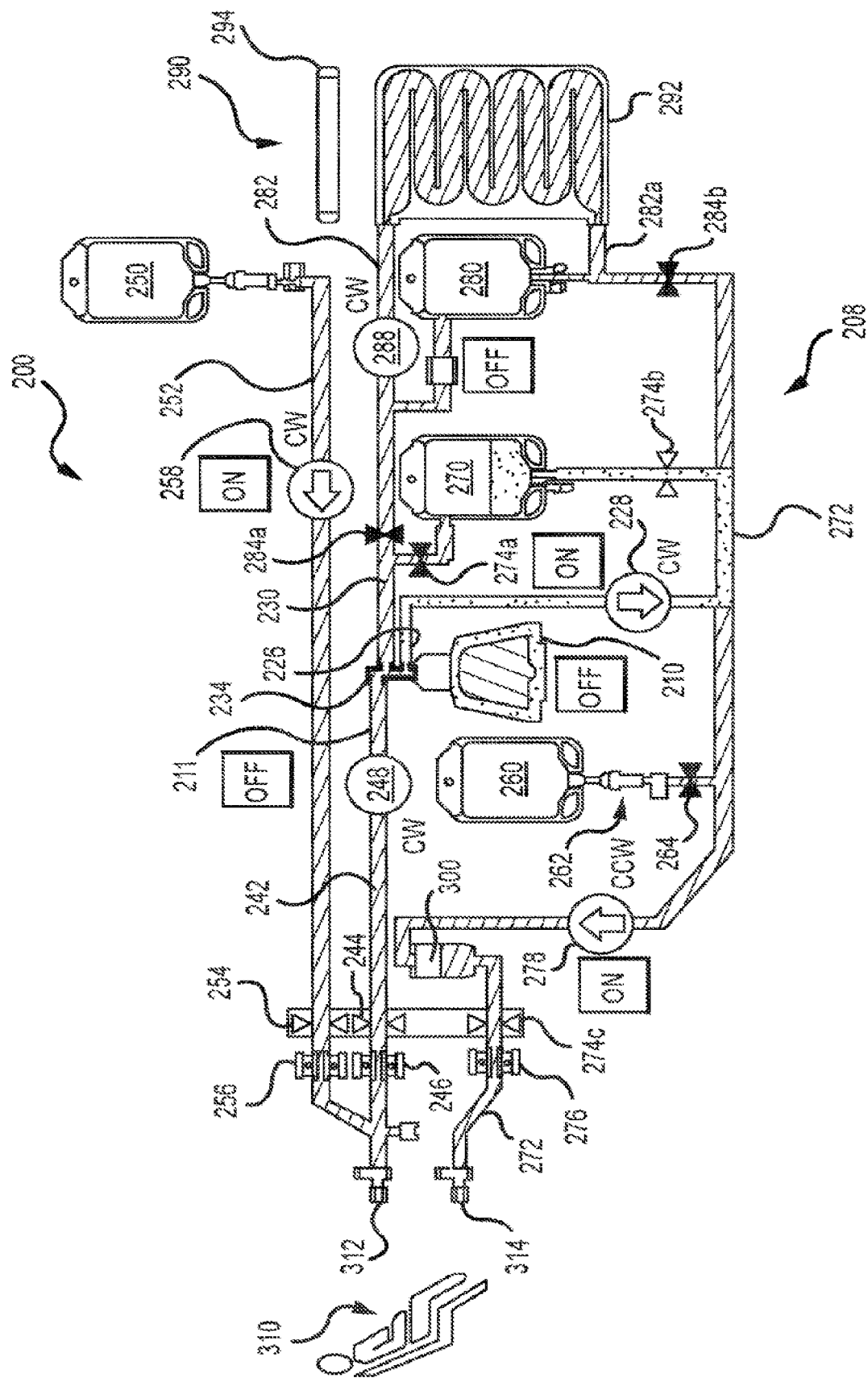

Rotation of the centrifuge bowl 210 is terminated (step 478), and air is directed out of the centrifuge bowl 210, through the red blood cell passage 220 (e.g., from the bottom of the centrifuge bowl 210), through the red blood cell line 226, and into the return bag 270 (step 480). This is depicted in the fluid/flow diagram of FIG. 4C, where: 1) the patient collect valve 244 remains open; 2) the collect pump 248 is off (which thereby blocks flow between the patient 310 and the centrifuge bowl 210); 3) each of the return bag top valve 274a, the treatment bag inlet valve 284a, and the saline valve 264 are closed; 4) the return bag bottom valve 274b is open; and 5) the red blood cell pump 228 operated to direct flow in the direction indicated by the corresponding pump arrow and into the return bag 270. In one embodiment, the centrifuge bowl 210 is in a stationary position for execution of step 480.

Figure 4D:
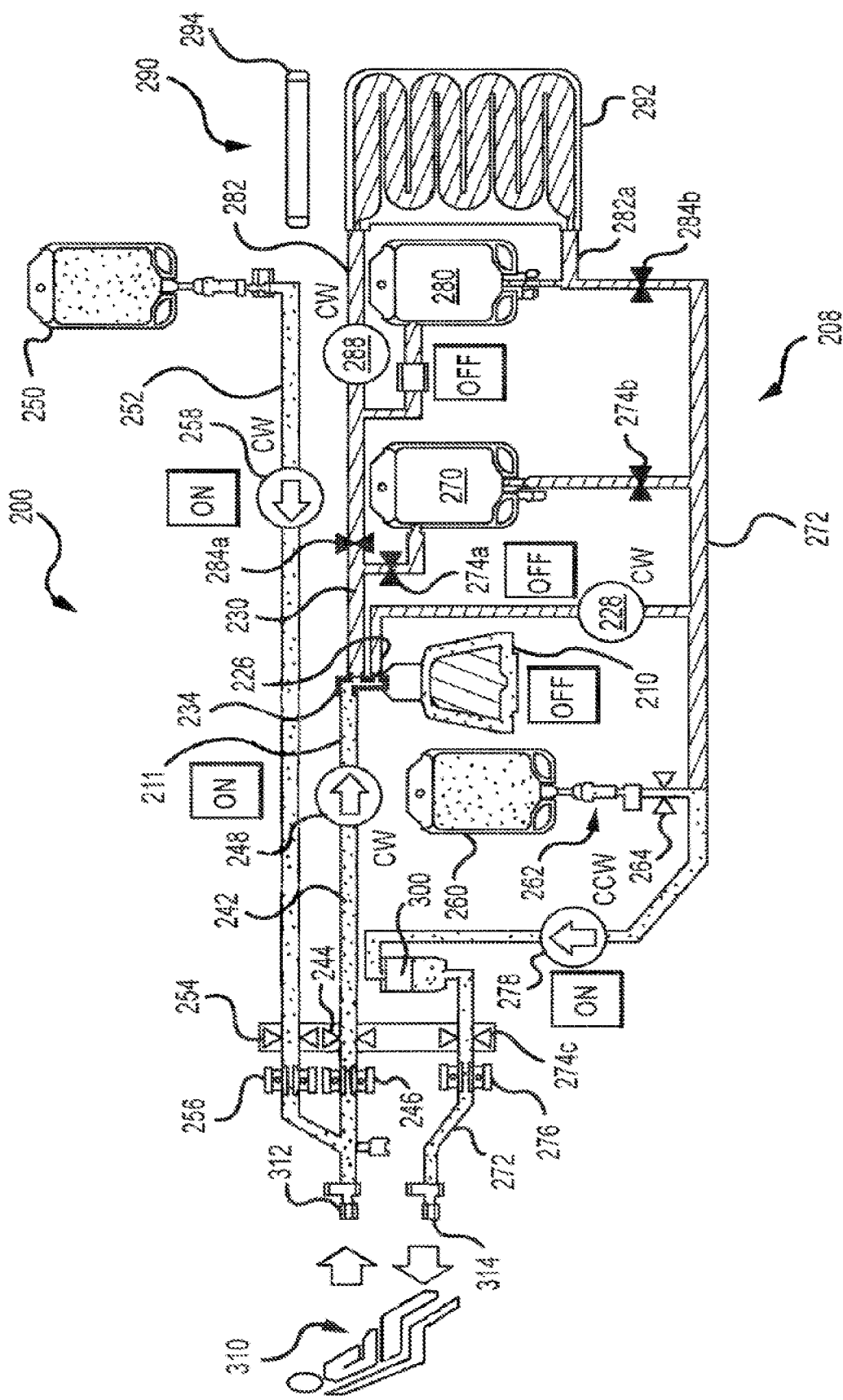

The centrifuge bowl 210 is pressurized to a second pressure threshold 464 pursuant to step 482 of the air purge protocol 460. The pressure of the centrifuge bowl 210 may be monitored via a pressure sensor associated with the centrifuge inlet line 211 (e.g., pressure dome 1745 (FIG. 2C) and pressure transducer 1775 (FIG. 2B) of the photopheresis system 3000). Whole blood is directed into the centrifuge bowl 210, and will proceed through the whole blood inlet passage 218 to the space 216 between the outer housing 212 and inner core 214. This is depicted in the fluid/flow diagram of FIG. 4D, where: 1) the patient collect valve 244 remains open; 2) the collect pump 248 is operated to direct flow in the direction indicated by the corresponding pump arrow; 3) each of the return bag top valve 274a, the treatment bag inlet valve 284a, and the return bag bottom valve 274b are closed; 4) the centrifuge bowl 210 is not being rotated (e.g., the centrifuge bowl 210 may be in a stationary position); and 5) the red blood cell pump 228 is off (which thereby blocks flow from the red blood cell line 226 into the patient return line 272). The second pressure threshold 464 may be about 460 mmHg. As such and in one embodiment, the same pressure threshold may be used for each of steps 474 and 482. Note that the centrifuge bowl 210 is not rotated in conjunction with step 482. One embodiment has the centrifuge bowl 210 remaining in a stationary state from the completion of step 478 at least through execution of step 482.

Figure 4E:
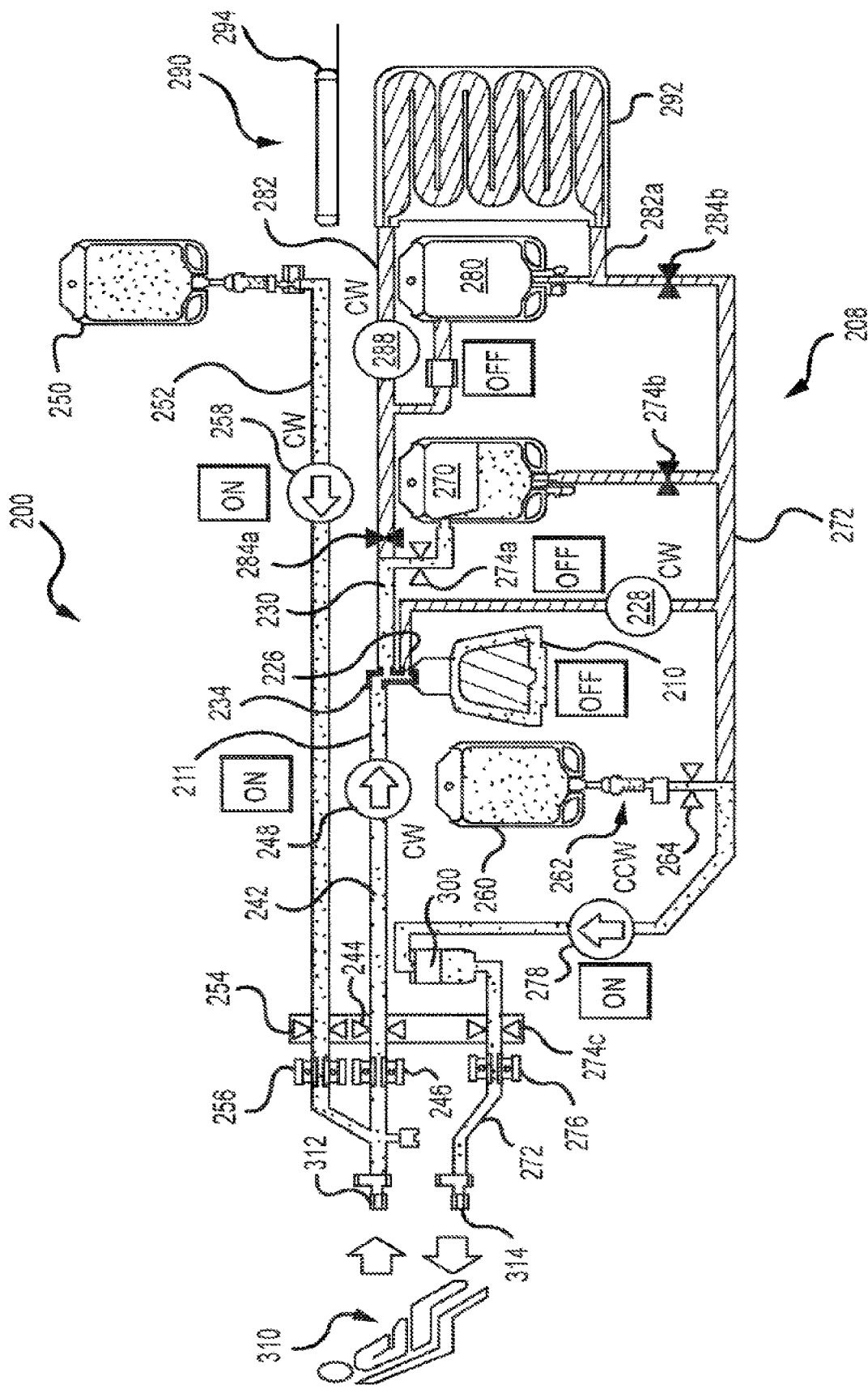

Air is directed out of the centrifuge bowl 210, through the plasma/buffy coat passage 222 (e.g., from the top of the centrifuge bowl 210), through the plasma/buffy coat outlet line 230, and into the return bag 270 pursuant to step 484 of the air purge protocol 460. This is depicted in the fluid/flow diagram of FIG. 4E, where: 1) the patient collect valve 244 remains open; 2) the collect pump 248 is operated to direct flow in the direction indicated by the corresponding pump arrow and into the centrifuge bowl 210 through the whole blood inlet passage 218; 3) the return bag top valve 274a is open; 4) each of the treatment bag inlet valve 284a and the treatment bag outlet valve 284b are closed; 5) the return bag bottom valve 274b is closed; and 5) the red blood cell pump 228 is off (terminating flow from the centrifuge bowl 210, through the RBC line 226, and into the patient return line 272). Note that the centrifuge bowl 210 is also not rotated in conjunction with step 484. One embodiment has the centrifuge bowl 210 remaining in a stationary state from the completion of step 478 at least through execution of step 484.

Figure 4F:
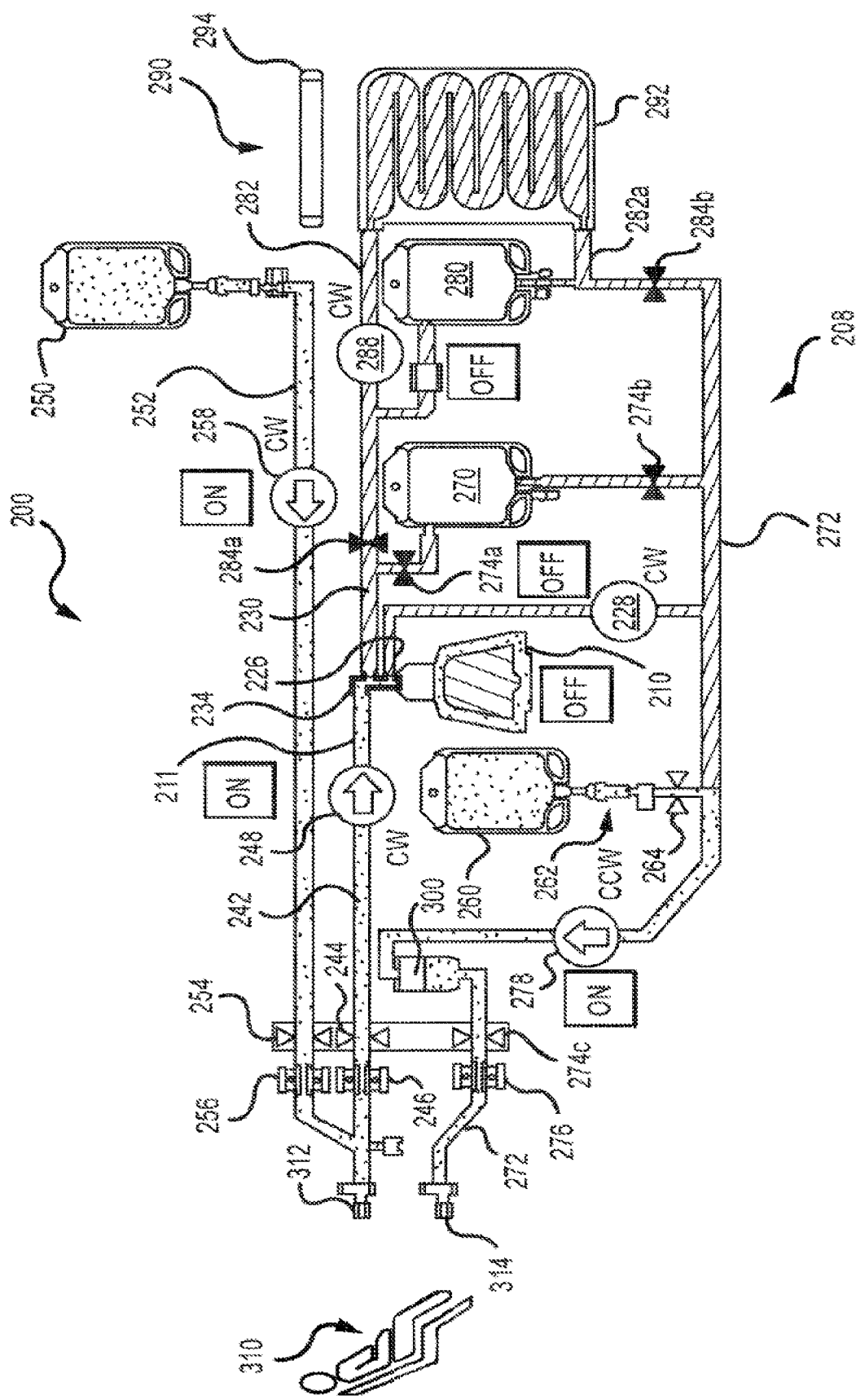

The centrifuge bowl 210 is pressurized to a third pressure threshold 464 pursuant to step 486 of the air purge protocol 460. The pressure of the centrifuge bowl 210 may be monitored via a pressure sensor associated with the centrifuge inlet line 211 (e.g., pressure dome 1745 (FIG. 2C) and pressure transducer 1775 (FIG. 2B) of the photopheresis system 3000). Whole blood is directed into the centrifuge bowl 210, and will proceed through the whole blood inlet passage 218 to the space 216 between the outer housing 212 and inner core 214. This is depicted in the fluid/flow diagram of FIG. 4F, where: 1) the patient collect valve 244 remains open; 2) the collect pump 248 is operated to direct flow in the direction indicated by the corresponding pump arrow and into the centrifuge bowl 210 through the whole blood inlet passage 218; 3) each of the return bag top valve 274a, the treatment bag inlet valve 284a, the return bag bottom valve 274b, and the treatment bag outlet valve 284b are closed; 4) the centrifuge bowl 210 is not being rotated (e.g., the centrifuge bowl 210 may be in a stationary position); and 5) the red blood cell pump 228 is off (which thereby blocks flow from the red blood cell line 226 into the patient return line 272). The third pressure threshold 464 may be about 300 mmHg. Note that the centrifuge bowl 210 is not rotated in conjunction with step 486. One embodiment has the centrifuge bowl 210 remaining in a stationary state from the completion of step 478 through the completion of step 486.

Figure 4G:
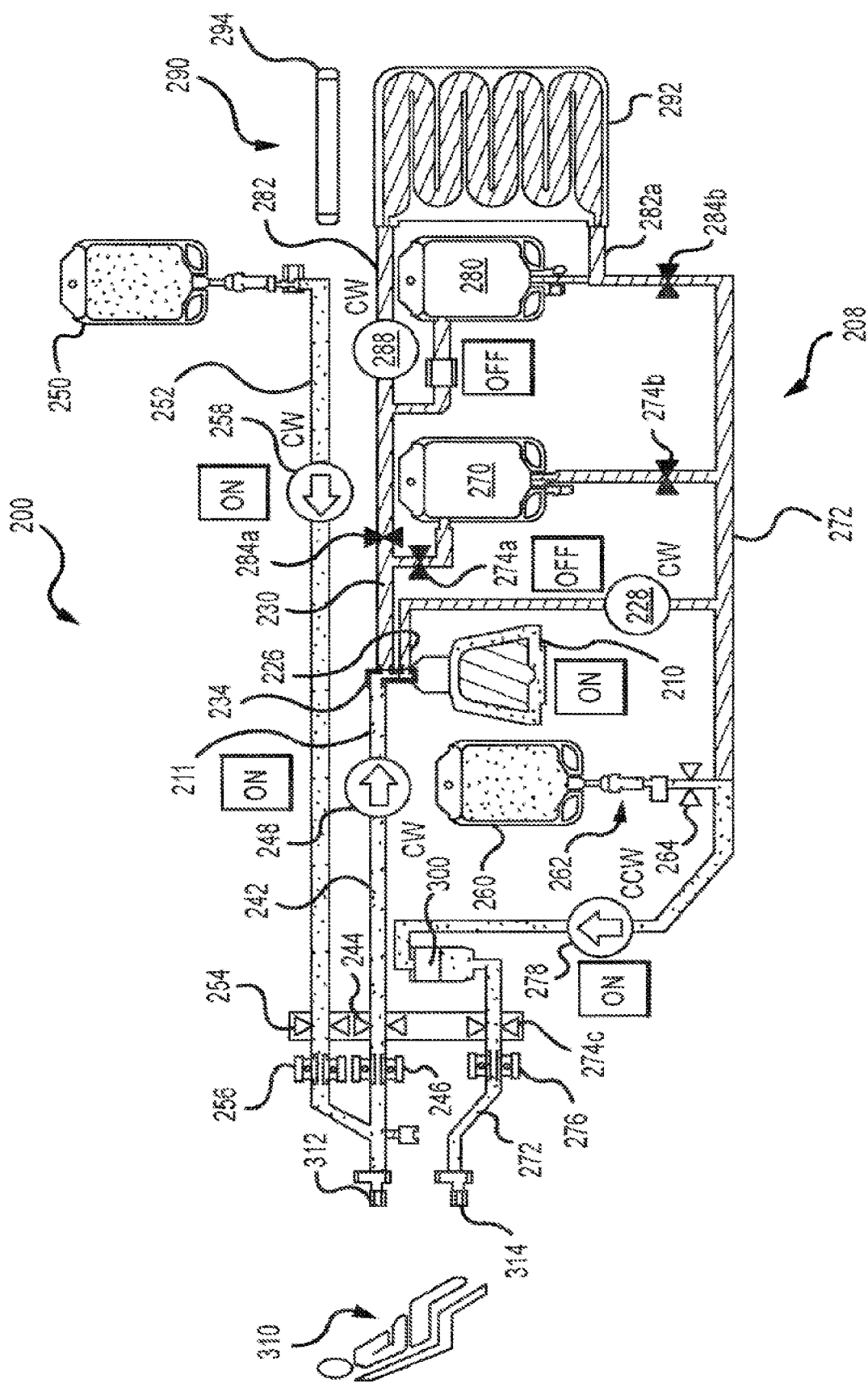

After the pressure in the centrifuge bowl 210 has reached the third pressure threshold 466 associated with step 486, the centrifuge bowl 210 is rotated at a second speed 470 pursuant to step 488 of the air purge protocol 260. This is depicted in the fluid/flow diagram of FIG. 4G, where: 1) the patient collect valve 244 remains open; 2) the collect pump 248 continues to be operated to direct flow in the direction indicated by the corresponding pump arrow and into the centrifuge bowl 210 through the whole blood inlet passage 218; 3) each of the return bag top valve 474a, the treatment bag inlet valve 284a and the treatment bag outlet valve 284b are closed; 4) the centrifuge bowl 210 is rotated at the noted second speed 470; and 5) the red blood cell pump 228 is off (which thereby blocks flow from the red blood cell outlet line 226 into the patient return line 272). The second speed 470 for step 488 of the air purge protocol 460 may be of a value that will be used for separating the whole blood into the noted plurality of blood components (e.g., plasma, buffy coat, red blood cells). This may be a user input value (e.g., 3,200 RPM to 4,800 RPM) or may be a default value for the photopheresis system 200 (e.g., 3,400 RPM). One embodiment has the second speed 470 (step 488) being greater than the first speed 468 (step 476), and one embodiment has the second speed 470 (step 488) being significantly greater than the first speed 458 (step 476). For instance, the second speed 470 (step 488) may be greater than the first speed 468 (step 476) by a factor of at least 7 or 8.

Figure 4H:
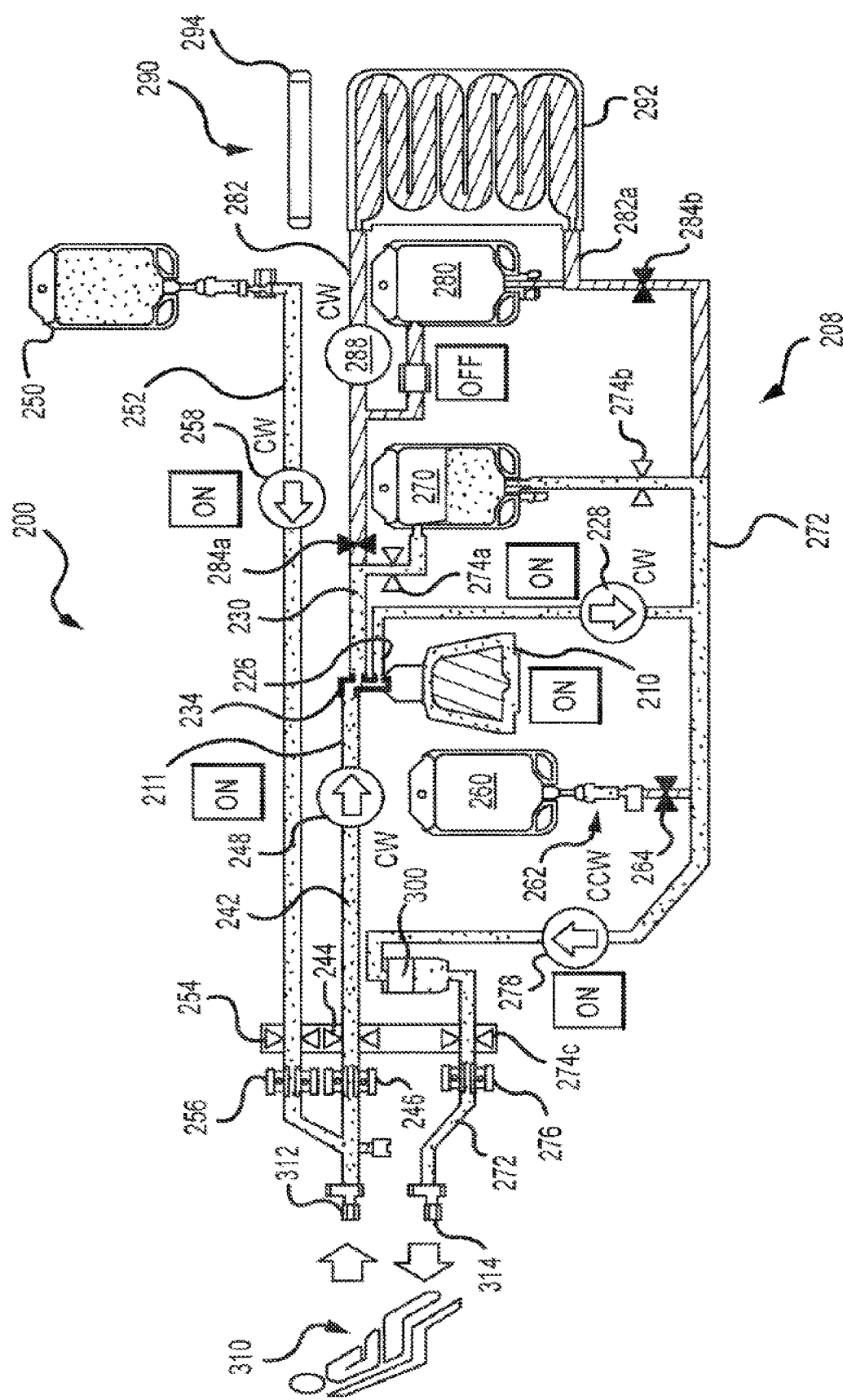

Air is directed out of the centrifuge bowl 210, through the plasma/buffy coat outlet passage 222 (e.g., from the top of the centrifuge bowl 210), through the plasma/buffy coat outlet line 230, and into the return bag 270 pursuant to step 490 of the air purge protocol 460 (air could also be directed out of the centrifuge bowl 210, through the red blood cell passage 220, through the red blood cell line 226, and into the return bag 270 pursuant to step 490 of the air purge protocol 460). This is depicted in the fluid/flow diagram of FIG. 4H, where: 1) the patient collect valve 244 remains open; 2) the collect pump 248 is operated to direct flow in the direction indicated by the corresponding pump arrow and into the centrifuge bowl 210 through the whole blood inlet passage 218; 3) the centrifuge bow 210 continues to be rotated (e.g., at the second speed 470); 4) the return bag top valve 274a is open; 5) each of the treatment bag inlet valve 284a and the treatment bag outlet valve 284b are closed; 5) the return bag bottom valve 274b is closed; and 5) the red blood cell pump 228 is operated to direct flow in the direction indicated by the corresponding pump arrow and into the return bag 270.

Verifying Proper Installation of Pressure Domes

In some embodiments, three pressure sensors (or three sets of pressure sensors) are provided, such that one sensor (or set of sensors) monitors each of (1) the pressure of blood collection, (2) pressure of fluid return to the patient, and (3) pressure within the centrifuge bowl. The disposable photopheresis kit may include three pressure domes (e.g., the photopheresis kit 1900 of FIG. 2C), where one pressure dome is associated with each of the pressure sensors (or sets of pressure sensors). While the operator sets up the photopheresis kit to treat a patient, the three pressure domes may be installed onto the sensors so that the sensors can measure the pressure inside the disposable photopheresis kit. If the pressure in any one of these areas exceeds a threshold pressure, an alarm may indicate that an abnormal condition has arisen (such as improper installation).

Positive and/or negative pressure may be used to determine whether pressure domes of the photopheresis kit are loaded properly and interfacing correctly, thereby ensuring that the instrument functions properly. Such tests may be performed before the instrument is connected to a patient, and therefore can be used to determine whether the instrument will properly identify high and low pressure situations when the instrument is connected to the patient. What may be characterized as pressure testing protocols for a photopheresis system are presented in FIGS. 5A and 5B.

Figure 5A:
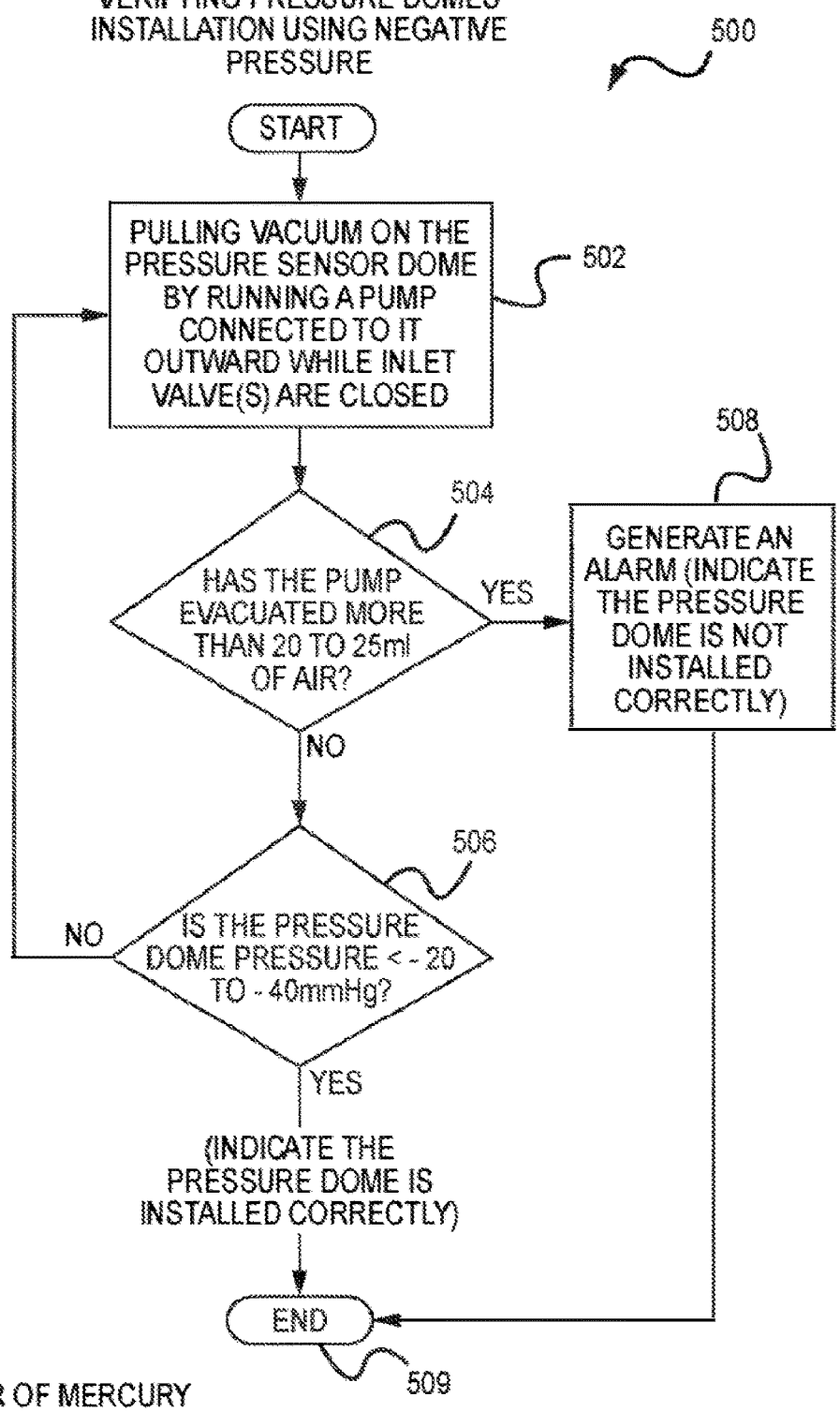
FIG. 5A is an embodiment of a protocol for verifying proper installation of a pressure dome (utilized by a photopheresis kit at least generally of the type shown in FIG. 2C) using negative pressure.

As shown in FIG. 5A for the case of a pressure testing protocol 500, applying negative pressure to a pressure sensor dome may ensure that a pressure dome is properly installed. As shown, a vacuum may be applied on the pressure sensor dome by operating a pump connected to an outlet valve while the inlet valves are closed (502). A determination may then be made as to whether the pump evacuated more than a predetermined amount (such as about 20-25 mL) of air from the area under the pressure dome (504). If more than the predetermined amount of air has been evacuated and the corresponding pressure reading is not seen from the pressure sensor, an alarm is generated to indicate that the pressure dome is not installed correctly (508). If less than the predetermined amount of air has been evacuated, a determination is made as to whether the dome pressure is within a predetermined pressure range, such as about −20 mmHg to about −40 mmHg (506). If so, the pressure sensor dome is installed correctly, an indication may be generated to indicate proper installation, and the protocol 500 may be terminated (509). If the dome pressure is not within the predetermined pressure range, additional vacuum pressure may be applied, and the same decision tree applied again.

Figure 5B:
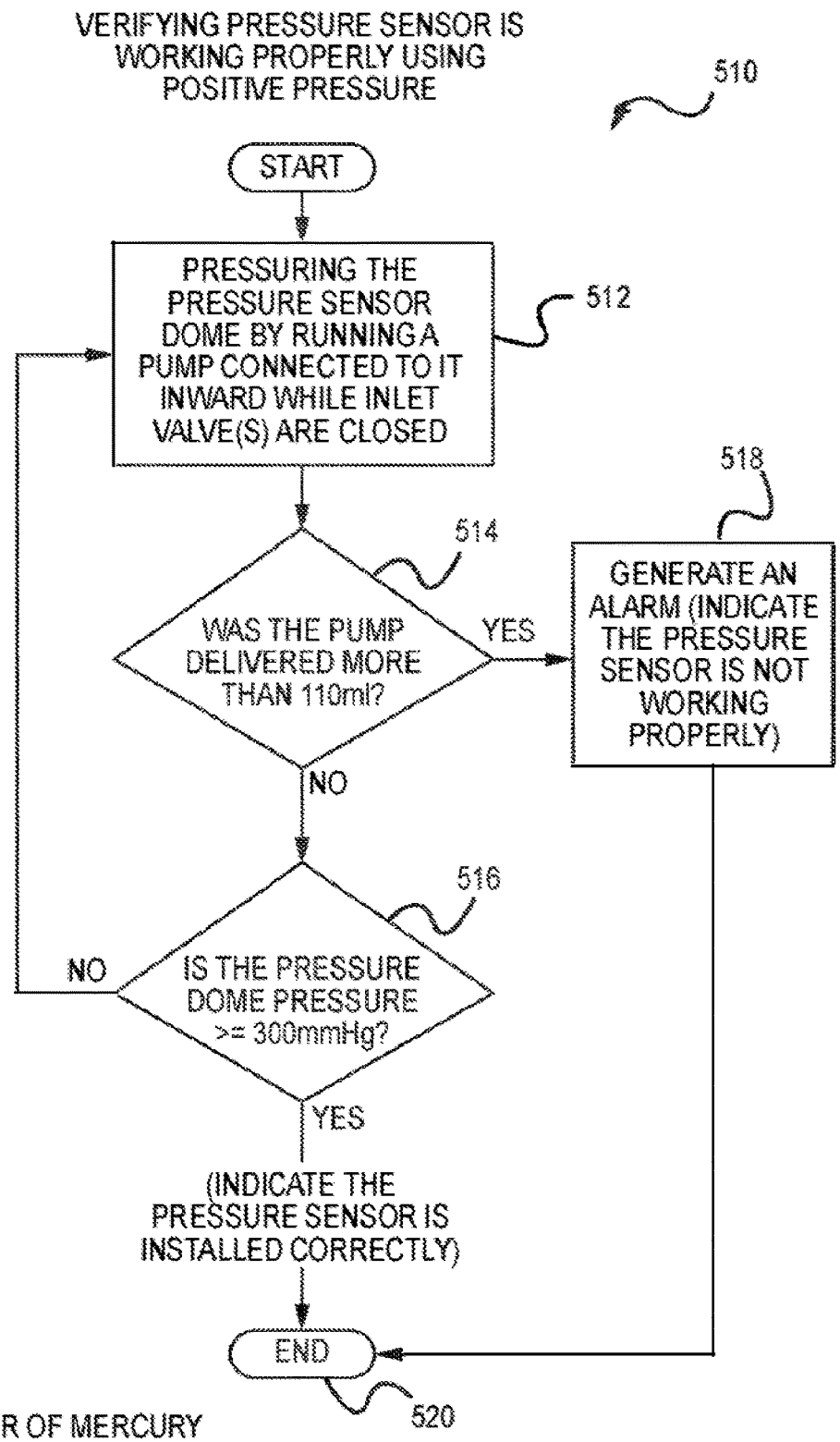
FIG. 5B is an embodiment of a protocol that uses positive pressure to verify pressure sensors of a photopheresis system are working correctly.

Positive pressure may be applied to a pressure dome in order to determine that the pressure sensor(s) is/are working properly, which is depicted in FIG. 5B for the case of a pressure testing protocol 510. Accordingly, the pressure sensor dome may be pressurized by pumping air into the dome via a pump connected to the dome though an inlet valve while all other valves are closed (512). Upon a determination that the pump delivered more than a predetermined volume (514), such as more than about 110 mL, and the corresponding pressure reading is not seen from the pressure sensor, an alarm may be generated to indicate that the pressure sensor is not working properly (518). If the pump has not delivered more than the predetermined volume, a determination is made as to whether the dome pressure is higher than a predetermined dome pressure, such as about 300 mmHg (516). If the pressure exceeds the predetermined dome pressure, an indication may be generated to indicate that the pressure sensor is working properly, and the protocol 510 may be terminated (520). If the pressure does not exceed the predetermined dome pressure, the pressure sensor dome is pressurized again, and the same decision tree is applied.

Figure 6:
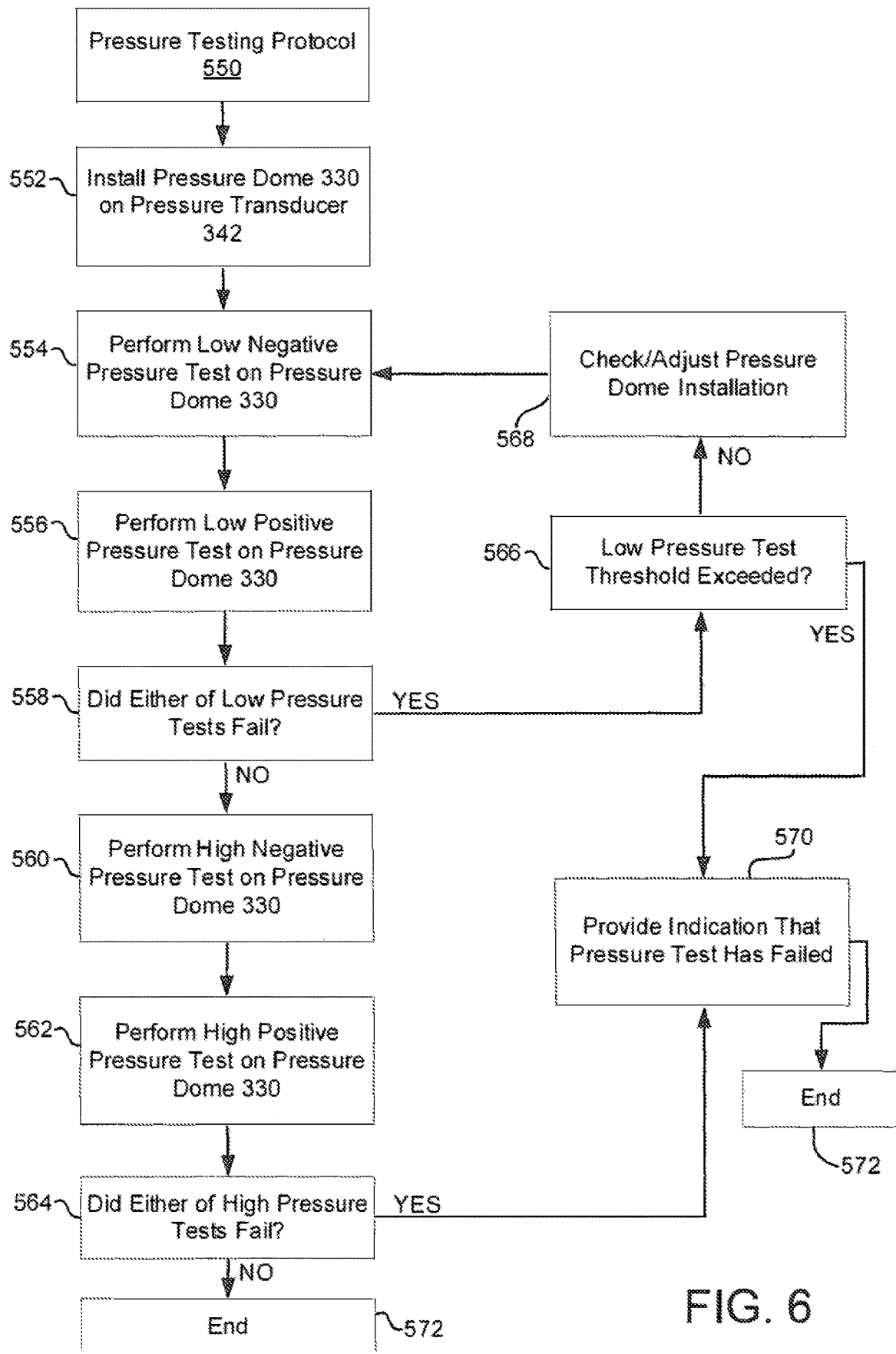
FIG. 6 is an embodiment of a pressure testing protocol for a photopheresis system.

An embodiment of a pressure testing protocol is presented in FIG. 6 and is identified by reference numeral 550. More specifically, the pressure testing protocol 550 may be used to test the installation and/or functionality of a pressure dome of a photopheresis kit (e.g., pressure domes 1744, 1745, and 1746 of the disposable photopheresis kit 1900 (FIG. 2C) and the corresponding pressure transducer of the photopheresis tower or cabinet (e.g., pressure transducers 1754, 1755, in 1756 of the photopheresis system 3000 (FIGS. 2A and 2B). The pressure testing protocol 550 will be discussed in relation to the schematic of the pressure dome 330 and transducer 342 presented in FIG. 2E. By way of initial summary, the pressure testing protocol 550 uses a "low value" pressure test (for both positive and negative pressure, although in one embodiment the low value positive pressure test is not used), as well as a "high value" pressure test (for both positive and negative pressure). These "low" and "high" characterizations are relative to one another. Moreover, the terms "low" and "high" in relation to a negative pressure pertain to the numerical value of the negative pressure.

The pressure dome 330 is installed on its corresponding pressure transducer 342 pursuant to step 552 of the pressure testing protocol 550. The installation of the pressure dome 330 is assessed through execution of steps 554 and 556. Steps 554 and 556 may be executed in any relative order.

In step 554 of the pressure testing protocol 550, a low value negative pressure is applied to the flow chamber 336 of the pressure dome 330 (to generate a first vacuum). This may be accomplished by operating a pump connected to one of the flow ports 338a, 338b of the pressure dome 330, while having a valve associated with the other of the flow ports 338a, 338b being closed. For instance, a corresponding peristaltic pump may be rotated a predetermined times, and which should generate a certain low value negative pressure in the flow chamber 336 of the pressure dome 330. If such a low value negative pressure is not generated in the flow chamber 336 (via an output from the pressure transducer 342), the corresponding low value negative pressure test may be characterized as failing (step 558 of the pressure testing protocol 550). In one embodiment, the negative pressure that should be produced pursuant to step 554 is about −20 mmHG for the pressure dome associated with the patient collect line 242, is about −40 mmHG for the pressure dome associated with the patient return line 272, and is about −25 mmHG for the pressure dome associated with the centrifuge inlet line 211.

In step 556 of the pressure testing protocol 550, a low value positive pressure is applied to the flow chamber 336 of the pressure dome 330. This may be accomplished by operating a pump connected to one of the flow ports 338a, 338b of the pressure dome 330, while having a valve associated with the other of the flow ports 338a, 338b being closed. For instance, a corresponding peristaltic pump may be rotated a predetermined times, and which should generate a certain low value positive pressure in the flow chamber 336 of the pressure dome 330. If such a low value positive pressure is not generated in the flow chamber 336 (via an output from the pressure transducer 342), the corresponding low value positive pressure test may be characterized as failing (step 558 of the pressure testing protocol 550). In one embodiment, step 556 is not in fact used by the pressure testing protocol 550.

If either of the low value negative or low value positive pressure tests of the pressure dome 330 fail, the pressure testing protocol 550 may be configured to repeat these tests after giving the operator the opportunity to reinstall or reposition the pressure dome 330 (e.g., the pressure testing protocol 550 may proceed from step 558 to step 568, and may then proceed with repeating steps 554 and 556). The pressure testing protocol 550 may also include step 566, which may be utilized to dictate how many times the low value pressure tests may be repeated on a given pressure dome 330. If step 566 has been reached, and if the low value pressure tests associated with steps 554 and 556 have been repeated the maximum number of times, the pressure testing protocol 550 will proceed from step 566 to 570. Step 570 is directed to providing at least some type of an indication that the pressure test of the corresponding pressure dome 330 has failed (e.g., by presenting a message on a display 206d of the photopheresis system 200—FIG. 2H). The pressure testing protocol 550 will then be terminated pursuant to step 572. It should be appreciated that the pressure testing protocol 550 could be configured to proceed directly to step 566 upon failure of either of the tests associated with steps 554 and 556 (e.g., the pressure testing protocol 550 could be configured so as to not perform step 556 if the low negative pressure test of step 554 failed).

The pressure testing protocol 550 also utilizes a pair of high value negative and high value positive pressure tests for a given pressure dome, assuming passage of each of the corresponding low value negative pressure test (step 554) and low value positive pressure test (step 556). In this regard, the protocol 550 will proceed from step 558 to one of step 560 or step 562 if the subject pressure dome 330 passed both the low value negative pressure test (step 554) and the low value positive pressure test (step 556). The high value negative and positive pressure tests associated with respective steps 560 and 562 of the pressure testing protocol 550 may be performed in any order.

In step 560 of the pressure testing protocol 550, a high value negative pressure is applied to the flow chamber 336 of the pressure dome 330 (to generate a second vacuum). This may be accomplished by operating a pump connected to one of the flow ports 338a, 338b of the pressure dome 330, while having a valve associated with the other of the flow ports 338a, 338b being closed. For instance, a corresponding peristaltic pump may be rotated a predetermined times, and which should generate a certain high value negative pressure in the flow chamber 336 of the pressure dome 330. If such a high value negative pressure is not generated in the flow chamber 336 (via an output from the pressure transducer 342), the corresponding high-value negative pressure test may be characterized as failing (step 564 of the pressure testing protocol 550). In one embodiment, the negative pressure that should be produced pursuant to step 560 is about −330 mmHG for the pressure dome associated with the patient collect line 242, is about −330 mmHG for the pressure dome associated with the patient return line 272, and is about −660 mmHG for the pressure dome associated with the centrifuge inlet line 211.

The vacuum that is generated pursuant to step 560 is larger than the vacuum that is generated pursuant to step 554 for the pressure testing protocol 550. A "larger vacuum" means a larger numerical value of negative pressure.

In step 564 of the pressure testing protocol 550, a high value positive pressure is applied to the flow chamber 336 of the pressure dome 330. This may be accomplished by operating a pump connected to one of the flow ports 338a, 338b of the pressure dome 330, while having a valve associated with the other of the flow ports 338a, 338b being closed. For instance, a corresponding peristaltic pump may be rotated a predetermined times, and which should generate a certain high positive pressure in the flow chamber 336 of the pressure dome 330. If such a high positive pressure is not generated in the flow chamber 336 (via an output from the pressure transducer 342), the corresponding high value positive pressure test may be characterized as failing (step 564 of the pressure testing protocol 550). In one embodiment, the positive pressure that should be produced pursuant to step 556 is about +330 mmHG for the pressure dome associated with the patient collect line 242, is about +330 mmHG for the pressure dome associated with the patient return line 272, and is about +660 mmHG for the pressure dome associated with the centrifuge inlet line 211.

If either of the high value negative or low positive pressure tests of the pressure dome 330 fail, the pressure testing protocol 550 may be configured to proceed from step 564 to step 570. Step 570 is again directed to providing at least some type of an indication that the pressure test of the corresponding pressure dome 330 has failed (e.g., by presenting a message on a display 206d of the photopheresis system 200—FIG. 2H). The pressure testing protocol 550 will then be terminated pursuant to step 572. It should be appreciated that the pressure testing protocol 550 could be configured to proceed directly to step 570 upon failure of either of the tests associated with steps 560 and 562 (e.g., the pressure testing protocol 550 could be configured so as to not perform step 562 if the high value negative pressure test of step 560 failed).

Displacing Fluid Using Elasticity and Centrifugal Force of a Centrifuge Bowl

As indicated above, centrifuge systems may be used to separate components of a particular fluid, such a separating whole blood into red blood cells, buffy coat, and plasma. Stopping and/or slowing the centrifuge may force a fluid out of the centrifuge bowl, such as one of the fluids separated by the centrifuge. For example, the elasticity and centrifugal force of the bowl may be used to displace the separated fluid. In some embodiments, this can be used to separate buffy coat from the rest of the blood components. This may result in a reduced treatment volume, which corresponds to less blood that must be collected in order to harvest the same amount of buffy coat.

An embodiment of a protocol for removing blood components from a centrifuge bowl is presented in FIG. 7. By way of initial summary and as shown in FIG. 7 for the case of a protocol 581, a spinning centrifuge may be slowed down or stopped while the inlet valve(s) are closed, and the outlet valve(s) may be opened, where the outlet valve(s) lead to collection bags (583). When a centrifuge bowl spins at high speeds, the bowl expands as a result of centrifugal force, and as the spinning slows, the centrifuge bowl contracts towards its original (pre-spin) size. When the bowl contracts, pressure on the fluid within the bowl increases, and therefore fluid is pushed out of the bowl, through the outlet(s), and into the collection bag(s).

Accordingly, when the fluid is separated whole blood, for example, buffy coat can be pushed out of the bowl and into a buffy coat collection bag via such functionality (585). Hematocrit (volume percentage of red blood cells in blood, "HCT") of the fluid displacement may be measured using an HCT sensor (587). If the HCT levels of the fluid are less than a predetermined level (589), such as about 18%, the centrifuge is slowed further (or stopped), therefore causing the bowl to contract further and force additional buffy coat out of the bowl and into the collection bag (583; 585). If the HCT levels of the fluid are greater than (or equal to) the predetermined level (589), the outlet valve may be closed in order to stop fluid displacement into the collection bag and divert the remaining volume to the return bag (591), and the protocol 581 may be terminated (593).

Figure 7A:
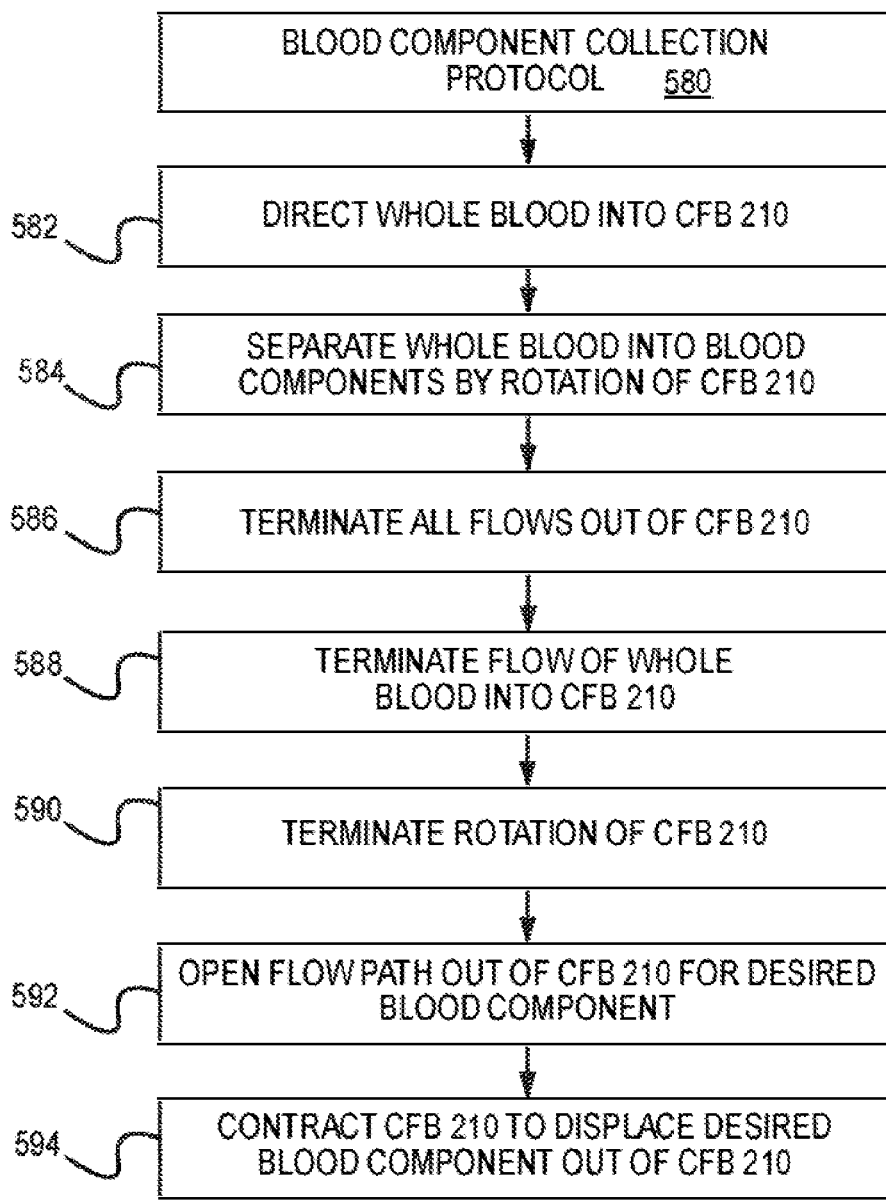
FIG. 7A is an embodiment of a blood component collection protocol that uses contraction of a centrifuge to displace a desired blood component from the centrifuge.

One embodiment of a blood component collection protocol is illustrated in FIG. 7A and is identified by reference numeral 580. Whole blood is directed into the centrifuge bowl 210 pursuant to step 582. For instance, the collection pump 248 may be operated to withdraw blood from the patient 310 (via the collect access 312), and direct the blood through the patient collect line 242, through the whole blood inlet passage 218 of the centrifuge bowl 210, and into the space 216 between the outer housing 212 and inner core 214 of the centrifuge bowl 210. The whole blood may be separated into a plurality of different blood components by rotation of the centrifuge bowl 210 (step 584). The centrifuge bowl 210 may be rotated at a speed and/or for a time duration such that an appropriate density gradient develops within the centrifuge bowl 210.

Once a desired amount of whole blood has been processed, all flows out of the centrifuge bowl 210 may be terminated (step 586) and the flow of whole blood into the centrifuge bowl 210 may be terminated as well (step 588). For instance, operation of the collect pump 248 may be terminated, operation of the red blood cell pump 228 may be terminated, and the return bag top valve 274a and the treatment bag inlet valve 284a may each be disposed in the closed position. Steps 586 and 588 could be simultaneously executed. Alternatively, step 588 could be executed prior to the execution of step 586.

After the centrifuge bowl 210 has been fluidly isolated from the remainder of the photopheresis system 200, rotation of the centrifuge bowl 210 may be terminated pursuant to step 590 of the blood component collection protocol 580. At some point in time during the reduction of the rotational speed of the centrifuge bowl 210 (pursuant to step 590), the flow path out of the centrifuge bowl 210 for the desired blood component may be opened (step 592). In the case where the desired blood component is buffy coat, the treatment bag inlet valve 284a may be opened (moreover, at least certain aspects of the buffy coat collection protocols addressed below in relation to FIG. 8 et al may be utilized (for instance, to determine when to acquire a hematocrit or plasma offset value 606 (e.g., step 632 of the protocol 600 of FIG. 8 may be used by the protocol 580 of FIG. 7A), when to terminate the collection of buffy coat based upon the hematocrit value of the flow into the treatment bag 280 (e.g., steps 634-652 of the protocol of 600 FIG. 8 may be used by the protocol 580 of FIG. 7A), or both). As the rotational speed of the centrifuge bowl 210 is reduced, the centrifuge bowl 210 should contract. This contraction of the centrifuge bowl 210 may be used to displace the desired blood component out of the centrifuge bowl 210 (step 594). In one embodiment, this contraction is the only motive force that is used to displace the desired blood component out of the centrifuge bowl 210.

Harvesting Buffy Coat

A number of different protocols may be used by a photopheresis system in relation to the collection of buffy coat, and that will now be addressed.

One embodiment of a buffy coat collection protocol is illustrated in FIG. 8 (FIG. 8 has been split into two separate sheets and that are identified as FIG. 8/1 and FIG. 8/2), and is identified by reference numeral 600. Step 610 is directed to directing whole blood into the centrifuge bowl 210 (e.g., operating the collect pump 248 to withdraw blood from the patient 310 and to direct this blood through the collect line 242, through the whole blood inlet passage 218 of the centrifuge bowl 210, and into the space between the outer housing 212 and inner core 214 of the centrifuge bowl 210). An air purge operation may be initiated pursuant to step 612 (e.g., through execution of the air purge protocol 460 of FIG. 4).

After completion of the air purge operation from step 612, whole blood is collected from the patient 310 and is directed into the centrifuge bowl 210 in the above-noted manner to separate the blood into its various blood components. In this regard, the centrifuge bowl 210 may be rotated at a user-specified speed (or at a default established by the photopheresis system 200) pursuant to execution of step 614 of the protocol 600 and as the buffy coat is allowed to accumulate in the centrifuge bowl 210. There may be instances where it may be desirable to change the rotational speed of the centrifuge bowl 210. The photopheresis system 200 may monitor for any such change in the rotational speed of the centrifuge bowl 210 (step 616). In the event of a change of speed, the flow of whole blood from the patient 310 into the centrifuge bowl 210 may be suspended (turning off the collect pump 248) and the centrifuge bowl 210 may be allowed to rotate at the updated rotational speed for a predetermined amount of time pursuant to step 618 (e.g., 120 seconds).

The protocol 600 will reach step 620, either from step 616 or from step 618. Step 620 is directed to determining if a certain amount of whole blood has been processed by the photopheresis system 200. In one embodiment, buffy coat is allowed to accumulate in the centrifuge bowl 210 based upon the amount of whole blood that has been processed or withdrawn from the patient 310. In this regard, step 620 is directed to determining if the amount of whole blood that has been processed is greater than a target value (entered by a user or operator of the photopheresis system 200 (user/data input device 206g (FIG. 2H) or a default value of the photopheresis system 200), less a predetermined amount (e.g., 75 ml). If the whole blood threshold associated with step 620 is not satisfied, the protocol 600 proceeds to step 626. Step 626 is directed to determining if the amount of whole blood that has been processed is greater than or equal to the noted target value (entered by a user or operator of the photopheresis system 200, or a default value of the photopheresis system 200), less the same predetermined amount from step 620 (e.g., 75 ml). If the whole blood threshold associated with step 626 is not satisfied, the protocol 600 returns to step 614 for repetition in accordance with the foregoing. Otherwise, the protocol 600 proceeds from step 626 to step 628.

Step 626 of the protocol 600 is reached if the whole blood processed threshold of step 620 is not satisfied. If the whole blood processed threshold of step 620 is satisfied, the protocol 600 proceeds instead from step 620 to step 622. Step 622 is directed toward determining if the centrifuge bowl 210 is at a desired or predetermined rotational speed, such as 4800 RPM. If the centrifuge bowl 210 is not being rotated at the desired/predetermined rotational speed in preparation for buffy coat collection, the protocol 600 initiates rotation of the centrifuge bowl 210 at the desired/predetermined rotational speed through execution of step 624. In order to allow the conditions in the centrifuge bowl 210 to in effect reach a steady state condition for the case of an increase in the rotational speed of the centrifuge bowl 210, the protocol 600 may be configured to allow the centrifuge bowl 210 to be rotated at the adjusted rotational speed for an appropriate period of time, such as 180 seconds (step 624). Any execution of step 622 and step 624 of the protocol 600 will ultimately result in the protocol 600 proceeding to the above-noted step 626. During any pause pursuant to step 624, the flow of whole blood from the patient 310 into the centrifuge bowl 210 may be suspended (by turning off the collect pump 248).

Step 626 again is directed to determining if the amount of whole blood that has been processed is greater than or equal to the noted target value (entered by a user or operator of the photopheresis system 200, or a default value of the photopheresis system 200), less the same predetermined amount associated with step 620 (e.g., 75 ml). If the whole blood threshold associated with step 626 is satisfied, the protocol 600 proceeds from step 626 to step 628. Pursuant to step 628, operation of the red blood cell pump 228 is terminated while whole blood continues to be withdrawn from the patient 310 and directed into the centrifuge bowl 210 in the above-noted manner via operation of the collect pump 248.

Step 630 of the protocol 600 of FIG. 8 allows buffy coat collection to be initiated if a first condition exists, if a second condition exists, or both. Buffy coat collection may be initiated if the bowl optic sensor or BOS signal 602 from the bowl optic sensor 930 (FIG. 10) corresponds with or satisfies a bowl optic sensor or BOS threshold 604. The BOS threshold 604 corresponds with the interface between the buffy coat and the red blood cells being at a desired position within the centrifuge bowl 210 and relative to its rotational axis 940. If the BOS signal 602 from the bowl optic sensor 930 satisfies the BOS threshold 604, the protocol 600 proceeds from step 630 to step 632.

The interface between the buffy coat and the whole blood cells may not reach the desired position within the centrifuge bowl 210 in a timely fashion and/or in all circumstances. For these situations (e.g., to reduce the potential of the patient 310 being subjected to the photopheresis process for an undesired amount of time), the protocol 600 includes another option in step 630 for proceeding to step 632. In the event that the amount of whole blood that has been processed is greater than or equal to the target amount of whole blood to be processed, plus another predetermined amount (e.g., 75 ml), the protocol 600 will also proceed from step 630 to step 632 (even if the interface between the buffy coat and the red blood cells within the centrifuge bowl 210 is not at the desired location relative to its rotational axis 940). If neither of the conditions associated with step 630 are satisfied, the protocol 600 returns control to step 628 for repetition in accordance with the foregoing.

Buffy coat from the centrifuge bowl 210 is directed into the treatment bag 280 for a "buffy coat collection" (via the plasma/buffy coat outlet passage 222 of the centrifuge bowl 210, and the plasma/buffy coat outlet line 230 that extends between the centrifuge bowl 210 and the treatment bag 280). One way to terminate the buffy coat collection is based upon the amount of hematocrit in this flow to the treatment bag 280. The initial flow that is discharged from the centrifuge bowl 210 and directed into the treatment bag 280 may have an elevated hematocrit. In order for this to not adversely impact the buffy coat collection to an undesired degree, step 632 of the protocol 600 allows a certain amount of buffy coat from the centrifuge bowl 210 (e.g., 10 ml) to be discharged into the treatment bag 280 before acquiring a plasma or hematocrit offset value 606. This hematocrit offset value 606 is used in relation to various aspects of the buffy coat collection. "Normal" plasma would have a hematocrit offset value 606 of "zero." Abnormal plasma may have a hematocrit offset value 606 of greater than zero. Hematocrit offset values 606 for abnormal blood may be on the order of 1-5%.

Step 634 of the protocol 600 indicates that the buffy coat collection is initiated, although it should be appreciated that the collection referred to in step 632 and the collection referred to in step 634 are each directed into the treatment bag 280 (i.e., both may be referred to as "buffy coat"). For each of step 632 and step 634, whole blood from the patient 310 is directed into the centrifuge bowl 210 (through the whole blood inlet passage 218 of the centrifuge bowl 210) to "push" the buffy coat out of the centrifuge bowl 210 through the plasma/buffy coat outlet passage 222, into/ through the plasma/buffy coat outline line 230, and into the treatment bag 280 (see FIG. 8D).

As discussed above, a hematocrit sensor is disposed in the flowpath from the centrifuge bowl 210 to the treatment bag 280. After a certain volume has been directed into the treatment bag 280 (step 632), the amount of hematocrit in the flow to the treatment bag 280 is determined (from an output of a hematocrit sensor, such as sensor 1125 discussed above) and is used by the protocol 600 as a hematocrit offset value 606. In this regard, step 636 is directed to determining if the hematocrit is greater than or equal to the plasma offset value 606, plus an additional predetermined amount (e.g. 5%). The ultimate value associated with step 636 may be viewed as a first hematocrit threshold. If the threshold associated with step 636 is not satisfied, the protocol 660 proceeds from step 636 to step 638. Step 638 is directed to determining if the hematocrit in the buffy coat (being directed into the treatment bag 280) is greater than or equal to a certain predetermined percentage (e.g., 10%). The predetermined value associated with step 638 may be viewed as a second hematocrit threshold. If the threshold associated with step 638 is satisfied, the protocol 600 proceeds from step 638 to step 640. Otherwise, the protocol 600 returns back to step 634 for repetition in accordance with the foregoing.

Step 638 in effect puts a "hard cap" on the hematocrit before changing how buffy coat is "pushed" out of the centrifuge bowl 210. If the hematocrit in the flow being directed into the treatment bag 280 satisfies the threshold associated with step 638, or if the hematocrit in the flow being directed into the treatment bag 280 satisfies the threshold associated with step 636, the protocol proceeds to step 640. Step 640 is directed to pausing the procedure for a certain amount of time, such as 120 seconds. During this pause, buffy coat is not being discharged from the centrifuge bowl 210—the operation of the collect pump 248 is suspended/terminated such that whole blood should no longer be "pushing" buffy coat out of the centrifuge bowl 210.

Elutriation is initiated in step 642 of the protocol 600 of FIG. 8, which is another mode of discharging buffy coat out of the centrifuge bowl 210. The elutriation referred to in step 642 pertains to operating the red blood cell pump 228 to direct contents out of the bottom of the return bag 270 (e.g., red blood cells) and back into the centrifuge bowl 210 through the red blood cell line 226 and then into/through the red blood cell passage 220 of the centrifuge bowl 210. In one embodiment, the flow rate from the return bag 270 into the centrifuge bowl 210 is 10 ml/min. The elutriation of step 642 is of limited duration. In this regard, step 644 is directed to determining if a certain amount of contents from the return bag 270 have been directed into the centrifuge bowl 210 in the manner discussed for step 642 (e.g., 20 ml). If the threshold associated with step 644 has not been satisfied, the protocol 600 proceeds from step 644 to step 646.

Step 646 includes yet another hematocrit threshold (e.g., a third hematocrit threshold). The hematocrit threshold associated with step 646 is higher than the hematocrit threshold associated with step 638. If the hematocrit threshold of step 646 is satisfied (e.g., if the hematocrit of the flow into the treatment bag 280 is greater than or equal to a predetermined amount, such as 24%), the protocol 600 proceeds from step 646 to step 652 where the protocol 600 is terminated. Otherwise, the protocol 600 proceeds from step 646 to step 642 for repetition in accordance with the foregoing. Once the elutriation threshold associated with step 644 has been satisfied (e.g., if at least 20 ml has been elutriated), the protocol 600 proceeds from step 644 to step 648. Step 648 indicates that "buffy coat collection is resumed," which means that instead of red blood cells being used to "push" the buffy coat out of the centrifuge bowl 210 (the elutriation of step 642), whole blood from the patient 310 is once again directed into the centrifuge bowl 210 and in the above-noted manner to discharge buffy out of the centrifuge bowl 210.

Once the flow of whole blood into the centrifuge bowl 210 has been reinitiated (via operation of the collect pump 248 and pursuant to step 648), the protocol 600 monitors for the existence of a pair of conditions. In the event that the hematocrit percentage of the flow into the treatment bag 280 satisfies a fourth hematocrit threshold (e.g., 24%), the protocol 600 proceeds from step 650 to step 652 where the protocol 600 is then terminated. The hematocrit percentage or hematocrit threshold may be the same for each of steps 646 and 650, as noted on FIG. 8. In the event that an additional predetermined amount of whole blood has been withdrawn from the patient 310 after the elutriation has been terminated and the flow of whole blood back into the centrifuge bowl 210 has been reinitiated (e.g., 10 ml of additional whole blood from the patient 310), the protocol 600 also proceeds from step 650 to step 652 to terminate the protocol 660.

Figure 8A:
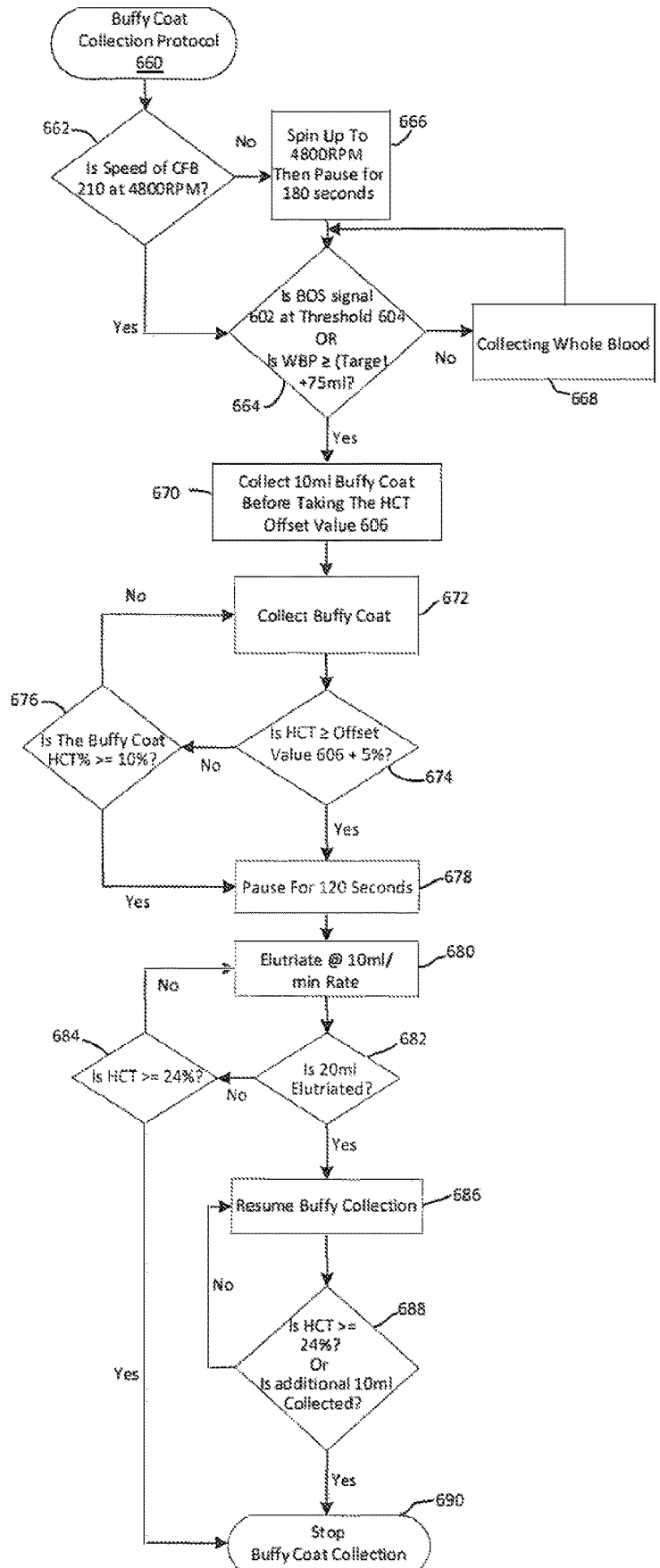
FIG. 8A is one embodiment of a buffy coat collection protocol that may be used by a photopheresis system for conducting a photopheresis procedure on abnormal blood.

Another embodiment of a buffy coat collection protocol is illustrated in FIG. 8A, is identified by reference numeral 660, and includes features to accommodate the processing of abnormal blood, for instance whole blood having high/elevated lipids or high/elevated bilirubin. "Abnormal" in relation to the blood from the patient 310 may also mean that the plasma from the patient 310 is "darker" plasma, and which may adversely impact hematocrit readings used by the photopheresis system 200 in relation to the collection of buffy coat.

The buffy coat collection protocol 660 may utilize a step 662 that is directed toward determining if the centrifuge bowl 210 is at a desired or predetermined rotational speed, such as 4800 RPM. If the centrifuge bowl 210 is not being rotated at the desired/predetermined rotational speed in preparation for buffy coat collection, the protocol 660 initiates rotation of the centrifuge bowl 210 at the desired/predetermined rotational speed through execution of step 666. As noted and to allow the conditions in the centrifuge bowl 210 to in effect reach a steady state condition for the case of an increase in the rotational speed of the centrifuge bowl 210, the protocol 660 may be configured to allow the centrifuge bowl 210 to be rotated at the adjusted rotational speed for an appropriate period of time, such as 180 seconds (step 666). In either case, the protocol 660 will reach step 664 and which may be viewed as a trigger for initiating the collection of buffy coat from the centrifuge bowl 210 (through the plasma/buffy coat passage 222 and the plasma/buffy coat line 230.

Step 664 of the FIG. 8A protocol 660 allows buffy coat collection to be initiated if a first condition exists, if a second condition exists, or both. Buffy coat collection may be initiated if the bowl optic sensor or BOS signal 602 from the bowl optic sensor 930 corresponds with or satisfies a bowl optic sensor or BOS threshold 604. The BOS threshold 604 corresponds with the interface between the buffy coat and the red blood cells being at a desired position within the centrifuge bowl 210 and relative to its rotational axis 940. If the BOS signal 602 from the bowl optic sensor 930 satisfies the BOS threshold 604, then the protocol 660 proceeds from step 664 to step 670.

The interface between the buffy coat and the whole blood cells may not reach the desired position within the centrifuge bowl 210 in a timely fashion and/or in all circumstances. For these situations (e.g., to reduce the potential of the patient 310 being subjected to the photopheresis process for an undesired amount of time), the protocol 660 includes another option in step 664 for proceeding to step 670. In the event that the amount of whole blood that has been processed is greater than or equal to the target amount of whole blood to be processed, plus another predetermined amount (e.g., 75 ml), the protocol 660 will also proceed from step 664 to 670 (even if the interface between the buffy coat and the red blood cells within the centrifuge bowl 210 is not at the desired location relative to its rotational axis 940).

Buffy coat from the centrifuge bowl 210 is directed into the treatment bag 280 for a "buffy coat collection" (via the plasma/buffy coat outlet passage 222 of the centrifuge bowl 210, and the plasma/buffy coat outlet line 230). One way to terminate the buffy coat collection is based upon the amount of hematocrit in this flow to the treatment bag 280. The initial flow that is discharged from the centrifuge bowl 210 and directed into the treatment bag 280 may have an elevated hematocrit. In order for this to not adversely impact the buffy coat collection to an undesired degree, step 670 of the protocol 660 allows a certain amount of buffy coat from the centrifuge bowl 210 (e.g., 10 ml) to be discharged into the treatment bag 280 before acquiring a plasma or hematocrit offset value 606 (step 670). This hematocrit offset value 606 is used in a number of aspects of the buffy coat collection. "Normal" plasma would have a hematocrit offset value 606 of "zero." Abnormal plasma may have a hematocrit offset value 606 of greater than zero. Hematocrit offset values 606 for abnormal blood may be on the order of 1-5%.

Step 672 of the protocol 660 indicates that the buffy coat collection is initiated, although it should be appreciated that the collection referred to in step 670 and the collection referred to in step 672 are each directed into the treatment bag 280 (i.e., both may be referred to as "buffy coat"). For each of step 670 and step 672, whole blood from the patient 310 is directed into the centrifuge bowl 210 (through the whole blood inlet passage 218 of the centrifuge bowl 210) to "push" the buffy coat out of the centrifuge bowl 210 through the plasma/buffy coat outlet passage 222, into/through the plasma/buffy coat outline line 230, and into the treatment bag 280.

As discussed above, a hematocrit sensor is disposed in the flowpath from the centrifuge bowl 210 to the treatment bag 280. After a certain volume has been directed into the treatment bag 280 (step 670), the amount of hematocrit in the flow to the treatment bag 280 is determined (from an output of a hematocrit sensor, such as sensor 1125 discussed above) and is used as a hematocrit offset value 606 by the protocol 660. In this regard, step 674 is directed to determining if the hematocrit is greater than or equal to the hematocrit offset value 606, plus an additional predetermined amount (e.g. 5%). The ultimate value associated with step 674 may be viewed as a first hematocrit threshold. If the threshold associated with step 674 is not satisfied, the protocol 660 proceeds to step 676. Step 676 is directed to determining if the hematocrit in the buffy coat (being directed into the treatment bag 280) is greater than or equal to a certain predetermined percentage (e.g., 10%). The predetermined value associated with step 676 may be viewed as a second hematocrit threshold. If the threshold associated with step 676 is met, the protocol 660 proceeds from step 676 to step 678. Otherwise, the protocol proceeds back to step 672 for repetition in accordance with the foregoing.

Step 676 in effect puts a "hard cap" on the hematocrit before changing how buffy coat is "pushed" out of the centrifuge bowl 210. If the hematocrit in the flow being directed into the treatment bag 280 satisfies the threshold associated with step 674, or if the hematocrit in the flow being directed into the treatment bag 280 satisfies the threshold associated with step 676, the protocol proceeds to step 678. Step 678 is directed to pausing the procedure for a certain amount of time, such as 120 seconds. During this pause, buffy coat is not being discharged from the centrifuge bowl 210—the operation of the collect pump 248 is terminated such that whole blood should no longer be "pushing" buffy coat out of the centrifuge bowl 210.

Elutriation is initiated in step 680 of the protocol 660 of FIG. 8A, which is another mode of discharging buffy coat out of the centrifuge bowl 210. The elutriation referred to in step 680 pertains to operating the red blood cell pump 228 to direct contents out of the bottom of the return bag 270 (e.g., red blood cells) and back into the centrifuge bowl 210 through the red blood cell line 226 and then into/through the red blood cell passage 220 of the centrifuge bowl 210. In one embodiment, the flow rate from the return bag 270 into the centrifuge bowl 210 is about 10 ml/min. Elutriation in accordance with step 680 is of a limited duration. In this regard, step 682 is directed to determining if a certain amount of contents from the return bag 270 have been directed into the centrifuge bowl 210 in the manner discussed for step 680 (e.g., 20 ml). If the threshold associated with step 682 has not been satisfied, the protocol 660 proceeds from step 682 to step 684.

Step 684 includes yet another hematocrit threshold (e.g., a third hematocrit threshold). The hematocrit threshold associated with step 684 is higher than the hematocrit threshold associated with step 676. If the hematocrit threshold of step 684 is satisfied (e.g., if the hematocrit of the flow into the treatment bag 280 is greater than or equal to a predetermined amount, such as 24%), the protocol 660 proceeds from step 684 to step 690 where the protocol 660 is terminated. Otherwise, the protocol 660 proceeds from step 684 to step 680 for repetition in accordance with the foregoing. Once the elutriation threshold associated with step 682 has been satisfied (e.g., if at least 20 ml has been elutriated), the protocol 660 proceeds from step 682 to step 686. Step 686 indicates that "buffy coat collection is resumed," which means that instead of red blood cells being used to "push" the buffy coat out of the centrifuge bowl 210 (the elutriation of step 680), whole blood from the patient 310 is once again directed into the centrifuge bowl 210 in the above-noted manner.

Once the flow of whole blood into the centrifuge bowl 210 has been reinitiated (via operation of the collect pump 248 and pursuant to step 686), the protocol 660 monitors for the existence of a pair of conditions. In the event that the hematocrit percentage of the flow into the treatment bag 280 satisfies a fourth hematocrit threshold (e.g., 24%), the protocol 660 proceeds from step 682 step 690 where the protocol 660 is then terminated. The hematocrit percentage may be the same for each of steps 684 and 688, as noted on FIG. 8A. In the event that an additional predetermined amount of whole blood has been withdrawn from the patient 310 after the elutriation has been terminated and the flow of whole blood back into the centrifuge bowl 210 has been reinitiated (e.g., 10 ml of additional whole blood from the patient 310), the protocol 660 proceeds from step 682 step 690 to terminate the protocol 660.

Figure 8B:
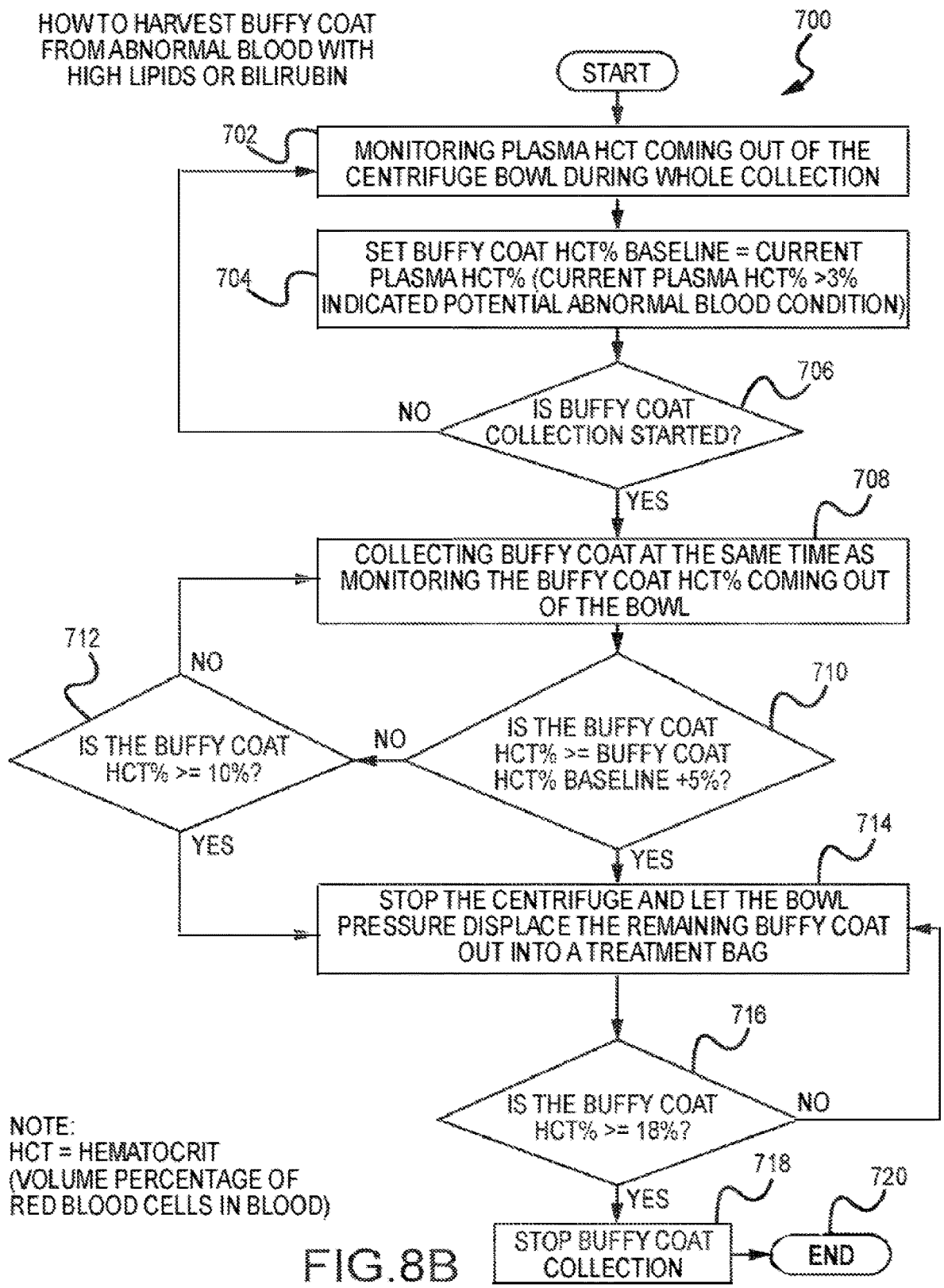
FIG. 8B is another embodiment of a buffy coat collection protocol that may be used by a photopheresis system for conducting a photopheresis procedure on abnormal blood, such as blood with high lipids of bilirubin.

In some embodiments, an effluent sensor may be used to determine plasma opacity, which in turn can be used to adjust and inform a buffy coat harvest algorithm in order to maximize cell yield and minimize red cell interference. This may be of particular importance when collecting cells from a patient with abnormal blood morphologies, such as high lipids or bilirubin. An exemplary flow chart is shown in FIG. 8B for the case of a buffy coat collection protocol 700.

HCT levels of plasma that comes out of the centrifuge bowl during whole collection may be monitored (702), and a buffy coat baseline HCT percentage may be set to be equal to (or approximately equal to) the current plasma HCT percentage (704). In some embodiments, a plasma HCT percentage of greater than about three percent (3%) may indicate a potential abnormal blood condition. The plasma HCT levels may be monitored, and the baseline buffy coat HCT percentage may be reset until the buffy coat collection has started (706). In some embodiments, the plasma HCT may be continuously measured, and the buffy coat baseline HCT percentage may be altered based on the continuous measurements.

As the buffy coat is collected (708), the buffy coat HCT percentage is monitored (e.g., as the buffy coat comes out of the bowl) in order to determine if the buffy coat HCT percentage is above a first threshold (710). The first threshold may be based on the buffy coat baseline HCT percentage, such as the baseline HCT percentage, plus five percent (5%). If the buffy coat HCT percentage does not exceed the first threshold (710), a determination is made as to whether the HCT percentage exceeds a second threshold (712). For example, the second threshold may be about ten percent (10%). If the HCT percentage does not exceed the second threshold, the buffy coat collection continues (708), and the HCT percentage of the buffy coat being discharged from the bowl will continue to be monitored in accordance with the foregoing.

If the buffy coat HCT percentage exceeds the first threshold (710), or if the buffy coat HCT percentage exceeds the second threshold (712), the centrifuge is stopped (or slowed) and the bowl pressure may displace (714) the remaining buffy coat into a treatment bag (or buffy coat may be directed out of the bowl in any other appropriate manner). The collection of buffy coat being discharged from the bowl may continue until the buffy coat HCT percentage is greater than a third threshold, such as about 18% (716). When the third threshold is reached, buffy coat collection may be stopped (718), and the protocol 700 may be terminated (720).

Figure 8C:
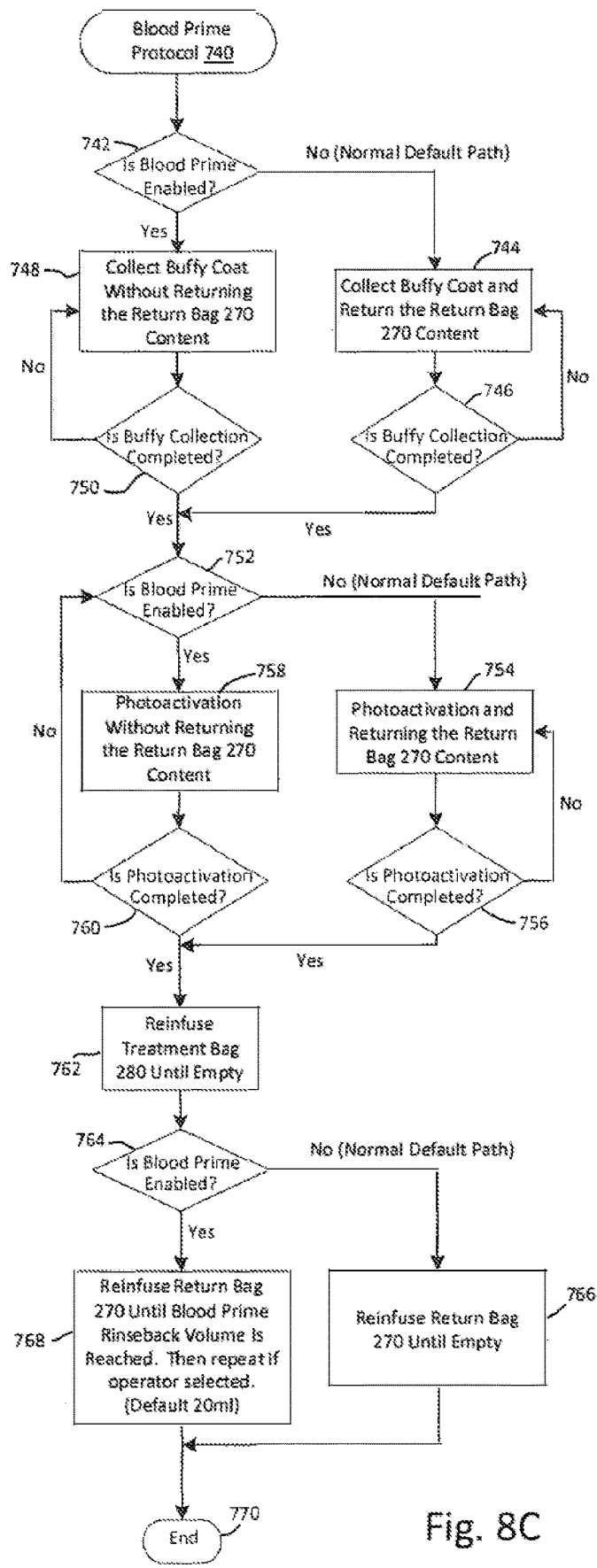
FIG. 8C is an embodiment of a buffy coat collection protocol that may be used by a photopheresis system and for the case of a blood prime.
Figure 8D:
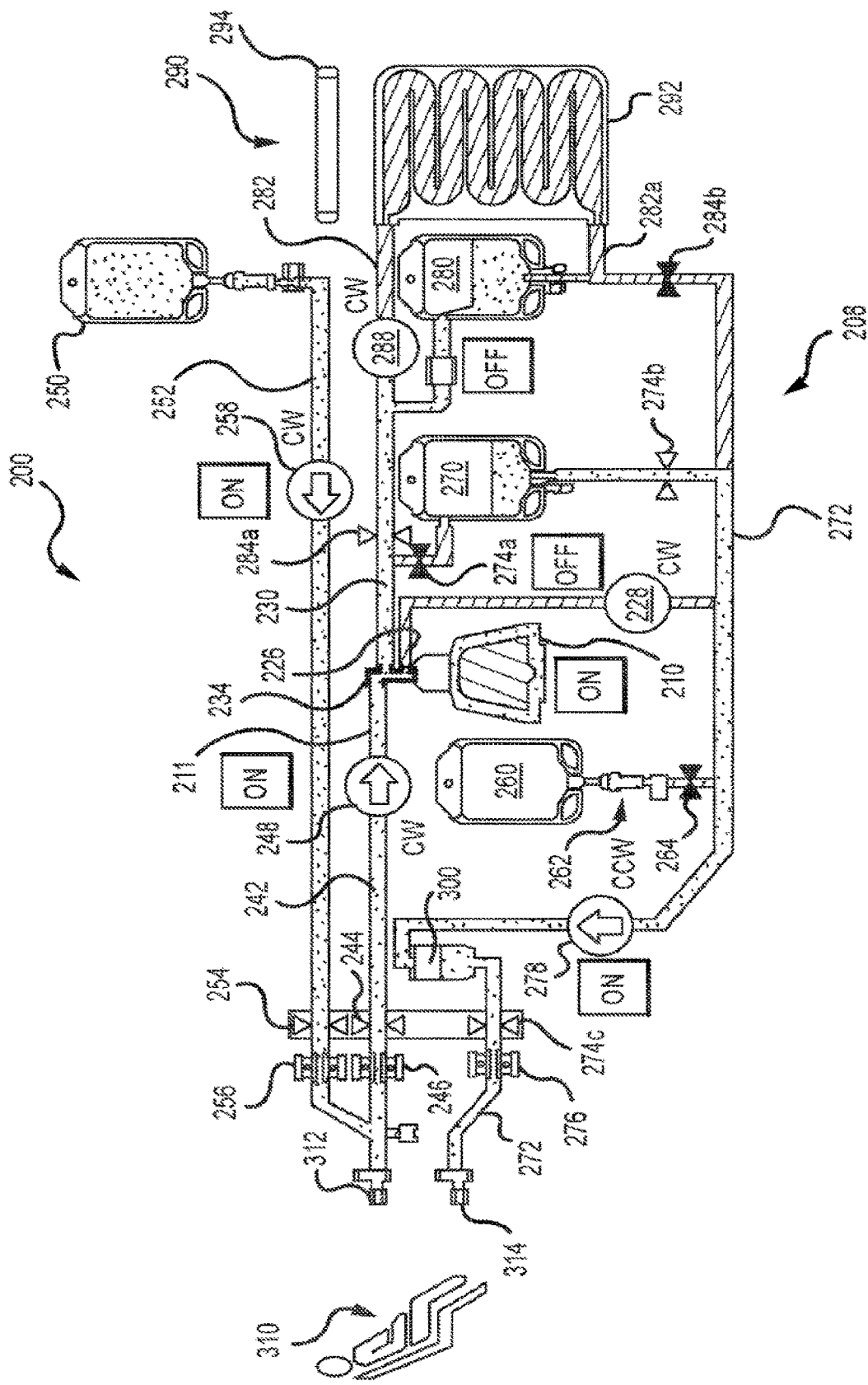
FIG. 8D is a fluid schematic of the photopheresis system shown in FIG. 2C, but in a configuration that exists during execution of a buffy coat collection protocol.

FIG. 8C presents an embodiment that addresses buffy coat collection for the case of a blood prime (where blood other than from the patient 310 is used to initially fill the centrifuge bowl 210), and which is identified by reference numeral 740. Initially, it should be noted that the photopheresis system 200 is itself configured to execute a blood prime. For instance, the photopheresis system 200 may be configured to present a blood prime option (e.g., by presenting a selectable blood prime option on a monitor or display 206d of the photopheresis system 200) to a user for selection (e.g., via a user/data input device 206g—FIG. 2H). Moreover, the selection or activation of a blood prime on the photopheresis system 200 initiates changes to three aspects of the overall photopheresis procedure—the collection of the buffy coat, the subsequent photoactivation of the collected buffy coat, and the reinfusion of the patient 310. The protocol 740 shows three separate steps regarding checking for blood prime enablement (steps 742, 752, and 762). It should be appreciated that the protocol 740 may be configured such that the photopheresis system 200 need only make this determination a single time.

Step 742 is directed to the photopheresis system 200 assessing whether a user or operator of the photopheresis system 200 has enabled a blood prime (e.g., through a user/data input device 206g—FIG. 2H). A blood prime option could be presented by the photopheresis system 200 on a setup screen (presented on a monitor or display 206d—FIG. 2H). If a blood prime has not been enabled, the protocol 740 proceeds from step 742 to step 744. Step 744 is directed to collecting buffy coat. The contents of the return bag 270 are returned to the patient 310 through operation of the return pump 278 as buffy coat is collected pursuant to step 744. Step 746 of the protocol 740 entails the photopheresis system 200 making a determination as to whether the buffy coat collection has been completed. Steps 744 and 746 may be at least generally in accordance with the corresponding portions of the collection protocol 600 of FIG. 8, the collection protocol 660 of FIG. 8A, and the protocol set forth in FIG. 8B.

A determination by the photopheresis system 200 that a blood prime feature has been enabled on the system 200 (step 742) causes the protocol 740 to proceed from step 742 to step 748. Buffy coat is collected pursuant to step 748. However and in the case of a blood prime, the photopheresis system 200 is configured such that the contents of the return bag 270 are not returned to the patient 310 during buffy coat collect (step 748). Steps 748 and 750 in relation to buffy coat collection and termination of the buffy coat collect may be at least generally in accordance with the corresponding portions of the collection protocol 600 of FIG. 8, the collection protocol 660 of FIG. 8A, and the protocol set forth in FIG. 8B.

Another aspect of a photopheresis procedure is photoactivation of the buffy coat that has been collected from the centrifuge bowl 210 and that is directed into the treatment bag 280. Step 752 is directed to the photopheresis system 200 assessing whether a user or operator of the photopheresis system 200 has enabled a blood prime (corresponding with step 742). If a blood prime has not been enabled, the protocol 740 proceeds from step 752 to step 754. Step 754 is directed to photoactivation of the buffy coat, where the contents of the treatment bag 280 are recirculated through the irradiation bag 292 while being exposed to the output of the light source(s) 294 of the photoactivation module 290. As this is happening, contents of the return bag 270 are also returned to the patient and as noted in step 754. Completion of photoactivation process is monitored for by the photopheresis system 200 pursuant to step 756.

A determination by the photopheresis system 200 that a blood prime feature has been enabled on the system 200 (step 752) causes the protocol 740 to proceed from step 752 to step 758. Photoactivation of the buffy coat is undertaken pursuant to step 758 (and in the manner described in step 754). However and in the case of a blood prime, the photopheresis system 200 is configured such that the contents of the return bag 270 are not returned to the patient 310 during photoactivation of the buffy coat (step 758). Completion of the photoactivation process is monitored for by the photopheresis system 200 pursuant to step 760.

Upon completion of buffy coat collection and the subsequent photoactivation of the collected buffy coat, the patient 310 is reinfused. Initially, the contents of the treatment bag 280 are reinfused to the patient 310 (step 762). Step 764 is directed to the photopheresis system 200 assessing whether a user or operator of the photopheresis system 200 has enabled a blood prime (corresponding with step 742). If a blood prime has not been enabled, the protocol 740 proceeds from step 764 to step 766. Step 766 is directed to returning the entire contents of the return bag 270 to the patient 310 through operation of the return pump 278.

A determination by the photopheresis system 200 that a blood prime feature has been enabled on the system 200 (step 764) causes the protocol 740 to proceed from step 764 to step 768. In the case of a blood prime, only a portion of the return bag 270 is reinfused to the patient 310 via operation of the return pump 278. More specifically and as part of the photopheresis system 200 being configured to accommodate a blood prime, if a blood prime feature of the system 200 is selected or activated by a user/operator, a related option is presented (e.g., on a display or monitor 206d of the system 200). This related option may be characterized as a rinseback volume—the volume to be returned to the patient 310 after the treatment bag 280 has already been returned to the patient 310. The photopheresis system 200 may include a default rinseback volume (e.g., 20 ml). Prior to starting the photopheresis procedure, a user/operator can input a desired rinseback volume to the photopheresis system 200 (e.g., via a user/data input device 206g—FIG. 2H). The photopheresis system 200 may also be configured to allow the user/operator to edit the rinseback volume at any time during the procedure (including during reinfusion of the patient via the return bag pursuant to step 768). A user/operator may also input a new rinseback volume after a preceding rinseback volume has been returned to the patient 310 from the return bag 270 and via operation of the return pump 278.

Optimizing Treatment Time and Methoxalen Dose for a Patient

Figure 9:
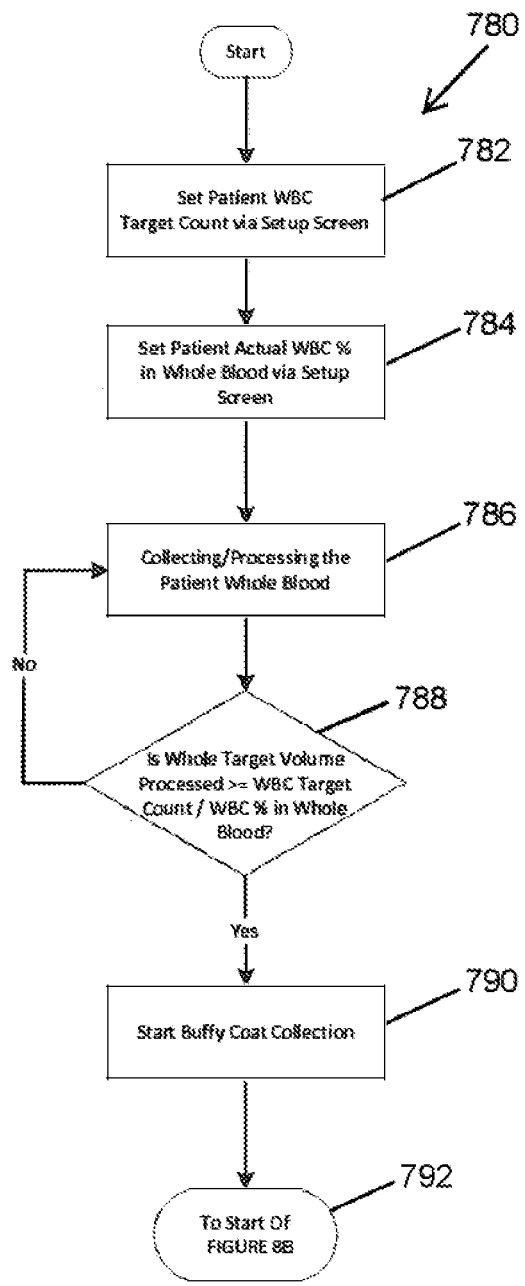
FIG. 9 is an embodiment of a protocol that may be used by a photopheresis system for optimizing therapy time and dosages based on a patient's white blood cell count.

Treatment time and/or a target dose (e.g., of Methoxalen) for a patient, may be optimized based on an individual patient's white blood cell count (which may be estimated based on the count at a previous donation). As shown in FIG. 9 for the case of a protocol 780, estimated target white blood cell yields may be set via a computer setup screen (782), and the patient's actual white blood cell percentage in whole blood may be entered (784). Once the values are set, the patient's whole blood may be collected and processed (786). A determination may be made as to whether the whole target volume processed is greater than or equal to the target white blood cell count and the white blood cell percentage in whole blood (788). If the target volume has not yet been achieved, collection and processing of the whole blood continues (786). When the target volume of whole blood has been collected and processed, buffy coat collection commences (790). In some embodiments, once the buffy coat collection begins, this may lead to the flow charts outlined above with respect to FIG. 8 et al. and/or the flow charts outlined above with respect to FIG. 7 et al, including FIG. 8B as noted (792).

Figure 9A:
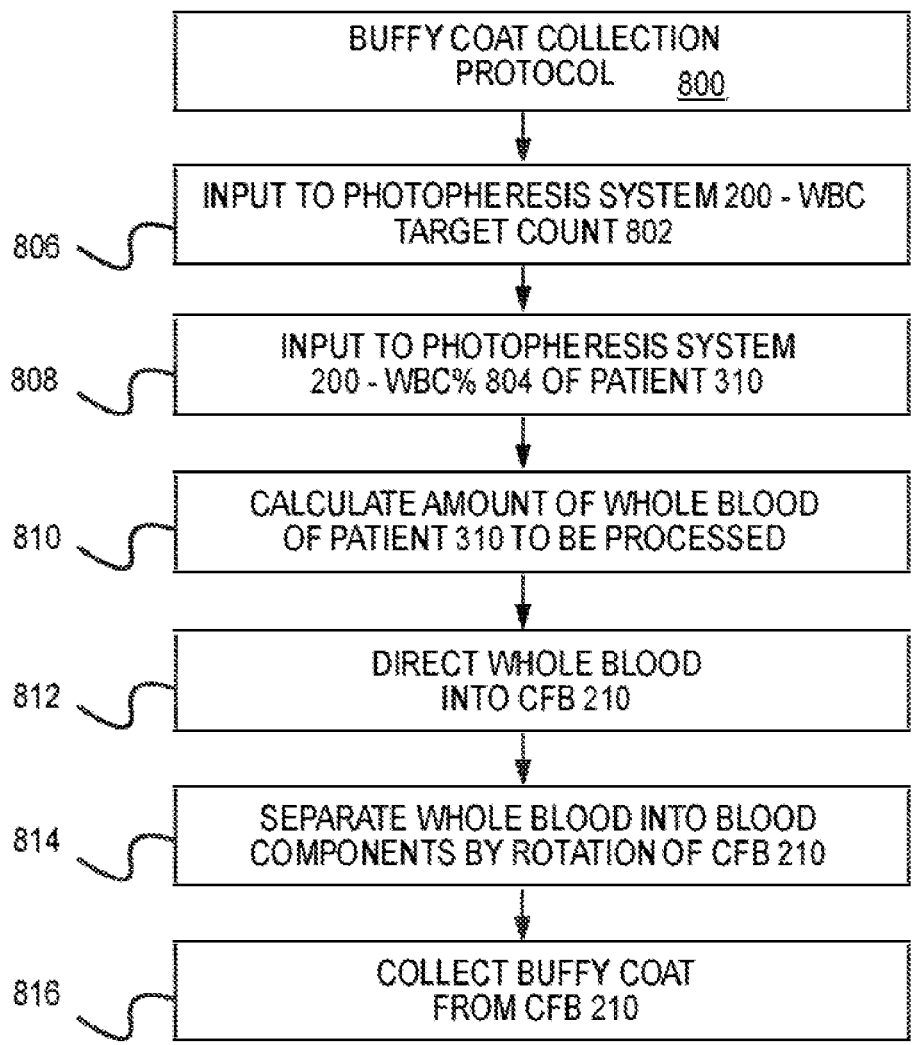
FIG. 9A is an embodiment of a buffy coat collection protocol that may be used by a photopheresis system and that determines the amount of whole blood that should be processed based upon patient data.

Another embodiment of a buffy coat collection protocol is illustrated in FIG. 9A, is identified by reference numeral 800, and may be characterized as an optimization of a buffy coat collection being executed by a photopheresis system. At least two inputs are provided to the photopheresis system 200 pursuant to the protocol buffy coat collection protocol 800, which may be input to the photopheresis system 200 in any appropriate manner (e.g., by an operator of the photopheresis system 200 using, for instance, a user/data input device 206g (FIG. 2H)), and which may be executed in any order. One of these inputs is a white blood cell or WBC target count 802 (step 806—a targeted amount of white blood cells to be collected by the photopheresis system 200 and "processed" by the photo-activation module 290 (e.g., subjected to phototherapy). Another of these inputs is the white blood cell or WBC percentage 804 of the patient 310 that is undergoing photopheresis (step 808)—the percentage of whole blood from the patient 310 that is defined by white blood cells. The WBC percentage 804 can be determined in any appropriate manner (e.g., empirically).

The amount of whole blood of a patient 310 that should be processed by the photopheresis system 200 may be calculated by the photopheresis system 200 using the inputs from steps 806 and 808 for purposes of the buffy coat collection protocol 800 (step 810). For instance, the WBC target count 802 (step 806) may be divided by the WBC percentage 804 of the patient 310 to acquire the volume of whole blood that should be withdrawn from the patient 310 and processed by the photopheresis system 200, all prior to initiating a buffy coat collection. In this regard, whole blood from the patient 810 is directed into the centrifuge bowl 210 of the photopheresis system 200 (step 812). The whole blood is separated into a plurality of blood components through rotation of the centrifuge bowl 210 (step 814). After the calculated volume of whole blood (step 810) has been withdrawn from the patient 310 and processed in the centrifuge bowl 210, the buffy coat collection 816 may be initiated (step 816). Buffy coat may be discharged from the centrifuge bowl 210 in any appropriate manner, including in accordance with any of the FIG. 8 et al. Buffy coat collection protocols.

Fluid Balance Reset for Blood Prime

In at least certain cases, it may be desirable to use donor blood to prime the disposable kit of the photopheresis system (versus using blood from the patient to prime the disposable kit). This may be referred to as a "blood prime." In the case of a blood prime, there may be a need to limit the amount of blood/blood components that should be returned to the patient after the contents of the treatment bag (the buffy coat that was subjected to phototherapy) has been returned to the patient.

After the photopheresis system (e.g., see incorporated by reference US Patent Publication No. 2010/0298752, noted above) is primed using donor blood, the operator may reset the patient extracorporeal fluid balance. This may provide an easier and more consistent fluid balance estimate of the patient. As shown in FIG. 10 for the case of a fluid balance reset protocol 820, fluid balance may be reset when a user touches a fluid balance indicator on the screen of the photopheresis system (821). In some embodiments, a user may need to press-and-hold the indicator for two seconds. A fluid balance reset dialog (or dialogue) may be displayed (822), which may, for example, indicate 'yes' or 'no' options. If the 'yes' option is selected (823), the fluid balance is set to zero (825) and the protocol 820 may be terminated (826). If the 'yes' option is not selected, a determination is made as to whether the 'no' option was selected (824). If the 'no' option was selected, the fluid balance is not reset and the protocol 820 may be terminated (826); if the 'no' option was not selected, the reset dialog may continue to be displayed until a 'yes' or 'no' option is selected. In some embodiments, the reset dialog may be removed from the display if an option is not selected within a predetermined amount of time, such as about 30 seconds, about 45 seconds, about a minute, or about five minutes.

Operator Identification

In some embodiments, the identification of an operator who is performing the photopheresis treatment may be captured, and the operator's identification may be recorded on a smart or diagnostic database. In some embodiments, this may be used to associate procedures with the operators who perform the procedure, which may be used for trend analysis and training. The information may also be used to determine best demonstrated practices.

Figure 11:
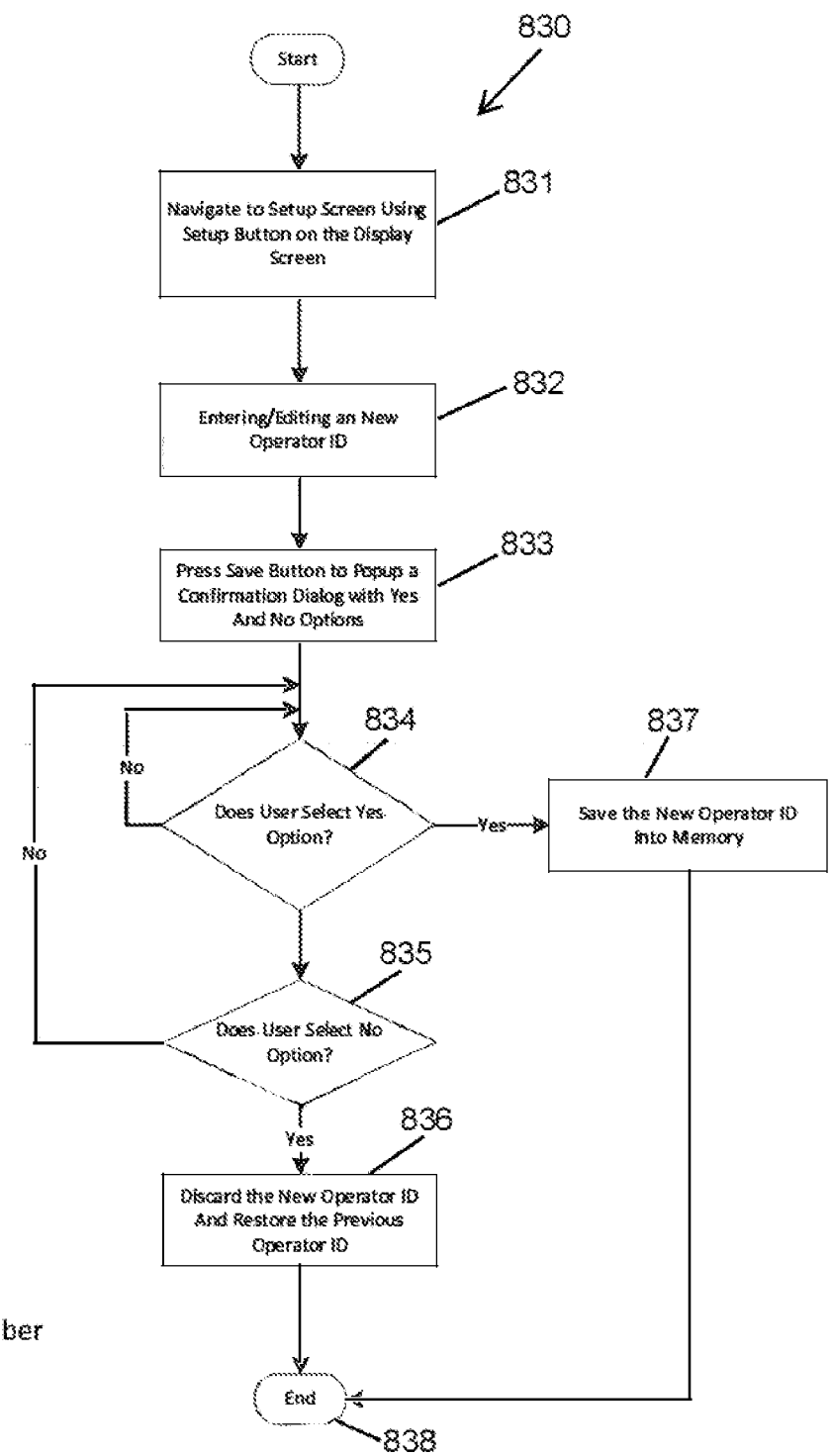
FIG. 11 is an embodiment of a protocol that may be used by a photopheresis system for capturing an operator identification.

The operator may be identified by swiping an identification card, by using a fingerprint scanner, or the like. The user may be asked to enter his or her username and/or password. For example, and as shown in FIG. 11 for the case of a protocol 830, a setup screen may be displayed, or an operator may navigate to a setup screen using a setup button on the display screen (831). The operator may enter and/or edit an operator identification number or "Operator ID" (832). In some embodiments, the operator may enter a new Operator ID, or previously used Operator IDs may be recognized. When the Operator ID is entered, the operator may press a save button (833), and a popup may be generated with a confirmation dialog, which may allow a user to confirm the Operator ID by pressing a 'yes' or 'no' option (834). If the user presses the 'yes' option (834), the Operator ID is saved into memory (837) and the protocol 830 may be terminated (838). If 'yes' is not selected (834), a determination is made as to whether the 'no' option was selected (835). If the 'no' option is selected, the Operator ID is discarded (836) and the protocol 830 may be terminated (838). In some embodiments, the operator may be given the option to enter a new Operator ID, and in other embodiments, the previous Operator ID may be restored. If the 'no' option was not selected, the reset dialog may continue to be displayed until a 'yes' or 'no' option is selected. In some embodiments, the reset dialog may be removed from the display if an option is not selected within a predetermined amount of time, such as about 30 seconds, about 45 seconds, about a minute, or about five minutes.

Adjusting Flow Rate Based on Pressure

Pressure may be monitored within the photopheresis system, and the pressure measurements may be used to adjust flow rate values to an optimal flow rate. In some embodiments, the optimal flow rate values may be different for the collection of the whole blood and for the return of the cells to the patient. For example, an operator may set the pressure limit for both the collection and the return, and the photopheresis system may automatically adjust the flow rate of collection and/or return based on the pressure limit(s). This may reduce the number of nuisance pressure alarms. The photopheresis system may be configured to allow this auto flow rate adjustment feature to be disabled.

Figure 12:
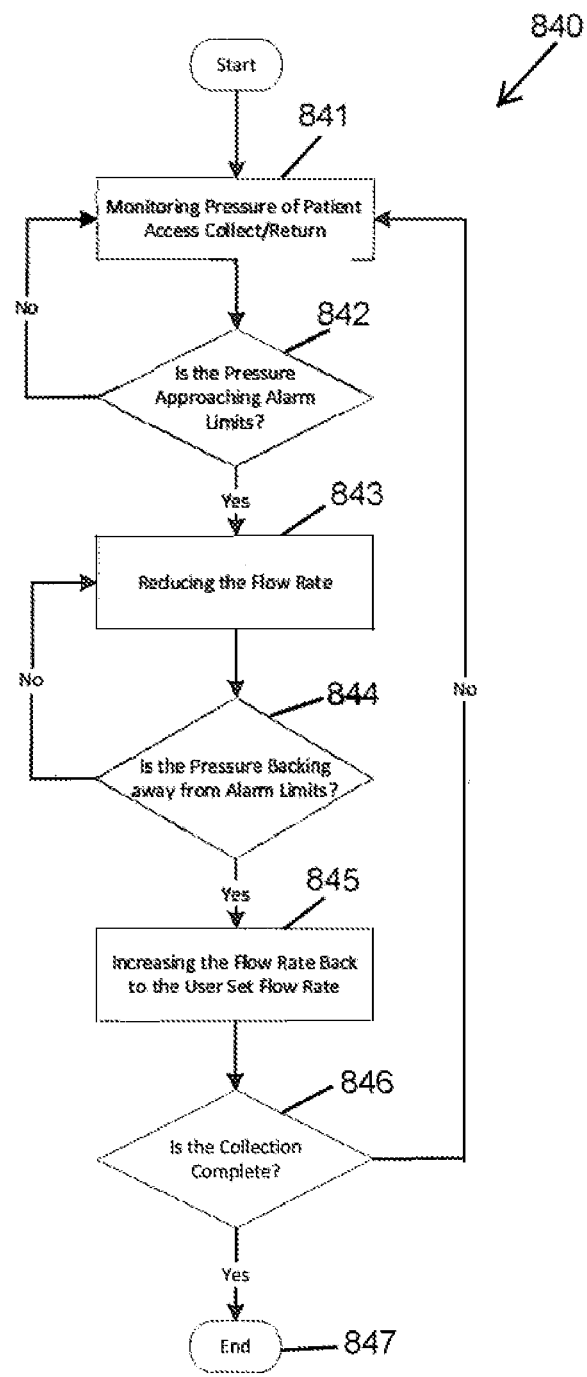
FIG. 12 is an embodiment of a protocol that may be used by a photopheresis system for adjusting flow rate based on pressure readings.

As shown in FIG. 12 for the case of a protocol 840, pressure of the collection and return may be monitored (841), and a determination is made as to whether the pressure is approaching limits (842). The limits may be set for a particular patient, or the limits may be preset default limits. As long as the pressure does not approach the limit(s), the pressure is continually monitored (841), either at discrete intervals (such as about every second, about every 5 seconds, etc.) or continuously. If the pressure does approach the limits (842), the flow rate is reduced (843). In some embodiments, the flow rate may be gradually reduced, while in other embodiments, the flow rate may be decreased by a set interval. The set interval may be predetermined by default settings, or the interval may be determined based on a formula that is a function of the pressure limits and the measured pressure.

As the flow rate is reduced, a determination is made as to whether the pressure is backing away from the limits (844). If not, the flow rate is further reduced (843) until the pressure reduces. If the pressure is backing away from the limits (844), the flow rate is increased back to the flow rate set based on the operator-set pressure limit (845). The pressure may be monitored, and if necessary, these steps may be repeated, until the collection is complete (846), at which point the protocol 840 may be terminated (847).

Concentrating Buffy Coat During Collection

Figure 13:
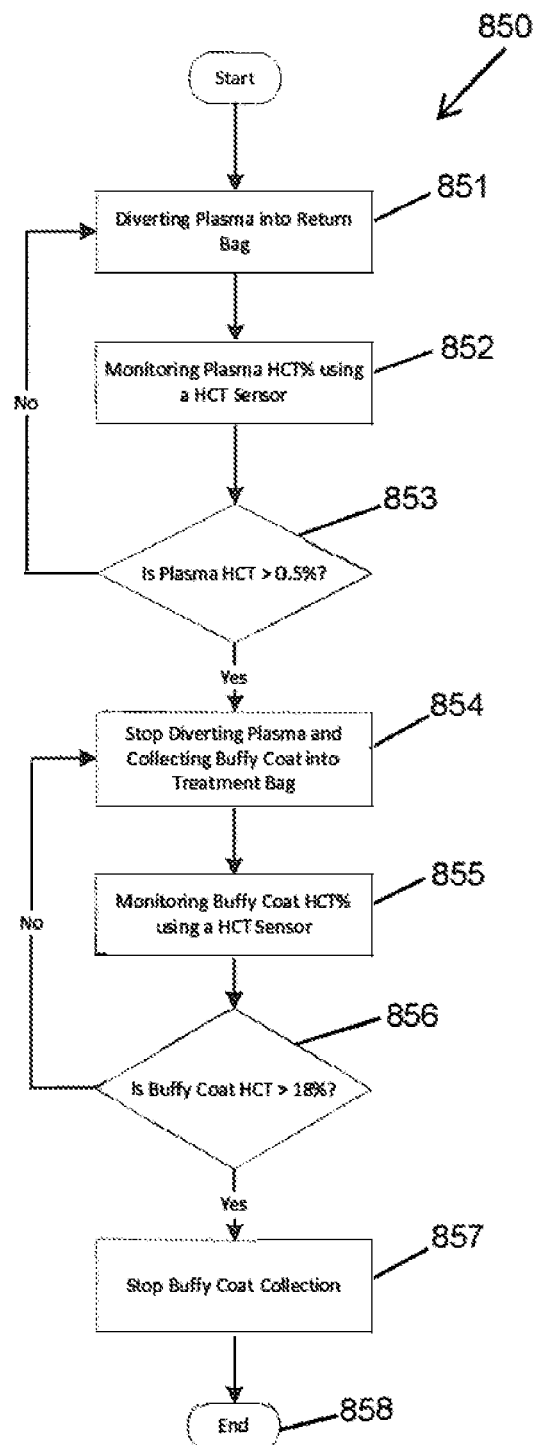
FIG. 13 is an embodiment of a protocol that may be used by a photopheresis system for concentrating buffy coat during buffy coat collection.

As buffy coat is collected, the buffy coat can be concentrated by removing excess plasma. By using a more concentrated buffy coat, the time used for UV light exposure during photopheresis may be decreased. As shown in FIG. 13 for the case of a protocol 850, plasma can be diverted into a return bag (851), and the HCT percentage of the plasma can be monitored using an HCT sensor (852). The plasma continues to be diverted into a return bag (851) and HCT levels continue to be monitored (852) until the HCT sensor detects that the plasma HCT is above a threshold level, such as about 0.5% (853). Once the plasma HCT reaches the threshold level, buffy coat collection begins (854). Buffy coat may be diverted into a treatment bag, while the plasma is no longer diverted into the return bag. The buffy coat HCT percentage is monitored using an HCT sensor (855), and collection of the buffy coat continues until the buffy coat HCT percentage reaches a threshold level, such as about 18% (856). Once the threshold level is reached, buffy coat collection is stopped (857) and the protocol 850 may be terminated (858).

Reducing Patient Residual Blood Volume in Disposable Kit

When a sufficient amount of a patient's blood has been processed by the photopheresis system, treatment concludes, and the fluid remaining in the system may be returned to the patient. The residual volume, i.e., the volume remaining in the photopheresis system, may be reduced by displacing fluid in collection lines into the centrifuge bowl with anticoagulants, and returning the fluid in the bowl to the patient. This may ensure that all fluid taken from the patient is returned to the patient, thus achieving a 1:1 ratio, or nearly a 1:1 ratio. This may be particularly important for pediatric patients.

Figure 14:
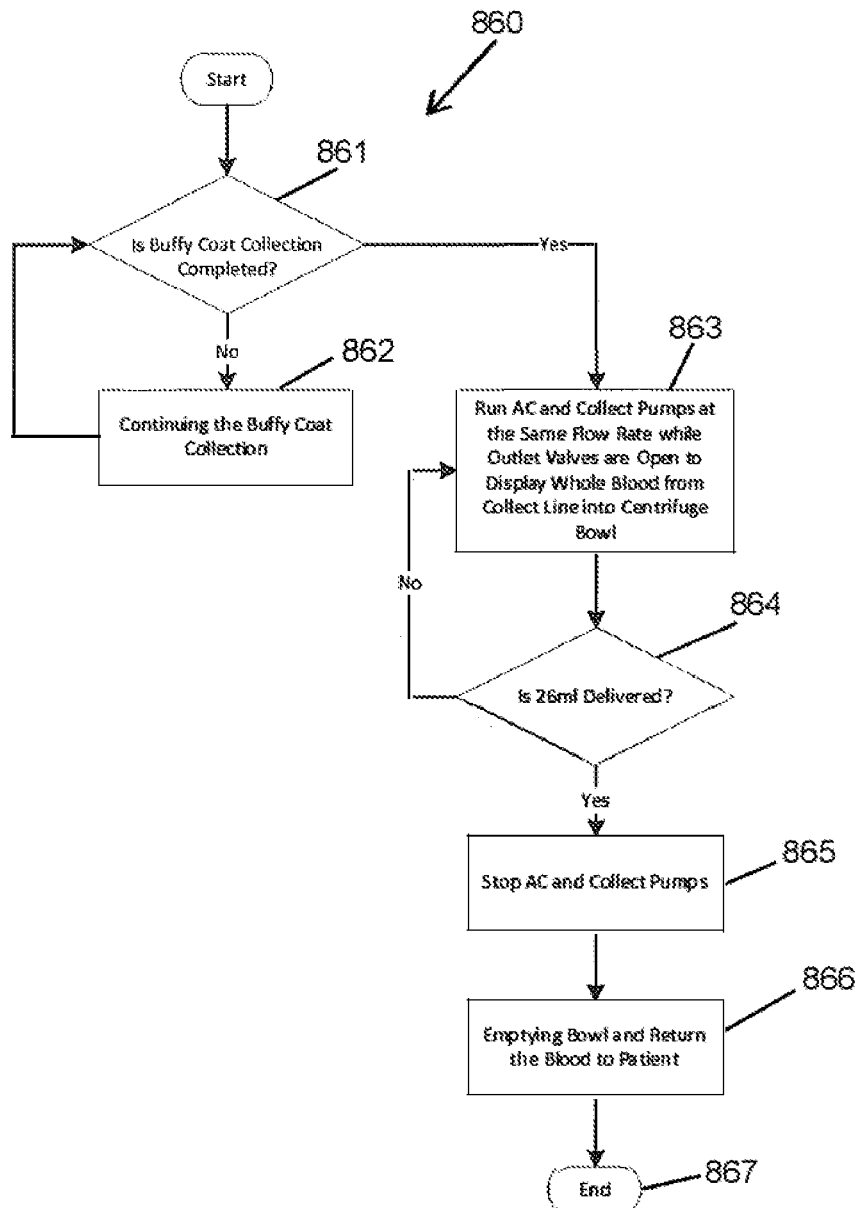
FIG. 14 is an embodiment of a protocol that may be used by a photopheresis system for reducing residual blood volume in a disposable photopheresis kit.

As shown in FIG. 14 for the case of a protocol 860, a module configured to reduce patient residual blood volume may monitor whether buffy coat collection has been completed (861). Once the buffy coat collection is complete (861 and 862), the module may run an anticoagulant and collect pumps at the same (or substantially the same) flow rate (863). At the same time, open outlet valves may be opened, thereby displacing whole blood from the collect line into the centrifuge bowl (863). This may continue until a specified volume of fluid has been delivered (864). For example, the module may measure the volume of fluid until the specified volume, such as about 26 ml, has been delivered. Once the specified volume has been reached, the anticoagulant and collect pumps may be stopped (865), the bowl may be emptied and the blood may be returned to the patient (866), and the protocol 860 may be terminated.

Detecting an Anemic Patient and Unintended Recirculation of Blood

An operator may optimize a photopheresis procedure based on the needs of a particular patient. This, in turn, may result in an optimized procedure time. In some embodiments, the photopheresis system may be configured with a module to detect an anemic patient. The photopheresis system may further be configured to detect unintended recirculation of blood through incorrect application of patient access.

Figure 15:
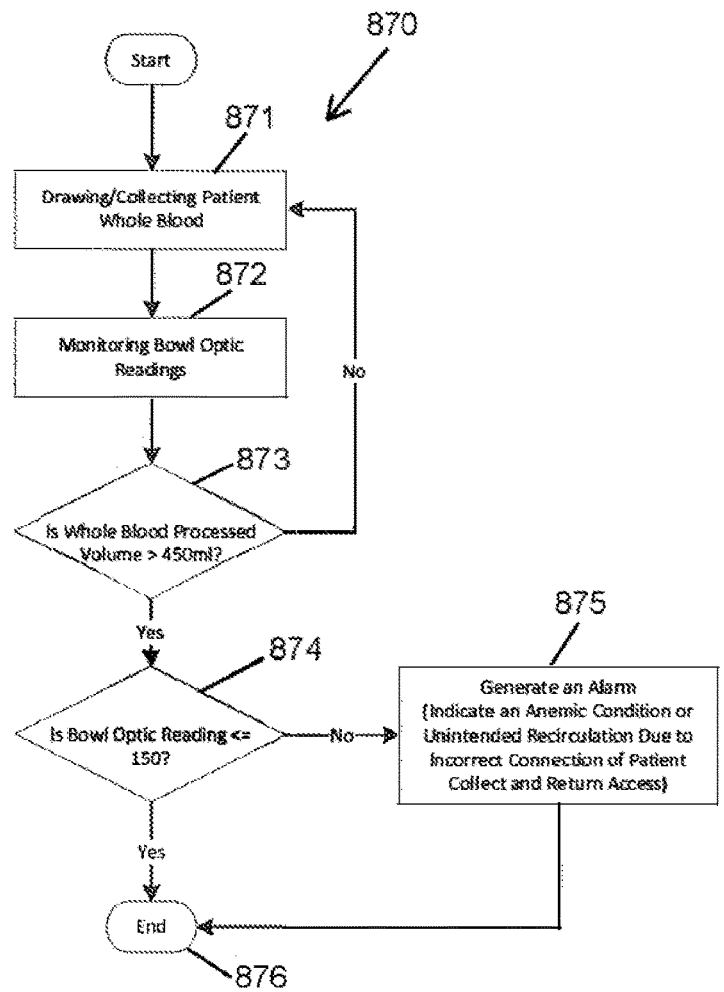
FIG. 15 is an embodiment of a protocol that may be used by a photopheresis system for detecting an anemic patient and unintended recirculation of blood.

As shown in FIG. 15 for the case of a protocol 870, whole blood may be drawn and/or collected from a patient (871), and optic readings of the bowl may be monitored (872). A determination may be made as to whether the whole blood that has been processed exceeds a threshold volume (873). If not, blood collection and monitoring continues (871 and 872). Once attaining the threshold volume (873), a bowl optic reading (i.e., the amount of light reflected back from a laser source) is taken (874) to determine if the bowl optic reading exceeds a predetermined threshold (e.g., about 150; lower numbers indicate less light reflected back, so darker layers have lower bowl optic readings). As long as the reading is below the threshold, the procedure continues and the protocol may be terminated (876), but if the reading is above the threshold, an alarm is generated (875) and the protocol may be terminated (876). The alarm may indicate that the patient is anemic or that unintended recirculation occurred. The unintended recirculation may be the result of incorrect connection to the patient at the collect and/or return access points.

Maximizing Targeted Cell Collection by Recirculating Previously Processed Blood

Figure 16:
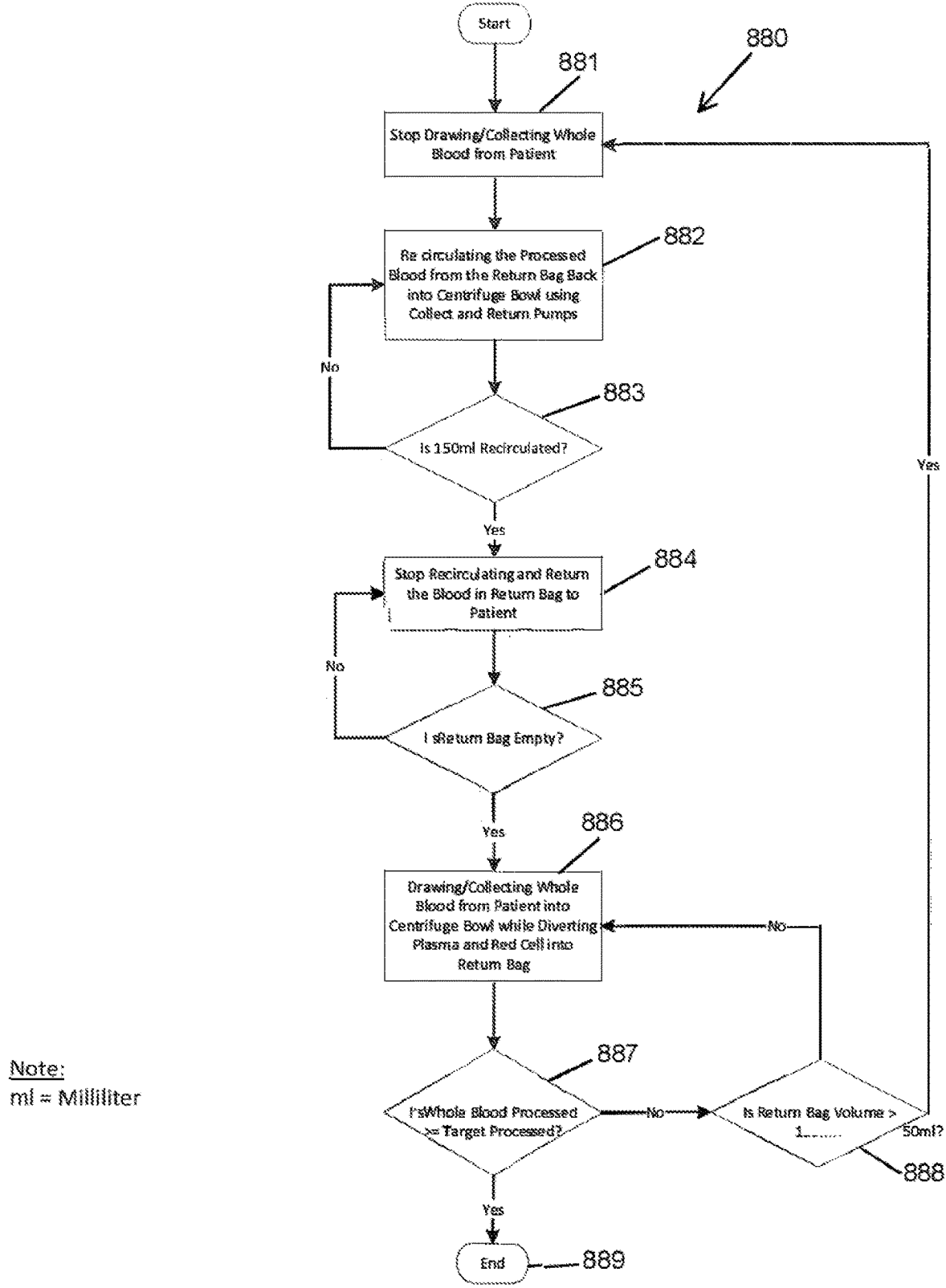
FIG. 16 is an embodiment of a protocol that may be used by a photopheresis system for maximizing targeted cell collection by recirculating the previously processed blood.

The photopheresis system may maximize targeted cell collection, thereby increasing targeted cell yield, by recirculating the previously processed blood. This may decrease procedure time and the amount of total blood processed in order to collect the target amount of targeted cells. FIG. 16 presents an example in the form of a protocol 880.

Whole blood may be drawn from a patient and processed using a centrifuge with a centrifuge bowl. Plasma and red blood cells are diverted into a return bag, and once a threshold amount of fluid is in the return bag (such as about 150 ml), the blood draw/collection may be stopped (881) and as shown in FIG. 16. The processed blood may be recirculated through the centrifuge (882). The processed blood in a return bag is pumped back into the centrifuge bowl using at least one of the pumps used to collect blood from the patient and return the fluids back to the patient. This continues until a threshold amount of processed blood, such as about 150 ml, has been recirculated (883). Once the threshold amount of processed blood has been recirculated, the recirculation stops (884), and the reprocessed blood reenters the patient via the return bag. This continues until the return bag is empty (885), at which point the blood/draw collection from the patient resumes (886). The process may be repeated, as blood is once again drawn/collected and processed through the centrifuge bowl, diverting the plasma and red blood cells into the return bag. A determination is made as to whether the amount of processed whole blood has reached the target volume for processing (887). This determination may be made simultaneously, or almost simultaneously, as the blood draw resumes. If the target volume has been reached, the procedure ends (889); if not, the volume of the return bag is determined (888), and if the threshold amount of fluid is in the return bag, the processed blood is recirculated, and the process continues as described above.

Various inventive concepts may be embodied as one or more methods, of which one or more examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

At least some of the embodiments disclosed above, in particular at least some of the methods/processes disclosed, may be realized in circuitry, computer hardware, firmware, software, and combinations thereof (e.g., a computer system). Such computing systems, may include PCs (which may include one or more peripherals well known in the art), smartphones, specifically designed medical apparatuses/devices and/or other mobile/portable apparatuses/devices. In some embodiments, the computer systems are configured to include clients and servers. A client and server are generally remote from each other and typically interact through a communication network (e.g., VPN, Internet). The relationship of client and server arises by virtue of computer programs running on the respective computers and having a client-server relationship to each other.

Some embodiments of the disclosure (e.g., methods and processes disclosed above) may be embodied in a computer program(s)/instructions executable and/or interpretable on a processor, which may be coupled to other devices (e.g., input devices, and output devices/display) which communicate via wireless or wired connect (for example).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentations, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, and/or method described herein. In addition, any combination of two or more such features, systems, articles, materials, and/or methods, if such features, systems, articles, materials, kits, and/or methods are not mutually inconsistent, is included within the inventive scope of the present disclosure. Still other embodiments of the present disclosure are patentable over prior art references for expressly lacking one or more features disclosed in the prior art (i.e., claims covering such embodiments may include negative limitations).

Any and all references to publications or other documents, including but not limited to, patents, patent applications, articles, webpages, books, etc., presented anywhere in the present application, are herein incorporated by reference in their entirety. One or more features and/or embodiments disclosed in one or more of incorporated by reference documents herein can also be combined with one or more features/embodiments of the present disclosure to yield yet further embodiments (of the present disclosure).

Moreover, all definitions, as defined and used herein, should be understood to control over dictionary definitions, definitions in documents incorporated by reference, and/or ordinary meanings of the defined terms.

What is claimed:

1. A method of operating a blood processing system, wherein said blood processing system comprises a centrifuge, and wherein said centrifuge comprises a first port and a second port, said method comprising:
   introducing blood into said centrifuge through said first port;
   separating said blood into a plasma layer, a buffy coat layer, and a red blood cell layer within said centrifuge and by rotating said centrifuge;
   executing a first monitoring step comprising monitoring a location of an interface between said buffy coat layer and said red blood cell layer within said centrifuge;
   executing a second monitoring step comprising monitoring for an existence of a first condition and a second condition;
   said first condition requiring: 1) an amount of said blood introduced into said centrifuge being both less than a target processed blood volume and within a first predetermined amount of said target processed blood volume; and 2) a determination by said blood processing system that said interface is in a first position from said first monitoring step;
   said second condition being said amount of said blood introduced into said centrifuge being larger than said target processed blood volume by at least a second predetermined amount, wherein the second predetermined amount is greater than zero; and
   directing a fluid flow out of said second port of said centrifuge and into a first container, wherein said fluid flow comprises buffy coat from said buffy coat layer, wherein said directing a fluid flow step is initiated in response to said blood processing system having identified an existence of either said first condition or said second condition, wherein each of said first monitoring step, said second monitoring step and said directing a fluid flow step are executed by said blood processing system.

2. The method of claim 1, wherein said first monitoring step is executed using a bowl optic sensor.

3. The method of claim 1, wherein said first predetermined amount is 75 ml.

4. The method of claim 1, wherein said first predetermined amount is a fixed amount that is independent of a magnitude of said target processed blood volume.

5. The method of claim 1, wherein said second predetermined amount is 75 ml.

6. The method of claim 1, further comprising:
   executing a third monitoring step comprising monitoring a hematocrit of an initial portion of said fluid flow from said directing step;
   and
   assessing said fluid flow for at least part of said directing a fluid flow step, wherein said at part of said directing a fluid flow step is after said initial portion, wherein said third monitoring step, said determining step, and said assessing step are all executed by said blood processing system.

7. The method of claim 6, wherein said determining step comprises using an output of a hematocrit sensor associated with a fluid line extending between said centrifuge and said first container.

8. The method of claim 6, wherein said initial portion of said fluid flow comprises introducing a predetermined fluid amount into said first container.

9. The method of claim 8, wherein said predetermined fluid amount is 10 ml.

10. The method of claim 6, wherein said assessing step comprises comparing a current hematocrit value of said fluid flow from said directing a fluid flow step to a hematocrit threshold, wherein said hematocrit threshold is an amount corresponding to a predetermined percentage.

11. The method of claim 10, wherein said predetermined percentage is 5%.

12. The method of claim 10, further comprising:
   suspending said directing a fluid flow step based upon said assessing step, wherein said suspending step is initiated when said current hematocrit value of said fluid flow from said directing step satisfies said hematocrit threshold.

13. The method of claim 12, wherein satisfaction of said hematocrit threshold comprises said current hematocrit value being equal to or greater than said hematocrit threshold.

14. The method of claim 12, wherein said directing a fluid flow step is based upon a continued execution of said introducing blood prior to said suspending step, and wherein said directing a fluid flow step is based upon directing a flow of red blood cells into said centrifuge through said third port after said suspending step.

15. The method of claim 1, further comprising using a disposable kit, wherein said disposable kit comprises said centrifuge and said first container.

16. The method of claim 1, further comprising:
   terminating said directing a fluid flow step; and
   subjecting contents of said first container to photo therapy after said terminating step.

17. The method of claim 1, further comprising:
   said blood processing system receiving user input that activates a blood prime function of said blood processing system, wherein said introducing blood step comprises introducing donor blood into said centrifuge, followed by introducing patient blood into said centrifuge, wherein said blood prime operation comprises said introducing donor blood step.

18. The method of claim 17, wherein said blood processing system comprises a return bag.

19. The method of claim 18, wherein said blood processing system is configured to preclude transferring contents of said return bag back to a patient at any time during said directing a fluid flow step and when said blood prime function has been activated.

20. The method of claim 18, further comprising:
photo-activating contents of said first container, wherein said blood processing system is configured to preclude transferring contents of said return bag back to a patient at any time during said photo-activating step and when said blood prime function has been activated.

21. The method of claim 20, further comprising:
said blood processing system receiving user input on a rinseback volume; and
reinfusing contents of said first container back to a patient, wherein said blood processing system is configured to transfer said rinseback volume from said return bag back to said patient only after a termination of said photo-activating step, only after a completion of an entirety of said reinfusing step, and when said blood prime function has been activated.

22. A blood processing system configured to execute the method of claim 1.

23. A photopheresis system configured to execute the method of claim 1, wherein said blood processing system is said photopheresis system.

* * * * *